US012606815B2

(12) United States Patent (10) Patent No.: US 12,606,815 B2
Zhang et al. (45) Date of Patent: Apr. 21, 2026

(54) SELF-DIVERSIFYING SYSTEMS AND METHODS OF USE THEREOF

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Jonathan Leo Schmid-Burgk, Cambridge, MA (US)

(73) Assignees: The Board Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 650 days.

(21) Appl. No.: 16/904,529

(22) Filed: Jun. 17, 2020

(65) Prior Publication Data

US 2020/0392482 A1 Dec. 17, 2020

Related U.S. Application Data

(60) Provisional application No. 62/862,522, filed on Jun. 17, 2019, provisional application No. 62/912,602, filed on Oct. 8, 2019.

(51) Int. Cl.
| | |
|---|---|
| *C07H 21/02* | (2006.01) |
| *C07K 14/47* | (2006.01) |
| *C12N 9/12* | (2006.01) |
| *C12N 15/00* | (2006.01) |
| *C12N 15/10* | (2006.01) |

(52) U.S. Cl.
CPC ...... *C12N 15/1037* (2013.01); *C07K 14/4726* (2013.01); *C12N 9/1276* (2013.01); *C12N 15/00* (2013.01); *C12N 15/1024* (2013.01); *C12N 15/1027* (2013.01); *C12N 15/1031* (2013.01); *C12Y 207/07049* (2013.01); *C07K 2319/70* (2013.01); *C07K 2319/80* (2013.01); *C07K 2319/85* (2013.01)

(58) Field of Classification Search
USPC .................................. 536/23.1, 24.3, 24.33
See application file for complete search history.

(56) References Cited

U.S. PATENT DOCUMENTS

2010/0041033 A1 2/2010 Miller et al.

OTHER PUBLICATIONS

"Diversity-generating retroelements" from Wikipedia. Printed on Sep. 9, 2023.*
The definition "Retroelements". Printed on Sep. 9, 2023.*
Sequence alignment between SEQ ID No. 101 and Bacteroides faecis strain BFG-554 chromosome. Printed on Nov. 15, 2024.*
Sequence alignment between SEQ ID No. 115 and Bacteroides Ovatus strain BFG-179 chromosome. Printed on Nov. 15, 2024.*
"Polymorphism in bacteria chromosomes" from Google Search. Printed on Nov. 16, 2024.*
"What is a vector in biology?". Printed on Apr. 24, 2024.*
Overview: Gene regulation in bacteria (article) Khan Academy. Printed on Apr. 24, 2024.*
"Bacteroides faecis strain bfg554" from Google Search. Printed on Apr. 24, 2024.*
"Bacteroides ovatus strain BFG-179" from Google Search. Printed on Apr. 24, 2024.*
Guo, et al., "Diversity-Generating Retroelement Homing Regenerates Target Sequences for Repeated Rounds of Codon Rewriting and Protein Diversification," Molecular Cell 31, published Sep. 26, 2008, pp. 813-823.
Handa, et al., "Template-assisted synthesis of adenine-mutagenized cDNA by a retroelement protein complex," Nucleic Acids Research vol. 46, No. 18, published 2018, pp. 9711-9725.
Schillinger, et al., "Analysis of a comprehensive dataset of diversity generating retroelements generated by the program DiGReF," BMC Genomics 13:430, published 2012, all enclosed pages cited.

* cited by examiner

*Primary Examiner* — Frank W Lu
(74) *Attorney, Agent, or Firm* — F. Brent Nix, Esq.; Johnson, Marcou, Isaacs & Nix, LLC

(57) ABSTRACT

A diversity-generating system comprising: a polynucleotide comprising: a variable region within a sequence encoding a protein or polypeptide, wherein the system is configured to generate a library of diversified molecules with an efficiency of 80% as measured by number of the diversified molecules in total number of molecules. The system may further comprise a template region; and a reverse transcriptase or functional domain thereof.

19 Claims, 37 Drawing Sheets

Specification includes a Sequence Listing.

MATCH LINE TO FIG.

MATCH LINE TO FIG.

MATCH LINE TO FIG.

GCGCCTGCCGA (1,722 reads)

GCGCCTGCCGG (487 reads)

GCGCCTGCCGC (1,022 reads)

Theor. complexity: 4^22 = 1.76E+13

FIG. 5D

**Sequence of *DIV1* (27.3 kDa)**

MKKQSNQTVRMATPGQIKDVISAVVESIPVNNLTYEMAQYFIGRKKWLGTEMKKIFSVDNSHADLIADWQAFYCGLGIDC
DLSGVIIPDDPGGFGRVIIMAQGITPQSGYDLCAKFFPCWKYTDKNLDEVVSERTAKDVYAIRVRDRVEADEELRNRSY
NDLKRQGIIGITLEEREIFELKFFKETAGKHLDIKNWTFCLGSCYDGGNVPSASWRSGEFEVDWCNPGDVFDDLCSRQAVS*

Variable sequence

FIG. 6A

Ligand identification of *DIV1* by phage display

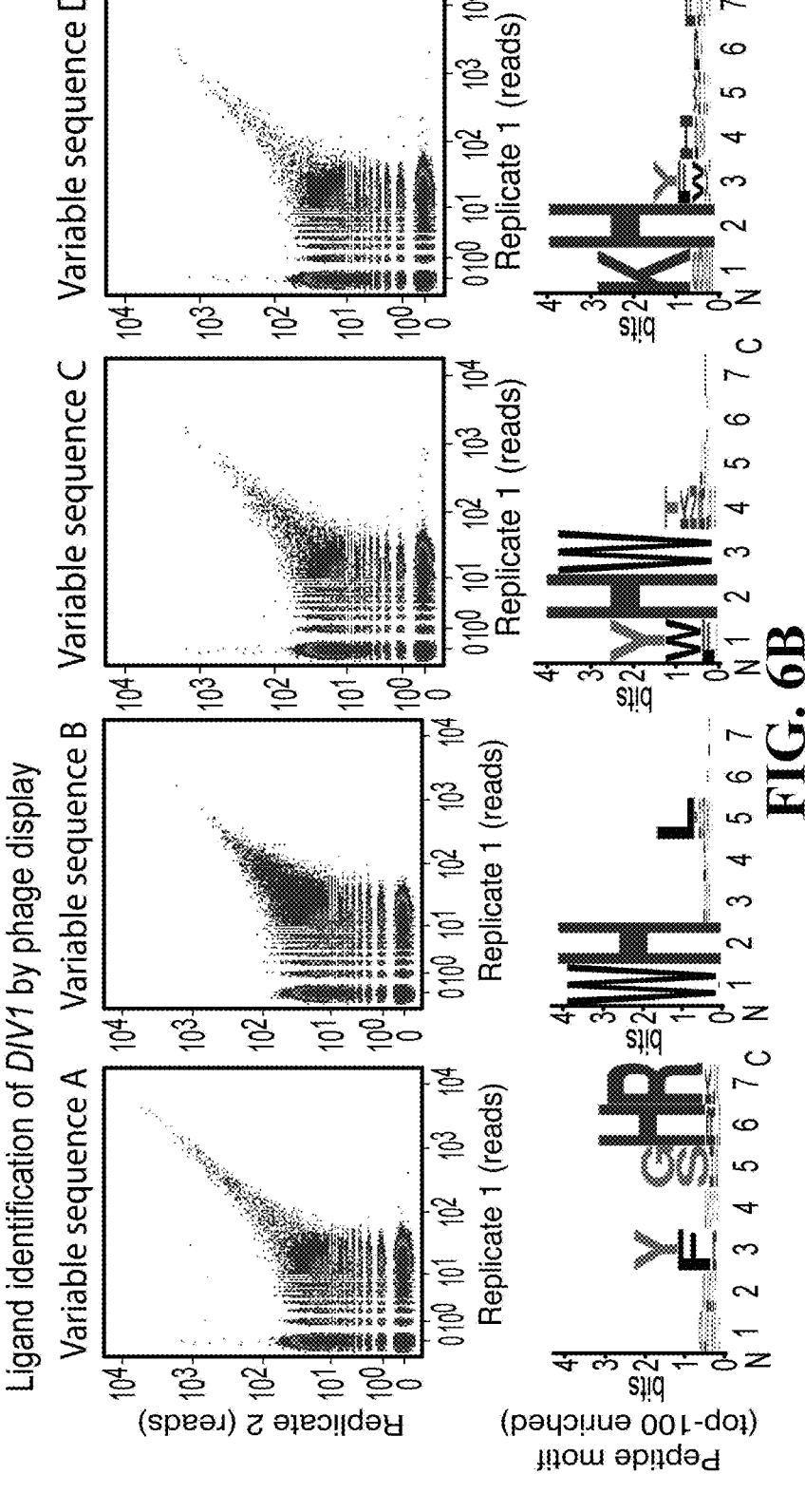

FIG. 6B

Sequence of *DIV18* (21.9 kDa)

MRTFEITEKEVAAAFREAESGEAKKILAALFCKEEMVKPTLDDYKTIRTYEDACKALGEPIFEDPNNLPNHIIALMKLET
ISRALWGRNFQPKPDGEGSKVYWYPWFALWTKKEVEDMNPEQRGAL*VSANADLGAPAGFGCLAALYRSSSADAGYGFRLC
QETEEEKAKYFGQQFIELWAEYILKFNPTVGNRLK*

Variable sequence

FIG. 7A

Ligand identification of *DIV18* by phage display

Variable sequence A

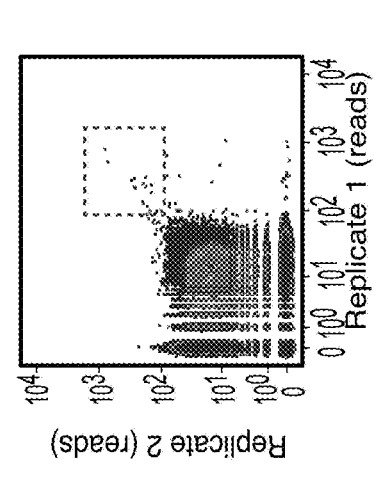

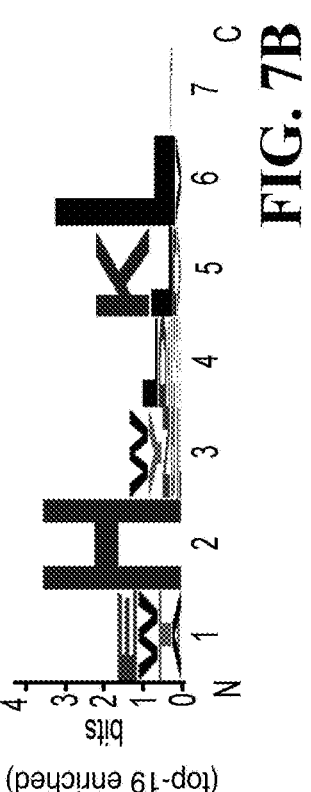

Peptide motif
(top-19 enriched)

FIG. 7B

SEQ ID NO: 1

```
ggagttattt ccgggaacga caaacaaccg gaaccctgaa aagtaagaat cgcattcaaa    60
ctacttctat atacatgagc agtccctaaa ttcccactct gctgcaaatc aacagccact   120
tgtttcataa acgaagtaaa actttccttt ttcattaaaa aataatttaa taattaatat   180
ttactaatnn cacaatttac tttagtaaaa tacgaaaata tatatacaaa gatttacata   240
tataaaatta taatattaaa aactgaaata ttcacattat ctatcaaatt tattttata   300
catttgcgca gttttttaaa caaataatca ttttaattac taaaaaacaa caaagttatg   360
aacaacaatg aaccagctgc cgaacactac agcatcaatg gattcaagta tttctccgag   420
ttggcgaaag aatattttcc agatctggca aacgcctctt ccgccagcaa aaaaatgcgc   480
aaacgcatca aagcagacaa gacgttgaac gaacaactgg ctgccgcgta ttacacctgc   540
caaacaatcg acatcagtcc cgaaatgcaa ctaatccttt accgccattg gggacctccc   600
cacatcgacc tgccgaccaa cgtttaatta cgtagtagaa aacgaaaaca tcgacaagga   660
ataaaaagaa aatcgaacta tatattttta aatatatcat ttatcttttt attgtttatt   720
atgtattcca ctttgcgttc accactttt tcggaaaaga agataactat catttataca   780
gctatttaca gaaagaaaaa agcgttccac aaagcgttcg gcaaaatgac cgtttttttc   840
attccaaaca gagcctccga atcctcccaa cgaaggctct gtttatctcc ggcagaagtt   900
ctatcaaaca caaacagagc atccgtttca tctcctgatc gcttcttcgc cccatgaaag   960
aaaacaaaaa tacaacaact tacgtaccac aactattctt cttcgtccac acccgtccac  1020
aaacagacac acccccttgca aaccgcacgg gaatagcgta cttttacaga aaatttaaat  1080
aacactcaat gaaaaatttc aattttcaag ccatgctgaa acatggtttt ctcattatcc  1140
ctaaagcctt actacagcag cagatagaag accgncacat gcaagaagga gaaatagaag  1200
ctctcctgaa aattctgatg aaggtcaatt attcggatac actctacaac gaccgtcaaa  1260
ataaaaactg cctgtgtaaa agaggcgaaa gcctgtttag ttatcgcgac tggagccaca  1320
tcttccactg gtctgtcgga aaagccttca ggttcataca cgagcttgcc acgctgggaa  1380
ttatagaaat catctctcac cccaacaatt cctccctgca tattcgtgtc gtcgaatacg  1440
ataaatggat gggagttccc gatagcgaca agcagaaaaa gaaagccgtc aacgaaaagt  1500
ttcacctgtt ctggaatgaa ttccacagca tcacacagct ccccaaagag aatatcgcca  1560
aagcacaacg cgaatggaaa aagttgggcg acaaggaaca gcaactcgcc atcgacagga  1620
tagaggaata ttatttccac caaacgaaca tcaatttcct tctccatgcc gccagctatt  1680
tatccaacaa agcttttctt aacgaatact gataatatga ataccgaaaa cagagtttcg  1740
ccacaggctc ccgaaataga agaagctatc atcggcgcct gcctgataga acaggggagcc  1800
ataccactgg tagccgacaa gctgcgtccc gaaatgttct acgtcctgcg ccatcaggtt  1860
atctatgccg ccatactggc catgtatcat gcaggaataa agatagacat cctcaccgta  1920
aaagaagagc tttcccaccg tggaaagctc gaagaggcgg gcggaccgtt cggcatcacc  1980
caattgagca gcaaggtggc aacctccgcc catnttgaat atcatgcgca gatcgtacac  2040
gagaaatacc tgcgacgcga aatgattctg gggttcaaca aactcctcgc ctgttcgcta  2100
gacgaaacga tggatattga cgactcactg gtagacgcgc ataacctgct cgaccgtctg  2160
gaaggcgaat tcggccataa caaccacatg cgcgacatgg atgaactaat gaccgccacc  2220
atggtagaag ccgaaggacg tatcgccaac aacaaaacg gagtaaccgg cctccctacc  2280
ggactggcgg atctggaccg catgacgtcc ggactacaga aaggcgagtt ggtggtggtc  2340
gccgccgtc ccggcgtagg aaaaacggca ttcgcactac acatggcacg aagcgcagca  2400
atggcagggt atgccgtagc tgtctacagc ctcgagatgc aagggaacg actagcagac  2460
cgatggctga cagcggtcag cgaaatcagc gcccgccatt ggcgatcggg aaccgtcagc  2520
caacaggaac tcgtagaggc acgcacaaca gccgctgacc tcaaacgcct gccgatacac  2580
gtagacgaca gcacatcggt caacatggaa catatacgtt ccagcgcgcg actgctgcaa  2640
agccaacatg cgtgcgatgc tattattatc gactacctgc aactctgcga catgacgacc  2700
ggtcaaaaca accgcaaccg cgaacaggaa gtggcacaag cnacccgcaa ggcaaaattg  2760
ctagccaaag aactgaatgt accagtcgta ctgcttagcc agctaaaccg cgaatcggaa  2820
aaccgccctg ccggccgtcc cgaactggct catctccgcg agagcggagc tattgaacag  2880
gatgcagacg tcgtcatgct gctctaccgt cccgcccttg caagggtgac gaccgaccgg  2940
gaaagtggtt atcccaccga aggtctggga gtagtcatca tagccaagca acgcaacgga  3000
```

FIG. 9B-1

```
gagacaggaa  acgtctattt  cagacataat  ccggaaatga  ccaagatcac  cgaatatgtc   3060
cctccgttag  agtatatgct  gaaacatgcc  aaataagaaa  cagttacact  aataatatac   3120
aattttatat  tacaacatat  agcataaatc  attttctcat  tttatttcat  tatacataca   3180
anatatatag  caaaacactt  gactttccct  ctcatatttc  gtatatttgt  aatgtcgtaa   3240
ggacagagaa  aattttatta  cttaaacctt  aactttttat  tgtatgaatg  tattagtgga   3300
gcgctatcag  cgcagaaagt  atgtgaatca  accggattca  cagatgttgt  attatgtacg   3360
ccagaaatcg  ggcacagtga  gagtgatgga  catcaacaag  ctggcggatg  ccatcgaagc   3420
gaactcctcg  ctcactgcag  gagacgtgaa  gcatgccatt  gaggcttttg  tcgagcagtt   3480
acgcctatcg  cttacccagg  gcgacaaggt  gaaggttgac  ggattgggta  cgtttcatat   3540
cacattgagc  agcgaggggg  cagaaaaaga  gaaagattgc  acggtcgcca  gcatccgcaa   3600
agtaaatgtc  cgtttcgtgg  cggacaaggc  gcttcaattg  gtaaatacga  gccatgccac   3660
tacccgaggc  gaaaataatg  tcgatttttat  cctggcagca  aagggcgacg  gagaaggtga   3720
cgatgacgga  aatagcggna  gcggtggaaa  cagcggcgga  agcggagaag  ctccggaccc   3780
ggcagcttaa  tctttaaaac  agcgccgcat  ggatattacg  gagtgatttc  tacagttact   3840
ctcnatgcgg  tttctgtttt  cttctacatt  tattttttaa  ttctcaattt  tcaatcctca   3900
atttattaaa  atgcttgata  aaatcataga  gatcattata  acgatcctgc  cctttctggg   3960
cagtaaccgc  aaaaagcgca  aagtaatggc  gcaagaagta                            4000
```

FIG. 9B-2

SEQ ID NO: 2

```
tacgccgggc  cgtctgggaa  actacatgga  tgacgaaggc  aaggaagagg  caggccccgc     60
tgccggcgcg  gcaggaaacg  cagcgggcgg  gaacagccag  cccgagcgta  tcatcgccct    120
ccttggcgga  cgggagaaca  ttgaatttgt  ggacgcctgc  atgaccaggc  tccgcgtgac    180
agtgaaggat  ctctccaagg  tggctgaact  tccggcgtgg  aaggcagagg  cgccatggg    240
ccttgtgaag  aaagacaacg  gcatccaggc  aatttacgga  cccaaggcgg  acgtgctgaa    300
atcggatatc  aacgatatcc  tgtaacaatt  cagcaccccg  gaaaaaatga  gtgaaatatg    360
aacggggagc  ctgctcaccg  ggcagatttt  gctcaatacg  cagaggaaag  aactatgaga    420
ctgcttacta  tcaatattca  cagccatgga  agtgactttg  aaccggaact  ttatcatcag    480
aagatgaagg  cgctggcggc  atttatgaag  gaagaagaga  tcgatgccgc  ggcgatccag    540
gaatgcagtg  aagaggagga  caggccggtg  gtctccggcc  ccctccccat  gcattgggtg    600
ccggccggac  cggactcccg  cgtccgggag  gataactgtg  cgctggtcct  ggcggaggaa    660
cttcaggccc  tgcagcagga  gtactggtgg  acctggaccg  gagcgaagct  cgggtacgga    720
aaatacaatg  agggtctggc  catcttcagc  cgccgccctg  ttacaggcgc  ggacagtttc    780
tatatttccg  gcgtccggga  cttctccaac  tggaagaccc  ggaaggcgct  ggcggcctgc    840
accgctgacg  ggcctgcctt  tttgagcgtc  cacatgggat  ggtggaatga  tccggaggaa    900
aacttccggg  ggcagatgga  acggctgcag  aaggcgctcc  gcgaaaggaa  gcttcgtccg    960
caggacggtt  ctgacagttt  ccttatggga  gatttcaaca  gtcccgcagc  gatccgcgga   1020
gagggaaggg  acatggtcct  ggacctcggg  tggcgggaca  gttatgagga  tgccgaaata   1080
aaagacagcg  gcatcaccgt  tccgggaaac  atcgacggat  ggagggacgg  tgaacatacg   1140
ggcatgcgcc  tggattatat  ctggaccgca  aaaaggcaca  gggtgcttca  gtcaaaggtg   1200
gtcctgaacg  ggatcagcgg  gccggtgctt  tccgaccatt  tcggagtcct  ggcggtgatc   1260
gaatgaataa  aggagcagac  agcatgagag  aaagtggaat  tcttcttgcc  atcagcagcc   1320
ttccttccga  atacgggatc  ggctgcttca  gcagggaagc  atatgagttt  gcggaccgcc   1380
tttcagaggc  gggccagagt  tactggcaga  tcctgccgct  ggggccggtg  ggatacggag   1440
attcaccgta  ccagtccttc  tccaccttcg  cggcaaccc  ttactacatt  tcacctgaga   1500
cgctggtgga  aaagggatgg  atcactgagg  cggactgccg  cgaagccggc  ctttcttccg   1560
acccgcgcgg  tgtggattac  gtgctgcagt  accaacgccg  ctatgagctg  ctccggaagg   1620
```

FIG. 9C-1

```
cgtacagaaa cagccggatc gaagagaatg agaagttccg ggcgttcacg gagaagacgg     1680
aatggcttcc ggactacgcg ctgttcatgg ctctgaagga agagaacgga ggaaggccct     1740
ggtacgaatg ggaagatccg ctgagactca gggatccgga agccttggcc gcggcgcggg     1800
aacgcctgga ggaaggcatc ggtttctgca gtttcctgca gtttgagttt tacgaagagt     1860
ggatgcagct gaaggactac gtgaaccgga agggaatacg gatcatcgga gacatcccga     1920
tctatgtatc cctggacagt tcagacgtct gggcggatcc ggaacttttc cngctggatg     1980
aaaaccgccg acagaccgcg gcggcgggct gcccgccgga tggcttcagc gctgtgggac     2040
agctctgggg caacccactc tatgactggg actatcacaa aaagacctgt tttgcctggt     2100
ggctgaaacg tcttaaaaac tgctttgata tttatgatgt gatgcggatc gaccatttcc     2160
gcggcttcga tgaatatttt tccattcctg ccggtgcgga ggacgcaaga gcaggccatt     2220
gggagaaggg accggcatg gatctgttcc ggaaggtctc ggaagccttc ccgggacggg     2280
agatcatcgc ggaggatctg gggtatgtga cggacagtgt ccggcagctg gtgaaggaca     2340
gcggctatcc cgggatgaag gtcctggaat ttgcctttga ctcaagagat tccggctgtg     2400
cggaggatta ccttccccac aattacgaaa agaacagtgt ggtctacacc ggcacccatg     2460
acaacgagac ggtgaccggc tggttttccg agggcctgaa gccggaggag aaggaggcag     2520
tcagagacta tttctgcgac catacgactc ccgacgccgg gatgcacata ccctgatct     2580
gcgccgccat gcgaagcgtc agcagactct gcatcatccc catgcaggac cttctggggt     2640
acggaaacga ggcaaggatg aacgctcctt ccacctacgg aaacaactgg aaatggcgtc     2700
ttctgaagga tgaattcgga gagaaggaag tgaagacgct gtatgagatc acgaagcggt     2760
acggaaggat cggaaaatga gaaaagagga nngnnnntnn nnnaanngnn nnntaccnnn     2820
nnnnagnnca ntnannnnnt nnnnnnntnn ttannncnnn ncanngnaat natcnnnnnn     2880
nnnnnnnnnt ntnnnnnnnn nnnnnnnnnn nnnnnnnnnn ncnnngntgt natnnnnnnn     2940
ntnnnnnncn nnancngnnn tnngntntnn tnnnnnnnnn annntnnnnc nnnagtannn     3000
nnnncncntn nnaannnnnn nnnannnnnn tnnnnnnnnn nnnnnnnnan nanannncna     3060
annnntnncn tcgnnnnnnt gnnnnnnnaa tnngnnntnn ntnnnnnnnc nnntnaannn     3120
nntnnttcnn nnnnnnnnnn nnnnnngnnn nnnnngntna nnnnaannnt ntnnaannan     3180
gnnnnannnn annnnngnna nnnnnnnnnn nnnntnnnnn nnnnannnnn nnnnnannnn     3240
nnnnnngnnn nnnnnannnn nnnnnnnnnn nnnnnnnnnn nnnnnnnnnn nnnnnnnnnn     3300
nnnnnnnnnn nnnnnnnnnn nnnnnnnnnn nnnnnnnnnn nnnnnnnnnn gnnnnannnn     3360
nnnnnnnnnn nnnnntnnnn tntnnnntnn nnnnnnncnn nnnnnttntt nnnnngcnnn     3420
nnnnnnannn nnnnngnnnn nnnnnnnnnn nnnnnnnnnn nnnnnnnnna nnnnnnnnnn     3480
nngnnnnnnn nnnnnnagnn ncnnnnnnnn nnnncnnncn nntnnnnnna ntannnnnnn     3540
nnnnnnnnnn nnnnnnnnnn nnnnnnnnnn nnnngnnnc nnnnnnnnnt nnnannnnnc     3600
nnnnnnnncn nnnncnncnn nnnncnnnn nnnnannann ncnnnnnnnn nnnnnnnnnn     3660
nnnnnnnnnn tntntnnnnn nnnnnnnnnn nnnnnnnngn nnnnnnnngn nnnnnnnnan     3720
gnnnnnnnnn nnnnnnnnnn nnnnnnnnnn nnnnnnnnnn tnnnnnnnnn nnnnnnnnnn     3780
nnnnnnnana nnnnnnnnnn nnnnnnnnnn nnnnnnnnnn nnnannnnnn nnnnnnnnnn     3840
nngnnnnnnn nnnnnnnnnn nnncnnnnnn nnnnnnnnnn nnnnnnnnnn nnnnnnnnnn     3900
nnnnnnnnnn nnnnnnannn nnnnnnnnnn nnnnnnnnnn nnnnnnnnnn nnnntnnnnn     3960
nnnnnnnnnn nnnnnnnnnn nnnnngnnnn nnnnnnnnnn                          4000
```

FIG. 9C-2

SEQ ID NO: 3
```
MKKQSNQTVR MATPGQIKDV ISAVVESIPV NNLTYEMAQY FIGRKKWLGT EMKKIFSVDN      60
SHADLIADWQ AFYCGLGIDC DLSGVIIPDD PGGFGRVIIM AQGITPQSGY DLCAKFFPCW     120
KYTDKNLDEV VVSERTAKDV YAIRVRDRVE ADEELRNRSY NDLKRQGIIG ITLEEREIFE     180
LKFFKETAGK HLDIKNWTFC LGSCYDGGNV PSASWRSGEF EVDWCNPGDV FDDLCSRQAV     240
S                                                                    241
```

FIG. 9D

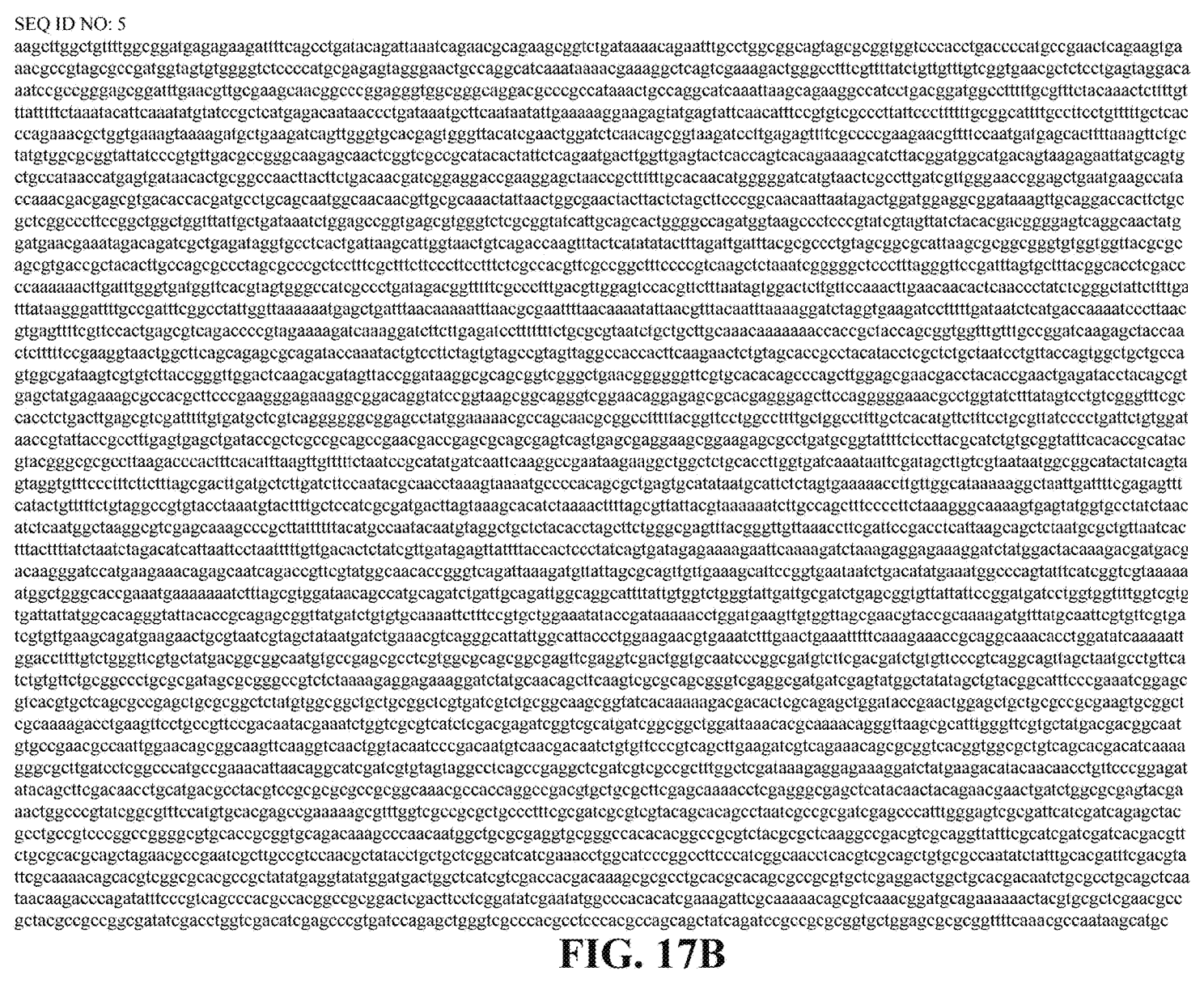

SEQ ID NO: 5 aagcttggctgtttggccggatgagagaagagattttcagcctgatacatcagaacgcagaagcggctcggatcagatttaaatcagataatttcctgccgccgcagtagccgcggtagccggtggtccaccgaccatgccgaactcagaagtga
aacgccgtagccgcgatggtagttggggtctcccatgcggaggaacctgcaggccatcaaaacgaaaggctcagtcgaaagactggccttcgttttatctgttgttgtcggtgaacgctctccgagtaggaca
aaccgccgccggagcggagattgaacgttgcgaagcaacgccggaagcgccgcgaggcgtggccgaccgcccgccataaactgccaggcatcaaattaagcagaaggccatcctgacggatggccttttcggccatttgccttccgttttggctcac
ttattttctaaataccattcaaatatgtatccgtcatgagacaataaccctgataaatgcttcaataatattcaacattccgttcgtcgcctattccctttaatccgtttcgcgcattttgccttccgtttccgattctgtttttcgctcac
ccagaaacgctggtgaaagtaaaagatgctgaagatcagttgggtgcacgagtgggttacatcgaactggatctcaacagcggtaagatcctttgatcaatgacttggttgagtactcaccagtcacagaaaagcatcttacggatggcatgacagtaagagaagattatgcagtg
tatgtggcgcggtattatcccgtgttgacgccgggcaagagcaactcggtcgccgcatacactattctcagaatgacttggttgagtactcaccagtcacagaaaagcatcttacggatggcatgacagtaagagaagattatgcagtg
ctgccataaccatgagtgataacactgcggccaacttacttctgacaacgatcgggaggaccgaaggagctaaccgcttttttgcacaacatgggggatcatgtaactcgccttgatcgttgggaaccggagctgaatgaagccataccaaa
ccaacgacgagcgtgacaccacgatgcctgcagcaatggcaacaacgttgcgcaaactattaactggcgaactacttactctagcttcccggcaacaattaatagactggatggaggcggataaagttgcaggaccacttctgc
gctcggcccttccgctggctggtttattgctgataaatctggagccggtgagcgtgggtctcgcggtatcattgcagcactggggccagatggtaagccctcccgtatcgtagttatctacacgacgggagtcaggcaactatggatgaacgaaatagacagatcgctgagataggtgcctcactgattaagcattggtaactgtcagaccaagtttactcatatatactttagattgatttaaaacttcatttttaatttaaaaggatctaggtgaagatcctttttgataatctcatgaccaaaatcccttaacgtgagttttcgttccactgagcgtcagaccccgtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggtaactggcttcagcagagcgcagataccaaatactgtccttctagtgtagccgtagttaggccaccacttcaagaactctgtagcaccgcctacatacctcgctctgctaatcctgttaccagtggctgctgccagtggcgataagtcgtgtcttaccgggttggactcaagacgatagttaccggataaggcgcagcggtcgggctgaacggggggttcgtgcacacagcccagcttggagcgaacgacctacaccgaactgagatacctacagcgtgagctatgagaaagcgccacgcttcccgaagggagaaaggcggacaggtatccggtaagcggcagggtcggaacaggagagcgcacgagggagcttccagggggaaacgcctggtatctttatagtcctgtcgggtttcgccacctctgacttgagcgtcgatttttgtgatgctcgtcaggggggcggagcctatggaaaaacgccagcaacgcggcctttttacggttcctggccttttgctggccttttgctcacatgttctttcctgcgttatcccctgattctgtggataaccgtattaccgcctttgagtgagctgataccgctcgccgcagccgaacgaccgagcgcagcgagtcagtgagcgaggaagcggaagagcgcccaatacgcaaaccgcctctccccgcgcgttggccgattcattaatgcagctggcacgacaggtttcccgactggaaagcgggcagtgagcgcaacgcaattaatgtgagttagctcactcattaggcaccccaggctttacactttatgcttccggctcgtatgttgtgtggaattgtgagcggataacaatttcacacaggaaacagctatgaccatgattacgccaagcgcgcaattaaccctcactaaagggaacaaaagctggagctccaccgcggtggcggccgctctagaactagtggatcccccgggctgcaggaattcgatatcaagcttatcgataccgtcgacctcgagggggggcccggtacccagcttttgttccctttagtgagggttaattgcgcgcttggcgtaatcatggtcatagctgtttcctgtgtgaaattgttatccgctcacaattccacacaacatacgagccggaagcataaagtgtaaagcctggggtgcctaatgagtgagctaactcacattaattgcgttgcgctcactgcccgctttccagtcgggaaacctgtcgtgccagctgcattaatgaatcggccaacgcgcggggagaggcggtttgcgtattgggcgctcttccgcttcctcgctcactgactcgctgcgctcggtcgttcggctgcggcgagcggtatcagctcactcaaaggcggtaatacggttatccacagaatcaggggataacgcaggaaagaacatgtgagcaaaaggccagcaaaaggccaggaaccgtaaaaaggccgcgttgctggcgtttttccataggctccgcccccctgacgagcatcacaaaaatcgacgctcaagtcagaggtggcgaaacccgacaggactataaagataccaggcgtttccccctggaagctccctcgtgcgctctcctgttccgaccctgccgcttaccggatacctgtccgcctttctcccttcgggaagcgtggcgctttctcatagctcacgctgtaggtatctcagttcggtgtaggtcgttcgctccaagctgggctgtgtgcacgaaccccccgttcagcccgaccgctgcgccttatccggtaactatcgtcttgagtccaacccggtaagacacgacttatcgccactggcagcagccactggtaacaggattagcagagcgaggtatgtaggcggtgctacagagttcttgaagtggtggcctaactacggctacactagaagaacagtatttggtatctgcgctctgctgaagccagttaccttcggaaaaagagttggtagctcttgatccggcaaacaaaccaccgctggtagcggtggtttttttgtttgcaagcagcagattacgcgcagaaaaaaaggatctcaagaagatcctttgatcttttctacggggtctgacgctcagtggaacgaaaactcacgttaagggattttggtcatgagattatcaaaaaggatcttcacctagatccttttaaattaaaaatgaagttttaaatcaatctaaagtatatatgagtaaacttggtctgacagttaccaatgcttaatcagtgaggcacctatctcagcgatctgtctatttcgttcatccatagttgcctgactccccgtcgtgtagataactacgatacgggagggcttaccatctggccccagtgctgcaatgataccgcgagacccacgctcaccggctccagatttatcagcaataaaccagccagccggaagggccgagcgcagaagtggtcctgcaactttatccgcctccatccagtctattaattgttgccgggaagctagagtaagtagttcgccagttaatagtttgcgcaacgttgttgccattgctacaggcatcgtggtgtcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtctaagaaaccattattatcatgacattaacctataaaaataggcgtatcacgaggccctttcgtc

FIG. 17B

SEQ ID NO: 6

FIG. 17C

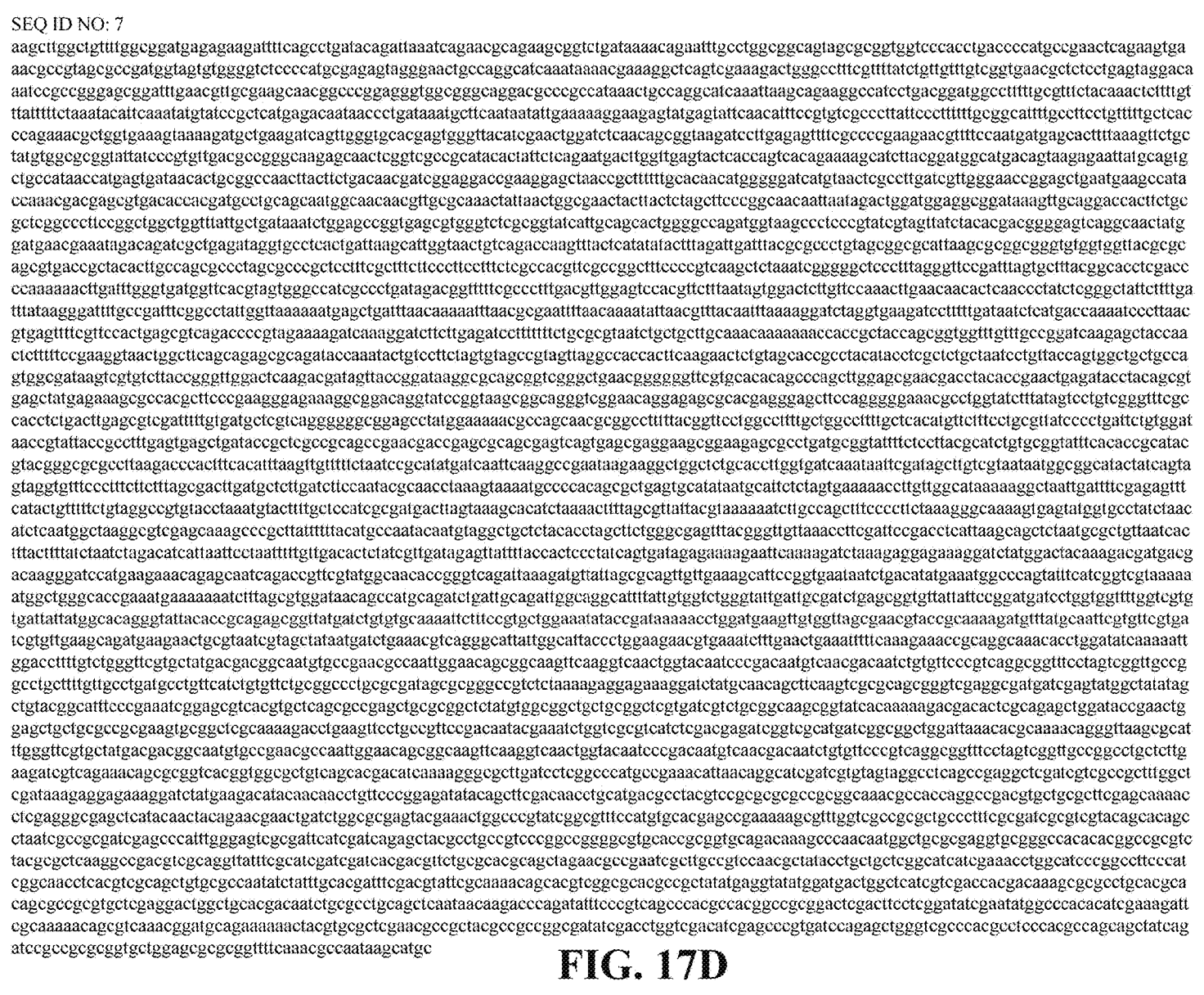

SEQ ID NO: 7 aagcttggctgtttggcggatgagagaagaattttcagcctgatacagattaaatcagaacgcagaagcggtctgataaaaacagaattgcctggcggcagtagctggagttccctcctcgagtaggaca
aacgccgtaggcgccgatggtagtgtgggtctcccatgccaggcaggtagggaactgccaggcatcaaataaaacgaaaggctcagtcgaagactgggccttcgttttatctgttttgtcggttctacaaactctttgt
aatccgccggagcggagccggattgaaccgttgcgaagcaacgcccgagcgccgccataaactgccaggcatcaaattaagcagaaggccatctgacggatggccttttgcggcatttgccttcctgttttgcttcac
ttattttctaaatacattcaaatatgtatccgctcatgagacaataaccctgataaatgcttcaataatattgaaaaaggaagagtatgagtattcaacatttccgtgtcgcccttattccctttttgcggcattttgccttcctgtttttgctcac
ccagaaacgctggtgaaagtaaaagatgctgaagatcagttgggtgcacgagtgggttacatcgaactggatctcaacagcggtaagatcctt...

FIG. 17D

SEQ ID NO: 8 aagcttggctgttttggccgatgagtgagagaagattttcagcctgatacagattaaatcagaacgcagaagyggttctgataaaaacagaatttgcctgtgcggcagtagtcgcggtgggttgtccgcactgacccatgccgaactcagaagtga
aacgccgtagccgcgatggtagtgtggggtctcccgatgcgagagtagtagaggaactgcaggccatcacaataaaacgaaaggctcagtcgaaagactggccttcgtttatcgtgtttgtcggtgaacgctcctcgagtaggaca
aatccgcgcgggaggcgagcgatttgaacgtgcgaagcaacgcccgcgaggtggcggccaggcatcaaattaagcaaagcagaaggccatcctgacggatggccttttgcgtttgccttcctccgtttttgctcac
ttattttctaaatacattcaaatatgtatccgtccatgagacaataacccctgataaaatgcttcaataattagtattcaacattccgtcgccctaattccttttgccgcattttgcggcattttgccttccttgtccctcctgtttttgctcac
ccagaaacgctggtgaaagtaaaagatgctgaagatcagttgggtgcacgagtgtggtttacatcgaactggatcttcaacacgggaactcttgagtgtttcgccccgaagaacgtttccaatgatgagcactttaaagttctgc
tatgtgggcggtattatcccgttgacgccgggcaagagcaactcggtcgccgcatacactatctcagaatgacttggttgagtactcaccagtcacagaaaagcatcttacggatggcatgacagtaagagaattatgcagtg
ctgccataaccatgagtgataaacactgcggccaacttactttgcgcaacgatcggaggaccgaaggagctcaaccgcttttgcacaacatggggatcatgtaactcgccttgatcgttgggaaccggagctgaatgaagccata
ccaaacgacgagcgtgacaccacgatgcctgcagcaatggcaacaacgttgcgcaaactattactggatggaggcggataaagttgcagatcttactgctatatcccaatccccgcatgcgctggtggtatcaatcgctaagctgcc
gctcggcccttccgcggtttattgctgataaatctggagccggtgagcgtggggtctcgcggtatcattgcagcactggggccagatggtaagccctcccgtatcgtagttatctacacgacggggagtcaggcaactatggatgaacgaaata
gatgaacgaaatagacagatcgctgagataggtgcctcactgattaagcattggtaactgtcagaccaagtttactcatatatactttagattgattactttgctacacccctcggttcctcctttactcttcctttacggcactctctcga
agcgtgaccgctacaccgcactgcctctctttcctccactttcgccacgctacgagatggtttcgccacatggctttaatgatggatcaatggctactgaccaagcagtacattagtcaagctgcttacctcctgatctcgggtttcgc
ccaaaaaacttgattttggttctccatatctttggatggcacgagtgcggtcactgcctaaaaagtgctgattactcactttacaaatattggatcaatcaacactcaacactcaccactatctcgggctattctttcctttga
ttttataaggaggttttgcgatttcgcattcggaaagacccgtagaaagatgctttaaccaaataattaacgttacatttaaaatgacttcatttaaaaagatcctttgatatccatcgataatctcatgaccaaaatcccttaac
gtgagttttcgttccactgagcgtcagaccccgtagaaaaagatcaaaggatcttcttgagatccttttttttctgcgcgtaatctgctgcttgcaaacaaaaaaaccaccgctaccagcggtggtttgtttgccggatcaagagctaccaa
ctcttttccgaaggtaactggcttcagcagagcgcagataccaaatactgttcttctagtgtagccgtagttaggccaccacttcaagaactctgtagcaccgcctacatacctcgctctgctaatcctgttaccagtggctgctgccca
gtggcgataagtcgtgtcttaccgggttggactcaagacgatagttaccggataaggcgcagcggtcgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaacaggagagcgcacgagggagcttccagggggaaacgcctggtatctttatagtcctgtcgggtttcgc
cacctctgacttgagcgtcgatttttgtgatgctcgtcaggggggcggagcctatggaaaaacgccagcaacgcggcctttttacggttcctggccttttgctggccttttgctcacatgttctttcctgcgttatcccctgattctgtggat
aaccgtattaccgcctttgagtgagctgataccgctcgccgcagccgaacgaccgagcgcagcgagtcagtgagcgaggaagcggaagagcgcccaatacgcaaaccgcctctccccgcgcgttggccgattcattaatgcagctggcacgacaccgatcat
gtacgggccgcctttaagccctttagggttccgatttagtgctttacgggcacctcgacccatcatttaagcatttctttaatatggctcataacaccccttgtattactgtttatgtaagcagacagttttattgttcatgatgatatatttttatctt
gtgaatgttcttccttttccttttcctttagcggctacctttgacctttacttatttctactgtctcacctttctgctttttgcgtcatggtaaagatgctaagagtagttgaaacctgataaagagtggtgcctactctaac
catcgttttttctgctgctgaggcctgcctccgaaggccgttttattcttttttacatgccaataacatgagtgctgtctacacctctcagattcttctctacaccctactctgtcggcaatataccatagagactgataggtctaatgcg
ttacttttaatcctactactatcaattttttgttggcactcctattcttgtaggtatcttacactctctatctctattgttttttacagtatgtagctgtctattccggcaatttctttccgttggctttctatacctgtctaaggctcaggcctctgagg
acaaggcgatttgaagaaacagagcaatcagactggcccgcagttatgagctgagtttacacttatttcctgacacctcagatataatatatcagcttagatagtgcaattgggccgagtttagtaatatatttagctggctctatagcttaatctaa
atgggcggcggcaccgaatttgaaaaaacttcatgctgccgacattagggtgagtttagggctctataattctcactcctcctctgcgttatctgtccctgcggagtataggtaagcaaagtggagcatttatttctcaaattcccgcatattccctagctgcttagctg
tgatttattaagcacaggtcgatccgcagaggcccgggcgagagttaattttgcggcgagttctgtccaatctcaaagccggcctttgtgccggcacggcttggtttgtccgagttacctctctgtatataggctgggtttaggtt
tcgtgttttcgctcggcttcgagagaggcgcggcgaggttgcgggtgtctagcagttcctgtccaccttcaatatcggctattttctgggttaaatcgagttctgggcgacggagttacctctgctctttcctcagatggcttattcagcacagt
catcgtgtcttcgcggcctgcggagacattgctaaagttcctggcggccctgagtagacagatctagaaaagagggtaatactggctgggatacgctctctgggtgggtttgcgctgagcttgctcgagcactgggggaagttgatatcgataaatgct
ggtcacggtgctctcagcggcgccgagtcgatcggctcatgtggtcgcttcaaacgtggctctcgcgtatcatccgacagtcgggatctctggagttcgttcacctgatctgcagaaagaagctgcagacctgcaagaagaaagtgcggaagttgg
ctcgcaaaagtggctctcgacatcggacgtttcctgccggttaccgaccaccatgccaatgctggctcgtgtagctgtaggaaaacacgggattaagacttaacaccgttcggttcttcgtatcgggtgctctatggcagcgcaa
tgtgccgaacgccaatgtgccaaggttcaaggtccacctgaccggctacaatcagtatcaatgcatacacagtgggttctgccgaattccgcacacagctctaatcgcatctcgccacacggctgctcatcagcaccataagagctcagccgga
aaagccgcttgaactgcacgatttggttgcagtttggacgacttcacaggggtaggccggttggaagcaaggtggatgactacaaagacgatgacgac
gatacagcttcgacaatctcggcatgctgacttaccggtgagcgagccggtcgaggcatcacaaccagaggtcgccacagcggagtcatacagcaacacgttcccgga
gaaactggccctatcgcgtttcatgcagcaggagaacagcccctttgctcgggcggttgcaccactgctggctcatcggctgtcatcggtctgggagcgagtctcgatcatcgtcatcgatcagagct
acgctcgcacgcagactagaaccgctttgcttgccaacgccaaagccgctccaacctcacgctgccacctcacgctcgccacatcgaaagttgcccacacatcgaaagttgcccacacatcgaaatattgccctcctcgattcgac
gttctgccacgcagtcagagctcagatcggctcgccacccaacgccgcaacctcacggtctgctctcgccacgctggtgtctcgaggactggctgcaggctgcagcagtcgccgcagatccccgtgctcgaggactggctgcctggaagct
gtcattaacacgacccagatattccgtccggcgtatatgccacgagccctccgaaacattgccccacatcgaatatgccccacaccgaatatgccccacacggaagttgcgcgagcacatcgcaacaccgtgctctcgaac
gccgctacgccgcggccgatattgacaatctcggccgattccgacagccccgttgatcccagcgtatcagacatcccgccacgctccccacgctcgccgattcagcagcgccggttgttgctgaagtgctgagcgccgctttcaacgccaataagcaatg
c

FIG. 17E

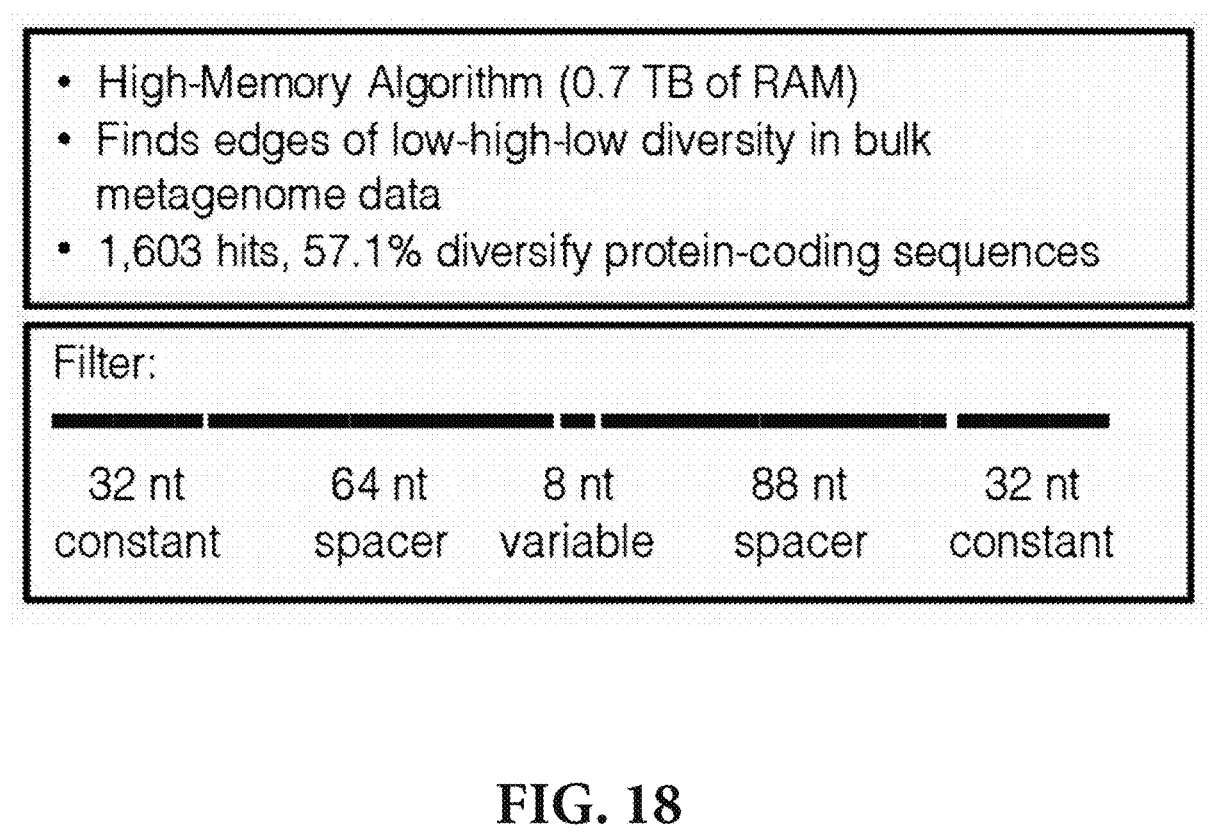

- High-Memory Algorithm (0.7 TB of RAM)
- Finds edges of low-high-low diversity in bulk metagenome data
- 1,603 hits, 57.1% diversify protein-coding sequences Filter:

| 32 nt constant | 64 nt spacer | 8 nt variable | 88 nt spacer | 32 nt constant |

FIG. 18

SELF-DIVERSIFYING SYSTEMS AND METHODS OF USE THEREOF

CROSS-REFERENCE TO RELATED APPLICATIONS

This application claims the benefit of U.S. Provisional Application Nos. 62/862,522, filed Jun. 17, 2019 and 62/912,602, filed Oct. 8, 2019. The entire contents of the above-identified applications are hereby fully incorporated herein by reference.

STATEMENT REGARDING FEDERALLY SPONSORED RESEARCH

This invention was made with government support under Grant Nos. MH110049 and HL 141201 awarded by the National Institutes of Health. The government has certain rights in the invention.

REFERENCE TO AN ELECTRONIC SEQUENCE LISTING

The contents of the electronic sequence listing ("BROD_4170US_ST25.txt"; Size is 19,914,482 bytes and it was created on Aug. 12, 2025) is herein incorporated by reference in its entirety.

TECHNICAL FIELD

The subject matter disclosed herein is generally directed to self-diversifying elements and methods of use thereof.

BACKGROUND

Bacteria and virus actively diversify their proteins and nucleic acids to adapt to changing environment. Such diversity mechanisms can be used to generate libraries of diversified molecules. Such molecules may be used for screening novel binding partners for antigens, pathogens, and other types of target molecules. However, there is a need for systems and methods for generating diversified molecules with high efficiency and sufficient degree of diversity.

SUMMARY

In one aspect, the present disclosure provides a self-diversifying system comprising a polynucleotide encoding one or more open reading frames that encode a diversified molecule, the diversified molecule comprising one or more variable regions, wherein the system is configured to generate a library of diversified molecules with an efficiency of at least 80% as measured by a number of the diversified molecules in a total number of molecules in the library.

In some embodiments, the polynucleotide further comprises a template region. In some embodiments, the self-diversifying system is a diversity generating retroelement (DGR) system. In some embodiments, the self-diversifying system is a non-DGR system. In some embodiments, the system further comprises a reverse transcriptase or functional domain thereof. In some embodiments, the polynucleotide comprises a sequence selected from SEQ ID NOs: 98-1699. In some embodiments, the sequence encodes c-type lectin fold or a fragment thereof. In some embodiments, the sequence encodes a protein or polypeptide capable of binding to a protein or a nucleic acid. In some embodiments, the variable region and the template region have a sequence homology of less than 80%. In some embodiments, the polynucleotide further comprises a regulatory sequence. In some embodiments, the regulatory sequence comprises one or more ribosomal binding sites. In some embodiments, the regulatory sequence comprises an inducible promoter. In some embodiments, the diversified molecules are proteins. In some embodiments, the diversified molecules are polynucleotides. In some embodiments, the sequence encodes DIV1 or a fragment thereof. In some embodiments, the sequence encodes DIV18 or a fragment thereof. In some embodiments, the sequence encodes a protein from Table 1 or the sequence is from Table 2. In some embodiments, the diversified molecules comprise one or more binding partners of a target molecule. In some embodiments, the target molecule is a protein. In some embodiments, the target molecule is an antigen. In some embodiments, the target molecule is a polynucleotide. In some embodiments, the system generates the library of diversified molecules when introduced to cells. In some embodiments, the variable region is within an open reading frame. In some embodiments, the system comprises a vector comprising the polynucleotide. In some embodiments, the system comprises a vector comprising the polynucleotide and a nucleic acid sequence encoding the reverse transcriptase. In some embodiments, the reverse transcriptase is error prone.

In another aspect, the present disclosure provides a method of generating a library of diversified molecules, comprising introducing the system herein in cells, wherein the system generates the library of diversified molecules in the cells. In some embodiments, the method generates the library of diversified molecules with an efficiency of 80%. In some embodiments, the cells are *E. coli* cells. In some embodiments, expression of Mutator S and/or Exodeoxyribonuclease 10 are reduced or depleted in the cells.

In another aspect, the present disclosure provides a method of identifying a diversity-generating system comprising a). identifying loci with higher diversity in contigs larger than 1 kb in a database; b). selecting contigs comprising the identified loci in a), wherein each selected contig comprises a sequence encoding a polypeptide of least 100 amino acids; and c). expressing polynucleotides comprising at least a portion of the polypeptide-encoding sequence in the selected contigs from b) in cells, thereby confirming self-diversifying function of the polynucleotides. In some embodiments, the database is a metagenome database. In some embodiments, the contigs in a) are larger than 3 kb.

In another aspect, the present disclosure provides a method of screening binding partners of a target molecule, comprising a). obtaining of a library of diversified molecules using the system herein; b). performing one or more assays to determine interaction between the diversified molecules and the target molecule; and c). selecting a subset of the diversified molecules based on results of the one or more assays. In some embodiments, the one or more assay comprise phage display, toxin inhibition assay, toxin survival assay, bacterial surface display, bacterial two-hybrid display assay, an enzyme-linked immunosorbent assay (ELISA), immunoprecipitation assay, or a combination thereof. In some embodiments, the target molecule is an antigen.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

Figure 5A:
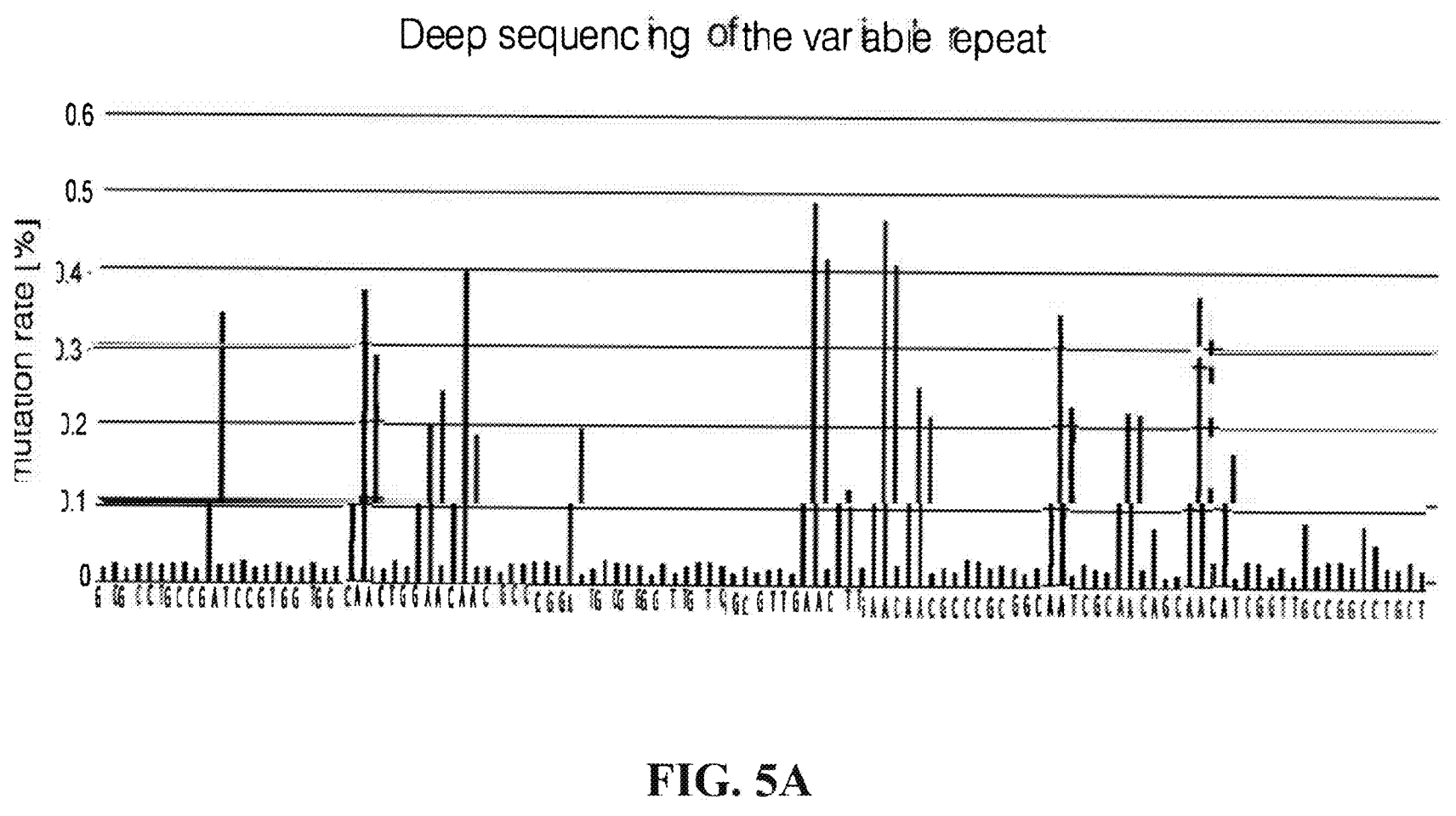
Figure 5C:
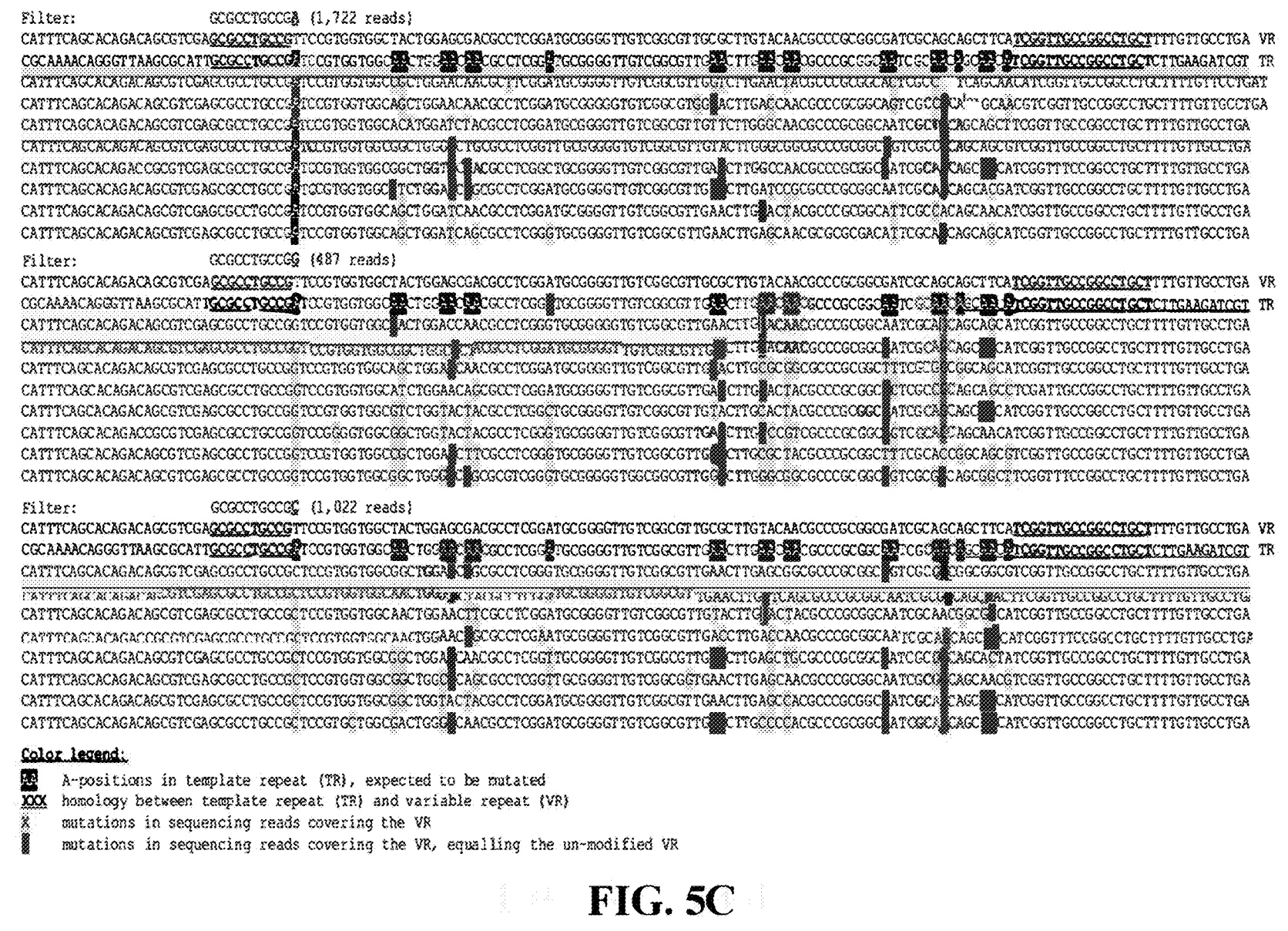
Figure 5D:
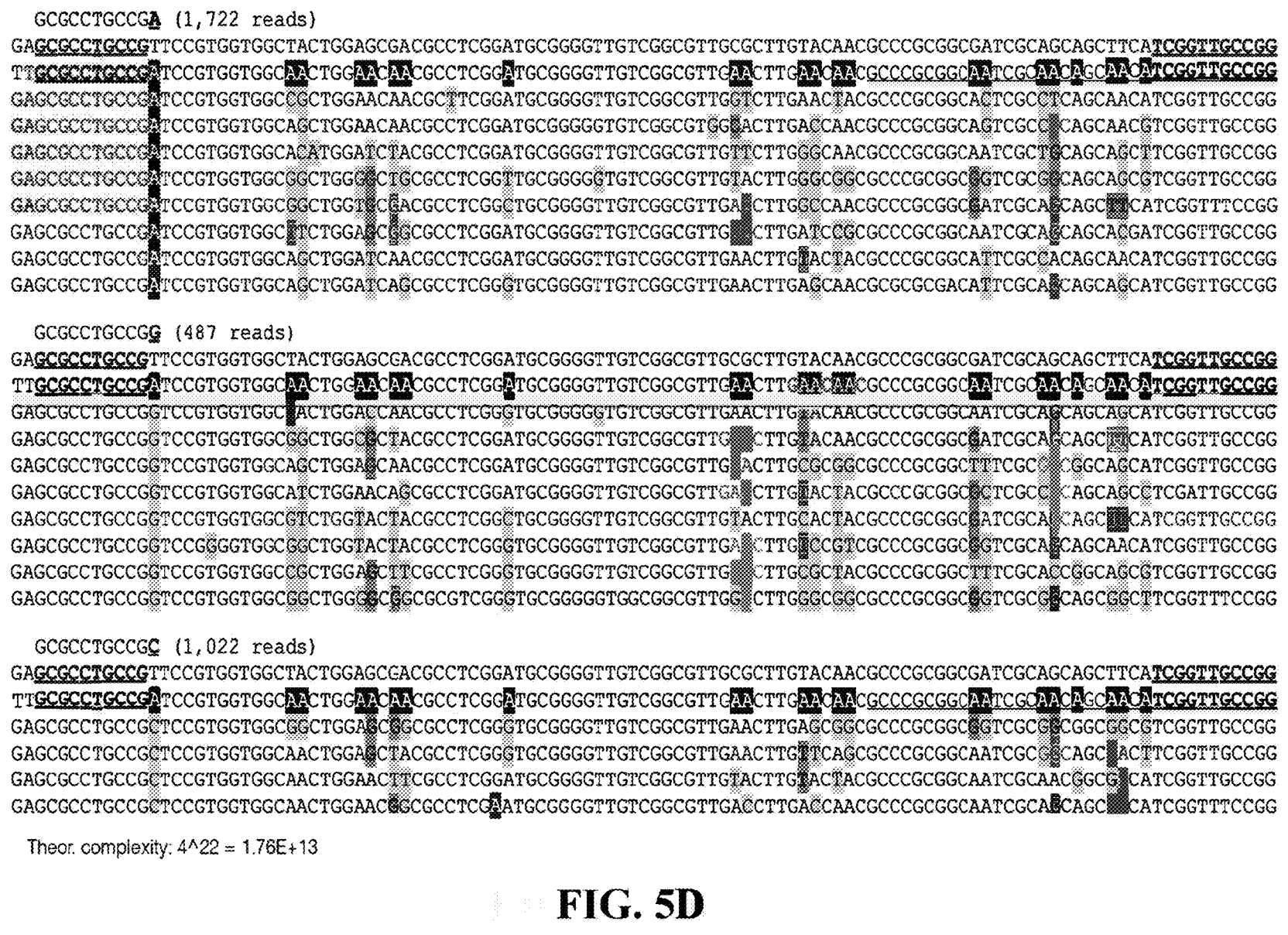

FIGS. 5A-5D show results from testing the selected diversity-generating system (SEQ ID NOs: 9-73).

FIGS. 6A-6C show the DIV1 sequence (SEQ ID NO: 3) and tested characteristics.

FIGS. 7A and 7B show the DIV18 sequence (SEQ ID NO: 4) and tested characteristics.

FIGS. 17A-17E show various constructs derived from Hit 214 and those components sufficient to drive self-diversification after 24 hrs (SEQ ID Nos: 5-8).

FIG. 18 shows an example search strategy for diversity generating systems.

Figure 1A:
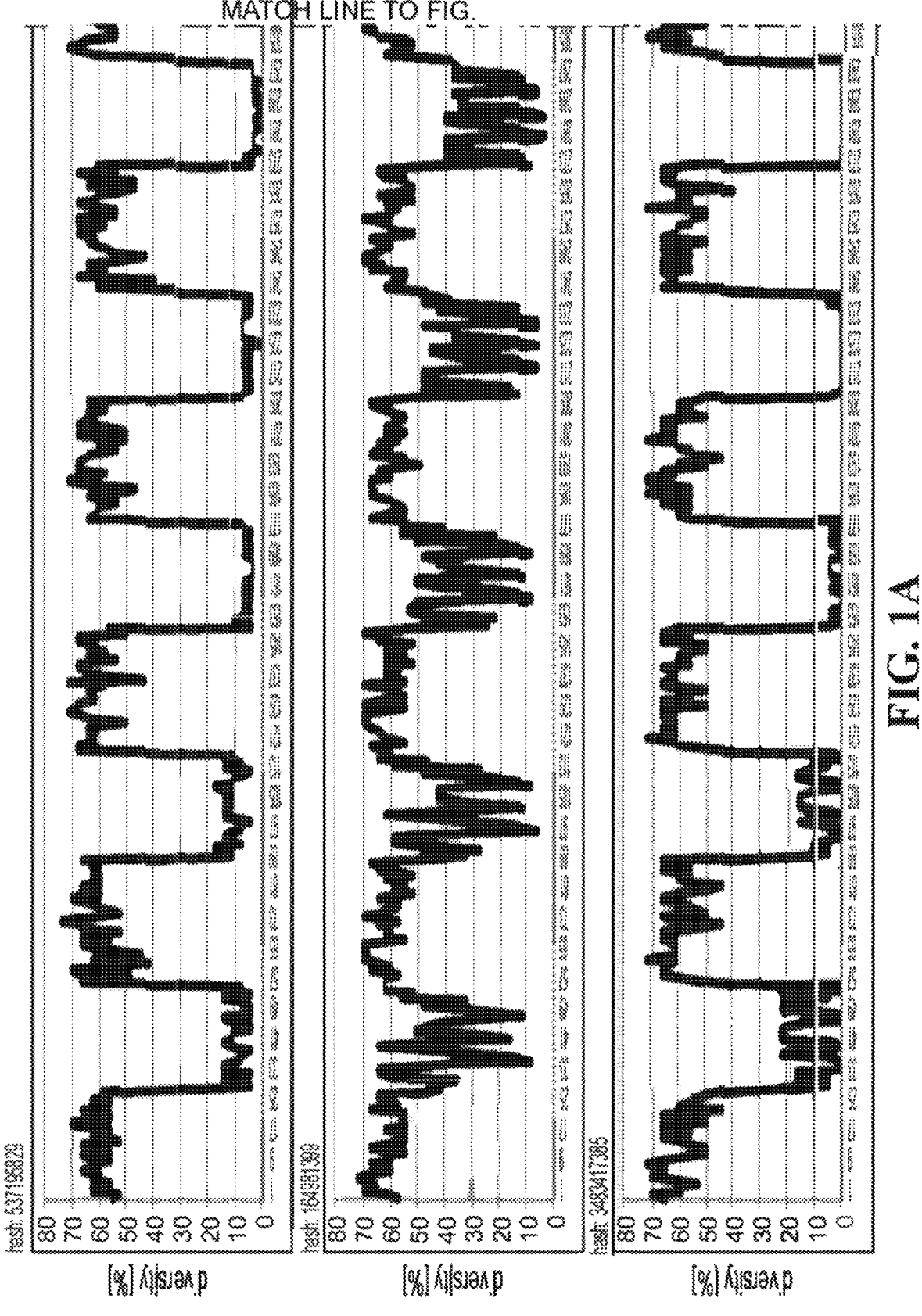
FIGS. 1A-1D show results from identifying potential diversifying systems from metagenome database (SEQ ID NOs: 98-1699).
Figure 1B:
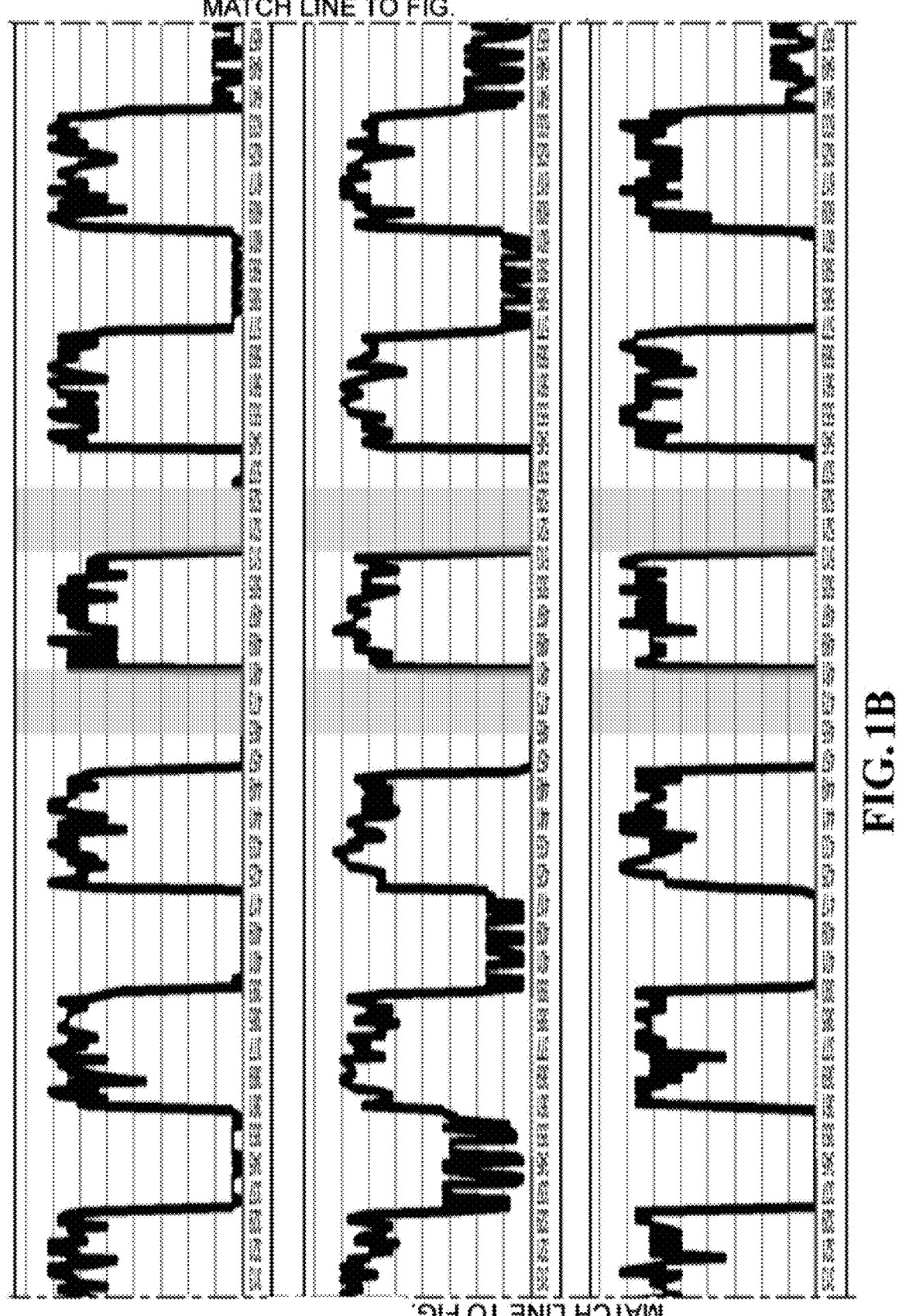
Figure 1C:
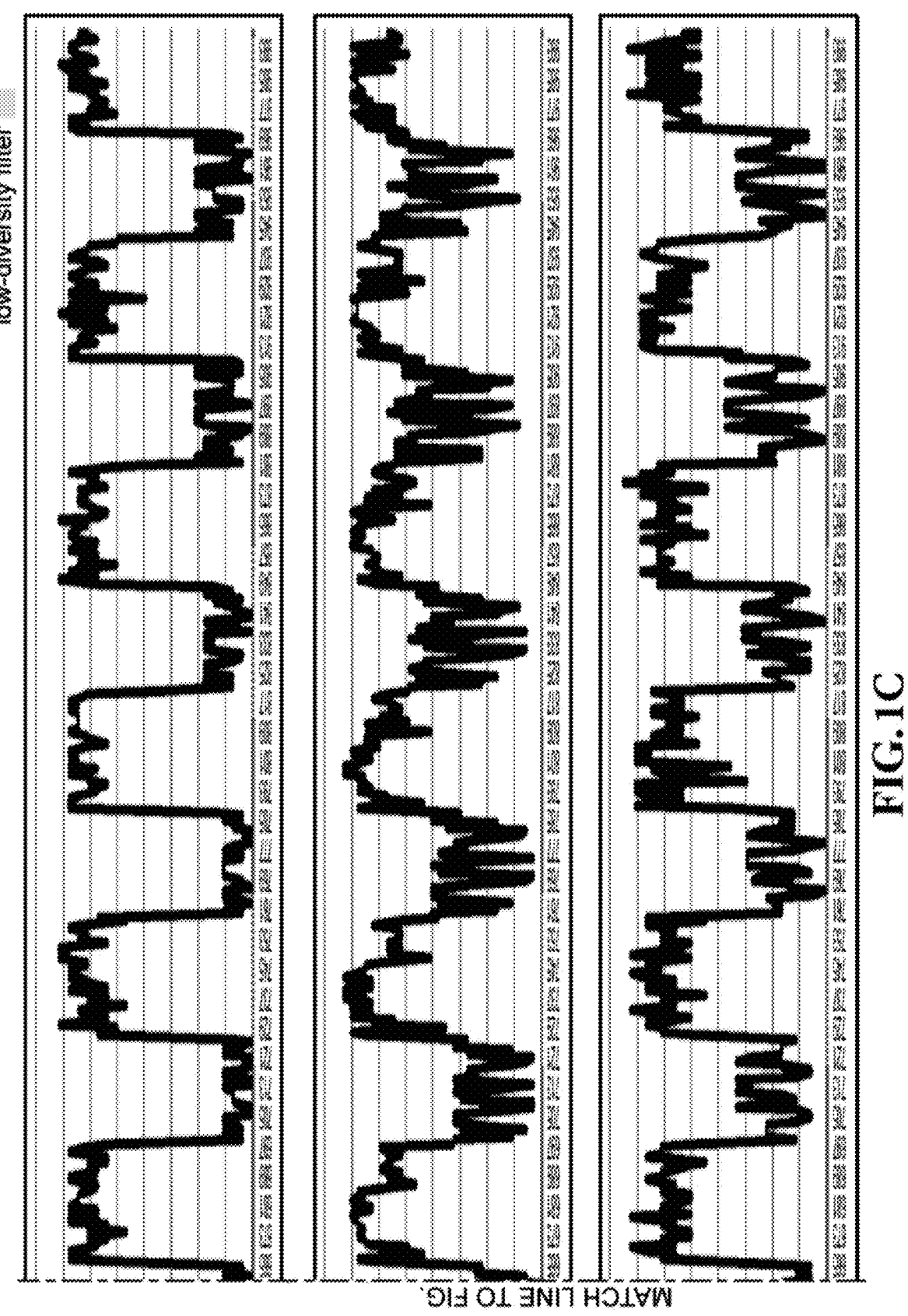
Figure 1D:
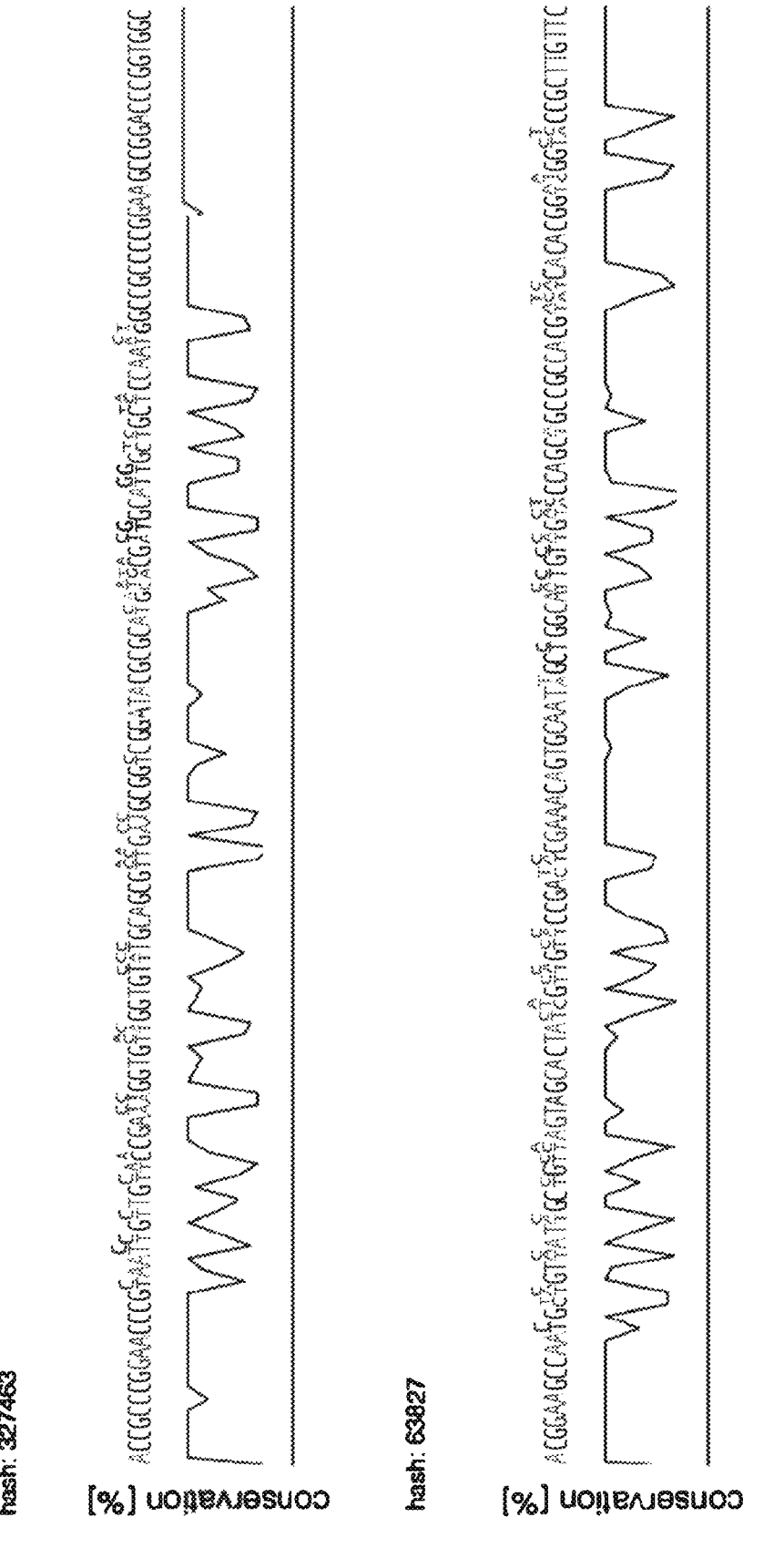

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E.

A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−5% from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides engineered self-diversifying systems. A self-diversifying system comprises a self-diversifying polynucleotide. The self-diversifying polynucleotide may encode one or more open reading frames. At least one of those open reading frames may encode a self-diversifying element. The diversifying element may be a sequence or structural feature encoded by the self-diversifying polynucleotide that leads to generation of multiple sequence variants ("diversified molecules") from the self-diversifying polynucleotide. While the process of generating diversified molecules from a self-diversifying system may comprise processes like transcription or replication of the self-diversifying molecule, such processes are not necessarily limited to canonical replication or expression of a gene. For example, processing may refer to expression of a RNA transcript of the self-diversifying polynucleotide that may then be reverse transcribed. During the reverse transcription process, the self-diversifying element(s) may dictate a type or frequency of mutation resulting in a population of cDNAs generated. The diversified molecules may comprise such a population of cDNAs or polynucleotide or polypeptides expressed from such cDNAs. In yet other embodiments, diversified molecules may arise when such intermediate molecules, such as the aforementioned cDNAs, are re-incorporated into copies of the original self-diversifying polynucleotide. Thus, in certain example embodiments, diversified molecules may refer to a population of self-diversifying molecules that have gone through a process resulting in incorporation of variable sequences at one or more defined location in the self-diversifying polynucleotide sequence. In such contexts, the self-diversifying element may comprise multiple components, for example, a region that leads to generation of multiple sequence variants and a second component that defines where such sequence variants, once generated, are incorporated back into copies of the original self-diversifying polynucleotide. The systems described herein may comprises homologous engineered systems that incorporate self-diversifying elements arising from different naturally occurring systems or comprise naturally occurring systems that have been further engineered to increase the efficiency of self-diversification or increase the number of self-diversifying elements.

The systems herein may comprise one or more polynucleotides. As used herein, a polynucleotide may be DNA, RNA, or a hybrid thereof, including without limitation, cDNA, mRNA, genomic DNA, mitochondrial DNA, sgRNA, siRNA, shRNA, miRNA, tRNA, rRNA, snRNA, lncRNA, and synthetic (such as chemically synthesized) DNA or RNA or hybrids thereof. Nucleic acids can include natural nucleotides (such as A, T/U, C, and G), modified nucleotides, analogs of natural nucleotides, such as labeled nucleotides, or any combination thereof. In some examples, the polynucleotides may DNA. In some examples, the polynucleotides may be RNA.

The diversified molecules may be encoded by one or more open reading frames within the self-diversifying system. In certain cases, the polynucleotide may comprise one or more open reading frames or transcripts thereof. When the polynucleotide comprises multiple open reading frames, the orientations of the open reading frames may be the same.

The self-diversifying system may further comprise one or more additional open reading frames that encode accessory polynucleotides or polypeptides. An accessory polynucleotide or polypeptide may be a polynucleotide or polypeptide that when expressed is involved in processing or generating sequence variants of the diversified molecules. Example accessory polyproteins include, but are not limited to, reverse transcriptases, phage replisome organizers, histone-family DNA-binding proteins, endonuclease, exonucleases, phosphatases, or functional fragments thereof.

The self-diversifying system may further encode one or more regulatory elements such as one or more promoters and/or one or more ribosome binding sites that control expression of the one or more diversified molecules and/or one more accessory polynucleotides or polypeptides.

In some embodiments, the systems and methods allow for generation of diversified molecules with an efficiency at least about 5%, at least about 10%, at least about 20%, at least about 30%, at least about 40%, at least about 50%, at least about 60%, at least about 70%, at least about 80%, at least about 90%, at least about 95%, e.g., as measured by number of diversified molecules in the total number of molecules generated by the self-diversify system.

In certain example embodiments, the self-diversifying system may be based on one or more systems disclosed in SEQ ID NOs: 98-1699, or fragments of the sequences. That is, self-diversifying systems disclosed herein encompass both engineered variants of the example systems disclosed in SEQ ID NOs: 98-1699, or fragments of the sequences, or engineered variants comprising components combined from one or more example systems disclosed in SEQ ID NOs: 98-1699, or fragments of the sequences.

In some examples, such systems may be used for generating universal peptides or protein binders that can be quickly adapted for any given protein targets could replace antibody technology. The production of the diversified molecules may be scalable to allow for generating large repertoires of protein binders, with potential to transform biological research and peptide-based therapeutics, such as antibodies and vaccines.

Diversity Generating Retroelement-Based Systems

In certain example embodiments, the system may comprise one or more components of a diversity generating retroelement (DGR). In certain example embodiments, the self-diversifying system may comprise one or more open reading frames encoding one or more diversified molecules.

The system may further comprise one or more open reading frames encoding an accessory protein. The system may further encode one or more ribosome binding sites. The system may further encode one or more promoters. The diversified molecule and accessory protein open reading frames may be under the control of the same or different open reading frames.

Variable Regions

The one or more diversified proteins and/or their coding polypeptide may comprise one or more variable regions or variable repeats (VR). The variable region dictates one or more locations with the diversified molecule where sequence diversity is generated. The sequence diversity may be generated within the variable region, adjacent to the variable region, or both. The polynucleotide may comprise one or more, e.g., 1, 2, 3, 4, 5, 6, 7, 8, 9, 10, or more variable regions.

The variable region may encode or may be within a coding sequence for a peptide that is capable of binding to another molecule (e.g., proteins, nucleic acids, etc.). Alternatively or additionally, the variable region may encode or may be within a coding sequence for a polynucleotide (e.g., RNA) that is capable of binding to another molecule (e.g., proteins, nucleic acids, etc.).

Template Region

The DGR-based system may further comprise a template region or template repeat (TR). The template repeat may dictate the type and frequency of sequence variants generated within a variable region of the diversified molecules. For example, when transcribed, the template molecule (or cDNA variant thereof) may be integrated into the diversified molecule and certain nucleotides within the template region subject to mutagenesis by the incorporation of the random nucleotides across from certain nucleotides within the template molecule. For example, all adenosines (As) in the template molecule may be subject to mutagenesis by incorporation of random nucleotides opposite the A when the template molecule is integrated into the variable region. Likewise, mutagenesis may occur at T, G, or C nucleotides or at certain nucleotide motifs within the template region. This process may be referred to as mutagenic homing.

The template region may be transcribed into a RNA molecule. The RNA molecule may be reverse transcribed to a population of DNA templates. The reverse transcription may be error prone, e.g., the DNA templates may comprise one or more mutations compared to the original template region. The DNA templates may insert to or replace a sequence the variable region, thus introducing various mutations into the variable region.

The template region may have certain level of homology with the variable region. The term "homology" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference). For example, the homology between the template region and the variable region may be at most 90%, at most 80%, at most 70%, at most 60%, at most 50%, at most 40%, at most 30%, or at most 20%. In certain examples, the homology between the template region and the variable region may be at most 80%.

The template region may comprise one or more adenines. In some cases, the one or more adenines are not found in the variable region. Such adenines may result in mutagenesis or diversification of corresponding positions in the variable region. In certain cases, the template region may comprise one or more insertions of nucleotides (e.g., adenines) compared to the corresponding variable region. In some examples, the template region may comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 nucleotides inserted. The insertion of additional nucleotides may maintain the correct reading frame. As a non-limiting example, groups of three nucleotides (including one or more adenines) may be inserted in-frame into the template region to direct the insertion of a variable codon into the variable region.

In some embodiments, the diversification may be based upon non-adenine substitutions of nucleotides in the template region. For example, a nucleotide in the template region may be substituted with a non-adenine nucleotide such that the substitution is transferred to the corresponding position in variable region. As a non-limiting example, a cytosine (C) to guanine (G) substitution in a template region can be used to result in the same C to G substitution in the variable region. This may be referred to as substitution-mediated diversification.

In some embodiments, a variable region and a template region are comprised of a polynucleotide. The variable region and the template region may be operably linked. An operable linkage between a variable region and a template may refer to the ability of the template region to serve as the template for directional, site-specific mutagenesis or diversification of the sequence in the variable region. Thus in one example embodiment, a recombinant nucleic acid molecule may comprise a template region and a variable region that are physically attached in cis (in the same molecule such as polynucleotide) such that the template region serves as the template sequence to direct site-specific mutagenesis in the variable region. The separation between the template region and variable region may be of any distance so long as they remain operably linked.

In certain embodiments, the template region and variable region may not be linked on the same molecule. In such cases, however, the template region may still have the ability to direct site specific mutagenesis of the variable region. Thus the template region and variable region may be operably linked in trans, such that the sequences of each region are present on separate nucleic acid molecules The variable region (when on a polynucleotide) and template region may be physically and operably linked in cis or operably linked in trans. The separation between the two regions when linked in cis can range from about 100 base pairs to about 2000 base pairs, e.g., from about 100 to 300, from about 200 to about 400, from about 300 to about 500, from about 400 to about 600, from about 500 to about 700, from about 600 to about 800, from about 700 to about 900, from about 800 to about 1000, from about 900 to about 1100, from about 1000 to about 1200, from about 1100 to about 1300, from about 1200 to about 1300, from about 1200 to about 1400, from about 1300 to about 1500, from about 1400 to about 1600, from about 1500 to about 1700, from about 1600 to about 1800, from about 1700 to about 1900, or from about 1800 to about 2000 base pairs.

Regulatory Sequences

The polynucleotide may further comprise one or more regulatory sequences. In some cases, the regulatory sequences may direct the expression of the nucleic acids in specific types. The term "operably linked" as used herein refers to linkage of a regulatory sequence to from a DNA sequence such that the regulatory sequence regulates the mediates transcription of the DNA sequence. Regulatory sequences include transcription control sequences, e.g., sequences which control the initiation, elongation and termination of transcription. In some cases, regulatory sequences include those control transcriptions. Examples of such regulatory sequences include promoters, enhancers, operators, repressor, transcription terminator sequences.

The variable region (or the gene overlapping or including the variable region sequence), the template region, and the coding sequence for reverse transcriptase may be operably linked to the same regulatory sequence (e.g., promoter). Alternatively or additionally, the variable region (or the gene overlapping or including the variable region sequence), the template region, and the coding sequence for reverse transcriptase may be operably linked to different regulatory sequences. In some cases, the variable region (or the gene overlapping or including the variable region sequence) and the template region are operably linked to the same regulatory sequence; and the encoding sequence for reverse transcriptase is operably linked to a different regulatory sequence. In some cases, the template region and the coding sequence for reverse transcriptase are operably linked to the same regulatory sequence; and the variable region (or the gene overlapping or including the variable region sequence) is operably linked to a different regulatory sequence.

Promoters

In some examples, the regulatory sequences are promoters. The promoter may be suitable for expressing the component(s) in the systems, e.g., the variable region, the template region, and/or the reverse transcriptase in desired cells. A promoter refers to a nucleic acid sequence that directs the transcription of a operably linked sequence into mRNA. The promoter or promoter region may provide a recognition site for RNA polymerase and the other factors necessary for proper initiation of transcription when a sequence operably linked to a promoter is controlled or driven by the promoter. A promoter may include at least the Core promoter, e.g., a sequence for initiating transcription. The promoter may further at least the Proximal promoter, e.g., a proximal sequence upstream of the gene that tends to contain primary regulatory elements. The promoter may also include the Distal promoter, e.g., the distal sequence upstream of the gene that may contain additional regulatory elements. In some cases, the promoter may be a heterologous promoter, e.g., promoting expression of nucleic acids or proteins in cells that do not normally make the nucleic acids or proteins.

The promoters may be from about 50 to about 2000 base pairs (bp), from about 100 to about 1000, from about 50 to about 150, from about 100 to about 200, from about 150 to about 250, from about 200 to about 300, from about 250 to about 350, from about 300 to about 400, from about 350 to about 450, from about 400 to about 500, from about 450 to about 550, from about 500 to about 600, from about 550 to about 650, from about 600 to about 700, from about 650 to about 750, from about 700 to about 800, from about 750 to about 850, from about 800 to about 900, from about 850 to about 950, from about 900 to about 1000, from about 950 to about 1050, from about 1000 to about 1100 in length.

The promoters may include sequences that bind to regulatory proteins. In some examples, the regulatory sequences may be sequences that bind to transcription activators. In certain examples, the regulatory sequences may be sequences that bind to transcription repressors.

In some cases, the promoter may be a constitutive promoter, e.g., U6 and H1 promoters, retroviral Rous sarcoma virus (RSV) LTR promoter, cytomegalovirus (CMV) promoter, SV40 promoter, dihydrofolate reductase promoter, β-actin promoter, phosphoglycerol kinase (PGK) promoter, ubiquitin C, U5 snRNA, U7 snRNA, tRNA promoters or EF1α promoter. In certain cases, the promoter may be a tissue-specific promoter may direct expression primarily in a desired tissue of interest, such as muscle, neuron, bone, skin, blood, specific organs (e.g., liver, pancreas), or particular cell types (e.g. lymphocytes). Examples of tissue-specific promoters include lck, myogenin, or thy1 promoters. In some embodiments, the promoter may direct expression in a temporal-dependent manner, such as in a cell-cycle dependent or developmental stage-dependent manner, which may or may not also be tissue or cell-type specific.

In some cases, the promoters may be inducible promoters. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Examples of inducible promoters include, promoters that respond to heavy metals, to thermal shocks, to hormones, promoters that respond to chemical agents, such as glucose, lactose, galactose or antibiotic (e.g., tetracycline or doxycycline). Examples of inducible promoters also include Drug-inducible promoters, for example tetracycline/doxycycline inducible promoters, tamoxifen-inducible promoters, as well as promoters that depend on a recombination event in order to be active, for example the cre-mediated recombination of loxP sites. Examples of inducible promoters further include physically-inducible promoters, e.g., particular a temperature-inducible promoter or a light-inducible promoter.

The promoter may be suitable for expressing the component(s) in the systems, In desired types of cells. In some cases, the promoters are for expressing the component(s) in prokaryotic cells. Examples of such promoters include filamentous haemagglutinin promoter (fhaP), lac promoter, tac promoter, trc promoter, phoA promoter, lacUV5 promoter, and the araBAD promoter. In some cases, the promoters are for expressing the component(s) in eukaryotic cells. Examples of such promoters include the cytomegalovirus (CMV) promoter, human elongation factor-1E promoter, human ubiquitin C (UbC) promoter, and SV40 early promoter. In some examples, the promoters are for expressing the component(s) in yeasts. Examples of such promoters include Gal 11 promoter and Gal 1 promoter. In some cases, the promoters may be used for expressing the components in a cell-free system. In such cases, the promoters may be selected based upon the source of the cellular transcription components, such as RNA polymerase, that are used.

Ribosome Binding Sites

The polynucleotide may comprise one or more ribosome binding sites or sequences encoding one or more ribosome binding sites. A ribosome binding site may be a nucleotide sequence to which the ribosome binds upon the transcribed ribonucleic acid. For example, a ribosome binding site may be the sequence of mRNA at which assembly of the 30S and 50S subunits of the ribosome takes place to initiate translation of an encoded protein. A ribosome binding site may extend from the −20 to the +13 position with respect to the +1 position of the first nucleotide of the initiation codon. The ribosome binding site may comprise a Shine-Dalgarno (SD) sequence. The SD element may act by base pairing with an anti-SD sequence (5'-CCUCCUUA-3') near the 3' end of the 16S rRNA. The ribosome binding site may be a prokaryotic (e.g., *E. coli*) ribosome binding site.

In cases where the polynucleotide comprises a gene with multiple open reading frames, ribosome binding sites may be added in front of one or more (e.g., all) of the open reading frames. In certain cases, the orientations of the open reading frames are identical.

Initiation of Mutagenic Homing

The polynucleotides may comprise one or more initiation of mutagenic homing (IMH) sequences or functional analog thereof. An IMH sequence may functions in determining the direction of the template region to variable region transfer of sequence information. An IMH sequence may also support the use of the corresponding template region IMH-like sequence at the 3' end of the template region to prevent corruption of template region while the IMH directs variability to variable region. Furthermore, in variable region, the 5' boundary of information transfer may be established by the extent of homology between variable region and template region.

The polynucleotides may contain an IMH sequence located at the 3' end of the variable region and an IMH-like sequence at the end of the template region, Alternatively, the polynucleotides may contain an IMH sequence at the end of both the variable region and the template region such that the sequence of the template region may also vary to result in a highly efficient generating system.

In embodiments wherein a sequence of interest (or "desired variable region") to be diversified is not operably linked to the necessary template region, an IMH sequence may be operably located at the 3' of the desired variable region followed by operable linkage to an appropriate template region with its IMH-like 3'-region. A non-limiting example of such a system is seen in the case of a desired variable region which is all or part of a genomic sequence of a cell wherein insertion of an appropriate IMH and introduction of a template region containing construct with the appropriate corresponding IMH-like region, optionally with a cis linked reverse transcriptase coding sequence, is used to diversify the desired variable region. The template region may simply be a direct repeat of the desired variable region sequence to be diversified or mutagenized via the adenines present in the template region.

In certain systems may be engineered to modify the placement of the IMH to direct mutagenic homing to occur at a different position than that dictate by a naturally occurring diversity element. Likewise, the position, size, or sequence composition of the diversity element may be engineered to increase or decrease the rate of mutagenic homing. In certain example embodiments, the diversity generating element is a hairpin loop. In certain example embodiments the hairpin loop is a GC-rich hairpin loop. In certain example embodiments, the DGR-based systems comprise two or more diversity generating elements.

Examples of IMH sequences include those described in Miller J F et al., US20100041033A1, which is incorporated by reference herein in its entirety.

Reverse Transcriptases

The systems herein may further comprise a reverse transcriptase or a coding polynucleotide thereof. A reverse transcriptase refers to an enzyme capable of synthesizing DNA strand (that is, complementary DNA or cDNA) using RNA as a template. In some cases, the reverse transcriptase may have low proof-reading ability. For example, the reverse transcriptase may introduce one or more errors (i.e., nucleotides that are not complementary to the corresponding nucleotides on the template). Examples of reverse transcriptases include the transcriptases from *Vibrio harveyi* ML phage, *Bifidobacterium longum, Bacteroides thetaiotaonicron, Treponema denticola*, cyanobacteria, such as *Trichodesmium* erythrism, the genus *Nostoc*, or *Nostoc punctiforme*.

As used herein, reverse transcriptase may full-length reverse transcriptase or a functional fragment thereof. A functional fragment of a full-length reverse transcriptase may be a polypeptide that is shorter than the full-length reverse transcriptase but has reverse transcriptase activity. For example, a functional fragment of a full-length reverse transcriptase may have at least 50%, at least 60%, at least 70, % at least 80%, at least 90%, at least 95%, at least 99%, or at least 100% of the activity of the corresponding reverse transcriptase. The reverse transcriptase activity may be measured as amount of cDNA generated with certain amount of RNA template.

In some cases, the system may comprise a polynucleotide encoding the reverse transcriptase. In certain examples, the polynucleotide comprising the variable region and/or the template region may comprise a coding sequence for the reverse transcriptase. In some examples, the polynucleotide encoding the reverse transcriptase may be different from the polynucleotide comprising the variable region and/or the template region.

When associated via a cis or trans configuration, expression of the template region and operably linked reverse transcriptase region coding sequence may be under the control of an endogenous or heterologous promoters. When associated in trans, expression of the template region and operably linked reverse transcriptase coding sequences may be under the control of an endogenous or heterologous, regulatable promoter(s).

Figure 10:
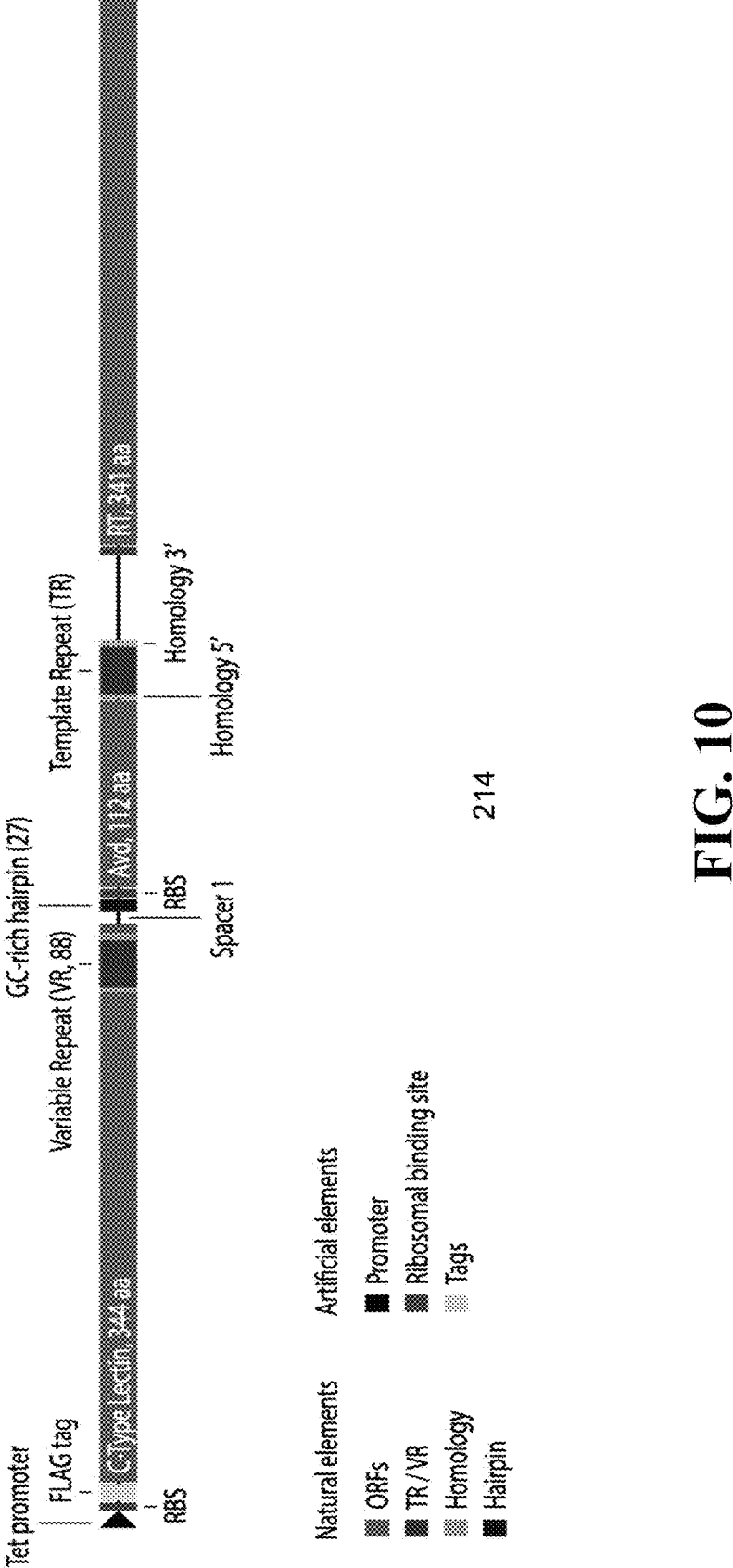
FIG. 10 show an example self-diversifying system (Hit 214).
Figure 16:
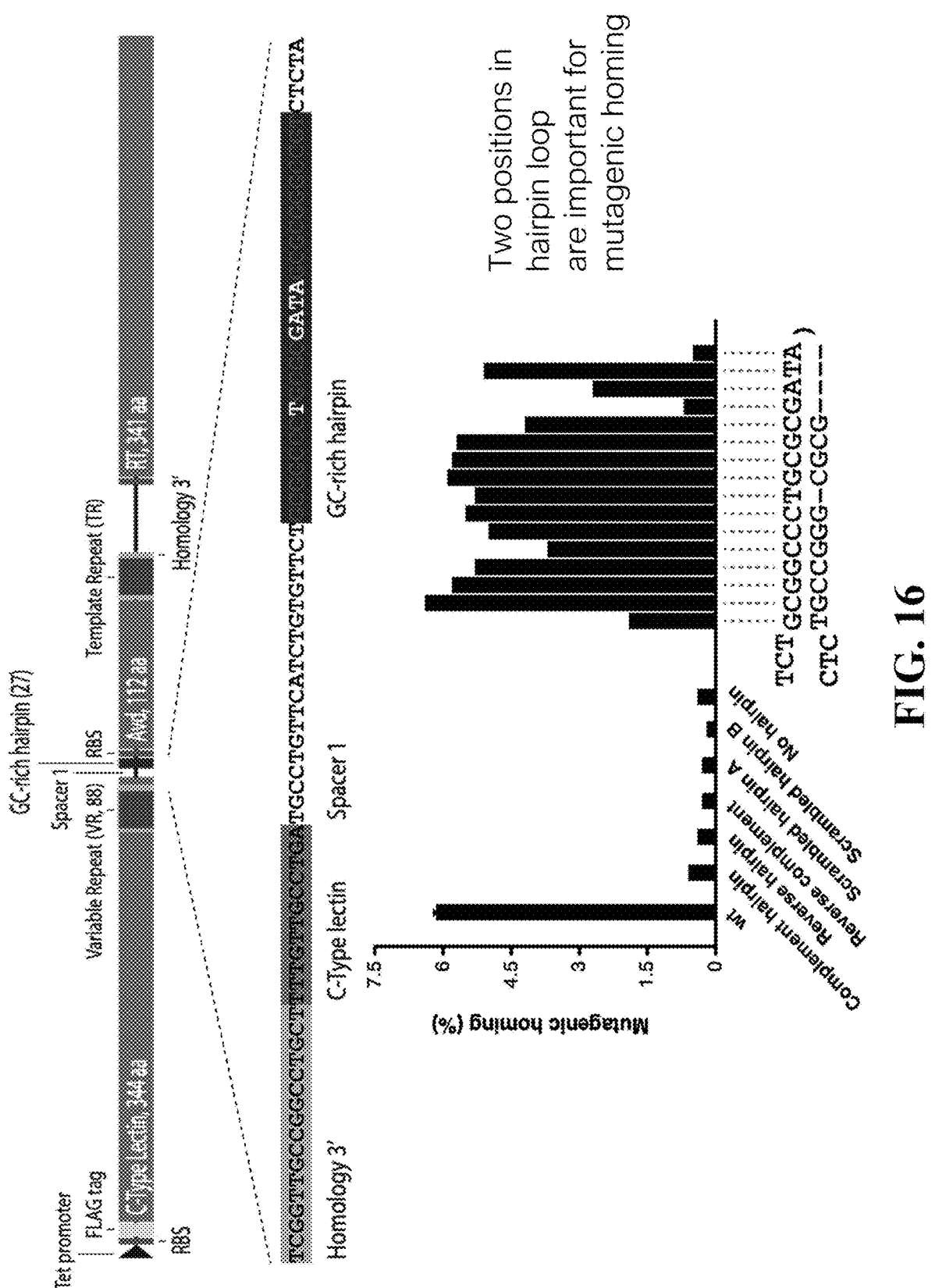
FIG. 16 shows a schematic of Hit 214 and importance of two positions in hairpin loop for mutagenic homing (SEQ ID NOs: 96, 97, and 1700). The sequence of the hairpin loop of Hit 214 is also shown (SEQ ID NO: 97).
Figure 17A:
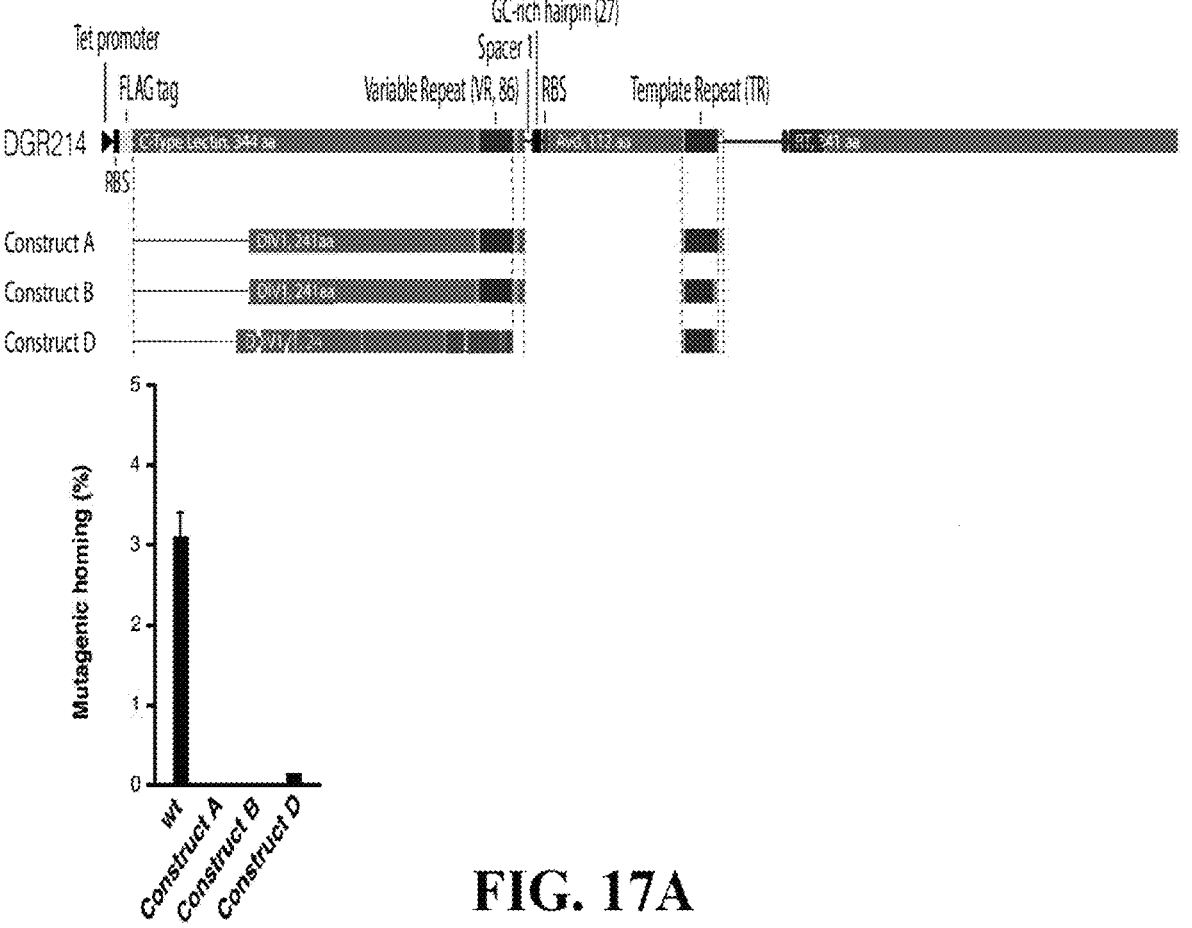
Figure 17C:
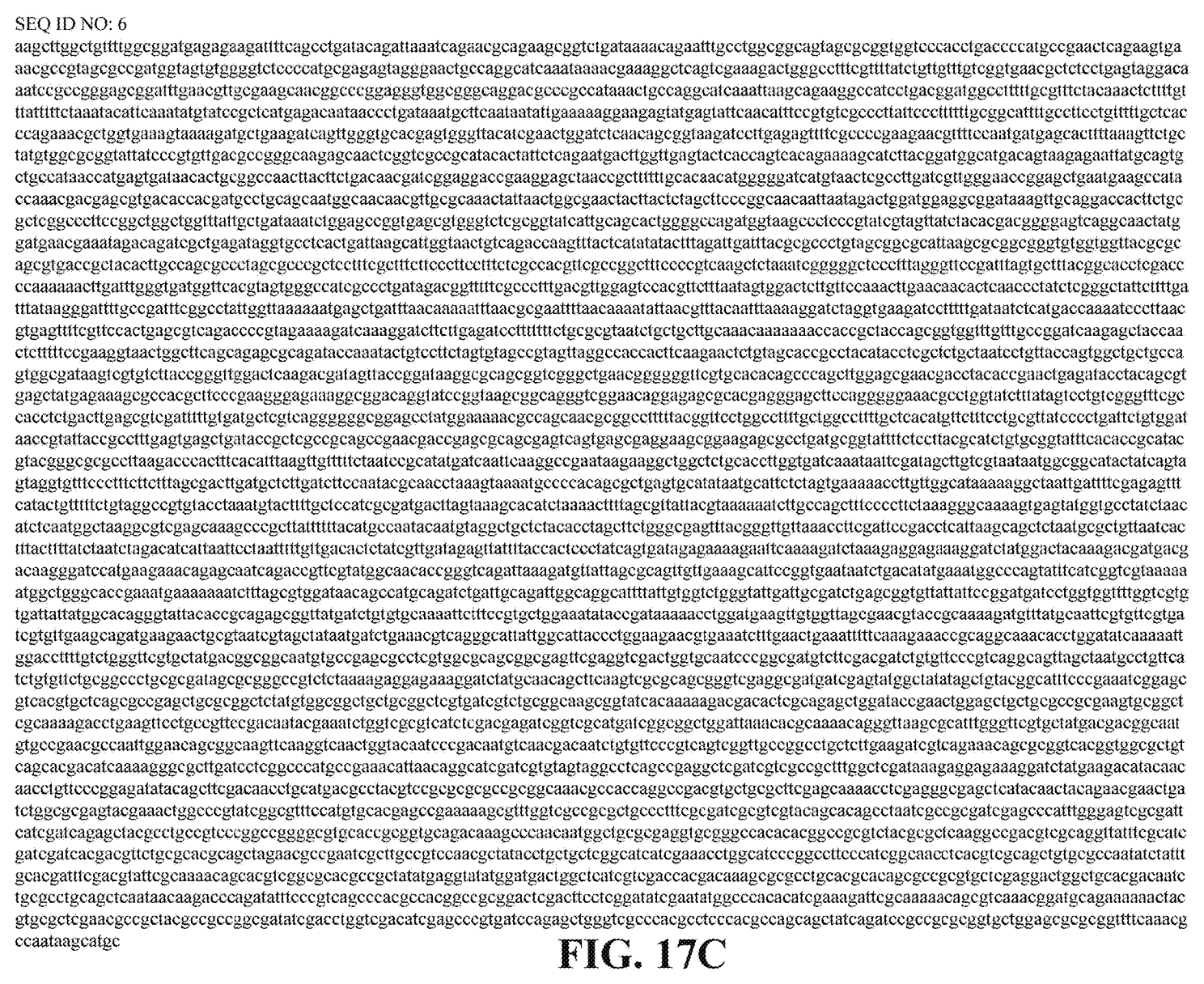

An example DGR system is shown in FIGS. 10 and 16 and further engineered variants thereof shown in FIGS. 17A-17E.

NON-DGR-Based Systems

In certain example embodiments, the self-diversifying system may be a non-DGR system. A non-DGR system may comprise elements capable of generating sequence variants but does not rely on the general structure and element of DGR systems described above. For example, a non-DGR system may comprise one or more self-diversifying elements (e.g. a variable region) but do not comprise a template region or reverse transcriptase. Example non-DGR systems are provided below.

TABLE 1

```
Non-DGR 25          1 GGAGTTATTT CCGGGAACGA CAAACAACCG GAACCCTGAA AAGTAAGAAT CGCATTCAAA
(SEQ ID NO: 1)     61 CTACTTCTAT ATACATGAGC AGTCCCTAAA TTCCCACTCT GCTGCAAATC AACAGCCACT
                  121 TGTTTCATAA ACGAAGTAAA ACTTTCCTTT TTCATTAAAA AATAATTTAA TAATTAATAT
                  181 TTACTAATNN CACAATTTAC TTTAGTAAAA tACGAAAATA TATATACAAA GATTTACATA
                  241 TATAAAATTA TAATATTAAA AACTGAAATA TTCACATTAT CTATCAAATT TATTTTTATA
                  301 CATTTGCGCA GTTTTTTAAA CAAATAATCA TTTTAATTAC TAAAAAACAA CAAAGTTATG
                  361 AACAACAATG AACCAGCTGC CGAACACTAC AGCATCAATG GATTCAAGTA TTTCTCCGAG
```

TABLE 1-continued

```
               421 TTGGCGAAAG AATATTTTCC AGATCTGGCA AACGCCTCTT CCGCCAGCAA AAAAATGCGC
               481 AAACGCATCA AAGCAGACAA GACGTTGAAC GAACAACTGG CTGCCGCGTA TTACACCTGC
               541 CAAACAATCG ACATCAGTCC CGAAATGCAA CTAATCCTTT ACCGCCATTG GGGACCTCCC
               601 CACATCGACC TGCCGACCAA CGTTTAATTA CGTAGTAGAA AACGAAAACA TCGACAAGGA
               661 ATAAAAAGAA AATCGAACTA TATATTTTTA AATATATCAT TTATCTTTTT ATTGTTTATT
               721 ATGTATTCCA CTTTGCGTTC ACCACTTTTT TCGGAAAAGA AGATAACTAT CATTTATACA
               781 GCTATTTACA GAAAgAAAAA AGCGTTCCAC AAAGCGTTCG GCAAAATGAC CGTTTTTTTC
               841 ATTCCAAACA GAGCCTCCGA ATCCTCCCAA CGAAGGCTCT GTTTATCTCC GGCAGAAGtT
               901 CTATCAAACA CAAACAGAGC ATCCGTTTCA TCTCCTGATC GCTTCTTCGC CCCATGAAAG
               961 AAAACAAAAA TACAACAACT TACGTACCAC AACTATTCTT CTTCGTCCAC ACCCGTCCAC
              1021 AAACAGACAC ACCCCTTGCA AACCGCACGG GAATAGCGTA CTTTTACAGA AAATTTAAAT
              1081 AACACTCAAT GAAAAATTTC AATTTTCAAG CCATGCTGAA ACATGGTTTT CTCATTATCC
              1141 CTAAAGCCTT ACTACAGCAG CAGATAGAAG ACCGNCACAT GCAAGAAGGA GAAATAGAAG
              1201 CTCTCCTGAA AATTCTGATG AAGGTCAATT ATTCGGATAC ACTCTACAAC GACCGTCAAA
              1261 ATAAAAACTG CCTGTGTAAA AGAGGCGAAA GCCTGTTTAG TTATCGCGAC TGGAGCCACA
              1321 TCTTCCACTG GTCTGTCGGA AAAGCCTTCA GGTTCATACA CGAGCTTGCC ACGCTGGGAA
              1381 TTATAGAAAT CATCTCTCAC CCCAACAATT CCTCCCTGCA TATTCGTGTC GTCGAATACG
              1441 ATAAATGGAT GGGAGTTCCC GATAGCGACA AGCAGAAAAA GAAAGCCGTC AACGAAAAGT
              1501 TTCACCTGTT CTGGAATGAA TTCCACAGCA TCACACAGCT CCCCAAAGAG AATATCGCCA
              1561 AAGCACAACG CGAATGGAAA AAGTTGGGCG ACAAGGAACA GCAACTCGCC ATCGACAGGA
              1621 TAGAGGAATA TTATTTCCAC CAAACGAACA TCAATTTCCT TCTCCATGCC GCCAGCTATT
              1681 TATCCAACAA AGCTTTTCTT AACGAATACT GATAATATGA ATACCGAAAA CAGAGTTTCG
              1741 CCACAGGCTC CCGAAATAGA AGAAGCTATC ATCGGCGCCT GCCTGATAGA ACAGGGAGCC
              1801 ATACCACTGG TAGCCGACAA GCTGCGTCCC GAAATGTTCT ACGTCCTGCG CCATCAGGTT
              1861 ATCTATGCCG CCATACTGGC CATGTATCAT GCAGGAATAA AGATAGACAT CCTCACCGTA
              1921 AAAGAAGAGC TTTCCCACCG TgGAAAGCTC GAAGAGGCGG GcGGacCGtt CGGcaTCaCC
              1981 CaatTgAgcA gCaAgGtGGc aacCtCCgCC CatNtTGAAT ATCATGCGCA GATCGTACAC
              2041 GAGAAATACC TGCGACGCGA AATGATTCTG GGGTTCAACA AACTCCTCGC CTGTTCGCTA
              2101 GACGAAACGA TGGATATTGA CGACTCACTG GTAGACGCGC ATAAcCTGCT CGACCGTCTG
              2161 GAAGGCGAAT TCGGCCATAA CAACCACATG CGCGACATGG ATGAACTAAT GACCGCCACC
              2221 ATGGTAGAAG CCGAAGGACG TATCGCCAAC AACAAAAACG GAGTAACCGg CCTCCCTACC
              2281 GGACTGGCGG ATCTGGACCG CATgACGTCC GGACTACAGA AAGGCGAGTT GGTGGTGGTC
              2341 GCCGCCCGTC CCGGCGTAGG AAAAACGGCA TTCGCACTAC ACATGGCACG AAGCGCAGCA
              2401 ATGGCAGGGT ATGCCGTAGC TGTCTACAGC CTCGAGATGC AAGGGGAACG ACTAGCAGAC
              2461 CGATGGCTGA CAGCGGTCAG CGAAATCAGC GCCCGCCATT GGCGATCGGG AACCGTCAGC
              2521 CAACAGGAAC TCGTAGAGGC ACGCACAACA GCCGCTGACC TCAAACGCCT GCCGATACAC
              2581 GTAGACGACA GCACATCGGT CAACATGGAA CATATACGTT CCAGCGCGCG ACTGCTGCAA
              2641 AGCCAACATG CGTGCGATGC TATTATTATC GACTACCTGC AACTCTGCGA CATGACGACC
              2701 GGTCAAAACA ACCGCAACCG CGAACAGGAA GTGGCACAAG CNACCCGCAA GGCAAAATTG
              2761 CTAGCCAAAG AACTGAATGT ACCAGTCGTA CTGCTTAGCC AGCTAAACCG CGAATCGGAA
              2821 AACCGCCCTG CCGGCCGTCC CGAACTGGCT CATCTCCGCG AGAGCGGAGC TATTGAACAG
              2881 GATGCAGACG TCGTCATGCT GCTCTACCGT CCCGCCCTTG CAAGGGTGAC GACCGACCGG
              2941 GAAAGTGGTT ATCCCACCGA AGGTCTGGGA GTAGTCATCA TAGCCAAGCA ACGCAACGGA
              3001 GAGACAGGAA ACGTCTATTT CAGACATAAT CCGGAAATGA CCAAGATCAC CGAATATGTC
              3061 CCTCCGTTAG AGTATATGCT GAAACATGCC AAATAAGAAA CAGTTACACT AATAATATAC
              3121 AATTTTATAT TACAACATAT AGCATAAATC ATTTTCTCAT TTTATTTCAT TATCATACA
              3181 ANATATATAG CAAAACACTT GACTTTCCCT CTCATATTTC GTATATTTGT AATGTCGTAA
              3241 GGACAGAGAA AATTTTATTA CTTAAACCTT AACTTTTTAT TGTATGAATG TATTAGTGGA
              3301 GCGCTATCAG CGCAGAAAGT ATGTGAATCA ACCGGATTCA CAGATGTTGT ATTATGTACG
              3361 CCAGAAATCG GGCACAGTGA GAGTGATGGA CATCAACAAG CTGGCGGATG CCATCGAAGC
              3421 GAACTCCTCG CTCACTGCAG GAGACGTGAA GCATGCCATT GAGGCTTTTG TCGAGCAGTT
              3481 ACGCCTATCG CTTACCCAGG GCGACAAGGT GAAGGTTGAC GGATTGGGTA CGTTTCATAT
              3541 CACATTGAGC AGCGAGGGGG CAGAAAAAGA GAAAGATTGC ACGGTGCGCA GCATCCGCAA
              3601 AGTAAATGTC CGTTTCGTGG CGGACAAGGC GCTTCAATTG GTAAATACGA GCCATGCCAC
              3661 TACCCGAGGC GAAAATAATG TCGATTTTAT CCTGgCAGCA AAGGGCGACG GAGAAGGTGA
              3721 CGATGACGGA AATAGCGGNA GCGGTGGAAA CAGCGGCGGA AGCGGAGAAG CTCCGGACCC
              3781 GGCAGCTTAA TCTTTAAAAC AGCGCCGCAT GGATATTACG GAGTGATTTC TACAGTTACT
              3841 CTCNATGCGG TTTCTGTTTT CTTCTACATT TATTTTTTAA TTCTCAATTT TCAATCCTCA
              3901 ATTTATTAAA ATGCTTGATA AAATCATAGA GATCATTATA ACGATCCTGC CCTTTCTGGG
              3961 CAGTAACCGC AAAAAGCGCA AAGTAATGGC GCAAGAAGTA
```

Non-DGR 1057
(SEQ ID NO: 2)
```
                 1 TACGCCGGGC CGTCTGGGAA ACTACATGGA TGACGAAGGC AAGGAAGAGG CAGGCCCCGC
                61 TGCCGGCGCG GCAGGAAACG CAGCGGGCGG GAACAGCCAG CCCGAGCGTA TCATCGCCCT
               121 CCTTGGCGGA CGGGAGAACA TTGAATTTGT GGACGCCTGC ATGACCAGGC TCCGCGTGAC
               181 AGTGAAGGAT CTCTCCAAGG TGGCTGAACT TCCGGCGTGG AAGGCAGAGG GCGCCATGGG
               241 CCTTGTGAAG AAAGACAACG GCATCCAGGC AATTTACGGA CCCAAGGCGG ACGTGCTGAA
               301 ATCGGATATC AAcGATATCC TGTAACAATT CAGCACCCCG GAAAAAATGA GTGAAAATaTG
               361 aaCGGGGAGC CTGCTCACCG GGCAGATTTT GCTCAATAcG CAGAGGAAAG AACTATGAGA
               421 CTGCTTACTA TCAATATTCA CAGCCATGGA AGTGACTTTG AACCGGAACT TTATCATCAG
               481 AAGATGAAGG CGCTGGCGGC ATTTATGAAG GAAGAAGAGA TCGATGCCGC GGCGATCCAG
               541 GAATGCAGTG AAGAGGAGGA CAGGCCGGTG GTCTCCGGCC CCCTCCCCAT GCATTGGGTG
               601 CCGGCCGGAC CGGACTCCCG CGTCCGGGAG GATAACTGTG CGCTGGTCCT GGCGGAGGAA
               661 CTTCAGGGCC TGCAGCAGGA GTACTGGTGG ACCTGGACCG GAGCGAAGCT CGGGTACGGA
               721 AAATACAATG AGGGTCTGGC CATCTTCAGC CGCCGCCCTG TTACAGGCGC GGACAGTTTC
               781 TATATTTCCG GCGTCCGGGA CTTCTCCAAC TGGAAGACCC GGAAGGCGT GGCGGCCTGG
               841 ACCGCTGACG GGCCTGCCTT TTTGAGCGTC CACATGGGAT GGTGGAATGA TCCGGAGGAA
               901 AACTTCCGGG GGCAGATGGA ACGGCTGCAG AAGGCGCTCC GCGAAAGGAA GCTTCGTCCG
               961 CAGGACGGTT CTGACAGTTT CCTTATGGGA GATTTCAACA GTCCCGCAGC GATCCGCGGA
              1021 GAGGGAAGGG ACATGGTCCT GGACCTCGGG TGGCGGGACA GTTATGAGGA TGCCGAAATA
              1081 AAAGACAGCG GCATCACCGT TCCGGGAAAC ATCGACGGAT GGAGGGACGG TGAACATACG
```

TABLE 1-continued

```
1141 GGCATGCGCC TgGATTATAT CTGGACCGCA AAAAGGCACA GGGTGCTTCA GTCAAAGGTG
1201 GTCCTGAACG GGATCAGCGG GCCGGTGCTT TCCGACCATT TCGGAGTCCT GGCGGTGATC
1261 GAATGAATAA AGGAGCAGAC AGCATGAGAG AAAGTGGAAT TCTTCTTGCC ATCAGCAGCC
1321 TTCCTTCCGA ATACGGGATC GGCTGCTTCA GCAGGGAAGC ATATGAGTTT GCGGACCGCC
1381 TTTCAGAGGC GGGCCAGAGT TACTGGCAGA TCCTGCCGCT GGGGCCGGTG GGATACGGAG
1441 ATTCACCGTA CCAGTCCTTC TCCACCTTCG CGGGCAACCC TTACTACATT TCACCTGAGA
1501 CGCTGGTGGA AAAGGGATGG ATCACTGAGG CGGACTGCCG CGAAGCCGGC CTTTCTTCCG
1561 ACCCGCGCGG TGTGGATTAC GTGCTGCAGT ACCAACGCCG CTATGAGCTG CTCCGGAAGG
1621 CGTACAGAAA CAGCCGgATc GAAGAGAATG AGAAGTTCCG GGCGTTCACG GAGAAGACGG
1681 AATGGCTTCC GGACTACGCG CTGTTCATGG CTCTGAAGGA AGAGAACGGA GGAAGGCCCT
1741 GGTACGAATG GGAAGATCCG CTGAGACTCA GGGATCCGGA AGCCTTGGCC GCGGCGCGGG
1801 AACGCCTGGA GGAAGGCATC GGTTTCTGCA GTTTCCTGCA GTTTGAGTTT TaCGAAGAGT
1861 GGATGCAGCT GAAGGACTAC GTGAACCGGA AGGGAATACG GATCATCGGA GACATCCCGA
1921 TCTATGTAtC CCTGGACAGT TCAGACGTCT GGGCGGATCC GGAaCTTttC CNGCTGGAtG
1981 AAAaCCGCCG ACAGaCCGCG GCGGCGGGct GcCCgCCgga tGGcttCagc GCtGtGGGac
2041 aGctctgGGG caaCCCaCTC TATGACTGGG ACTATCACAA AAAGACCTGT TTTGCCTGGT
2101 GGCTGAAACG TCTTAAAAAC TGCTTTGATA TTTATGATGT GATGCGGATC GACCATTTCC
2161 GCGGCTTCGA TGAATATTTT TCCATTCCTG CCGGTGCGGA GGACGCAAGA GCAGGCCATT
2221 GGGAGAAGGG ACCCGGCATG GATCTGTTCC GGAAGGTCTC GGAAGCCTTc CCGGGACGGG
2281 AGATCATCGC GGAGGATCTG GGGTATGTGA CGGACAGTGT CCGGCAGCTG GTGAAGGACA
2341 GCGGCTATCC CGGGATGAAG GTCCTGGAAT TTGCCTTTGA CTCAAGAGAT TCCGGCTGTG
2401 CGGAGGATTA CCTTCCCCAC AATTACGAAA AGAACAGTGT GGTCTACACC GGCACCCATG
2461 ACAACGAGAC GGTGACCGGC TGGTTTTCCG AGGGCCTGAA GCCGGAGGAG AAGGAGGCAG
2521 TCAGAGACTA TTTCTGCGAC CATACGACTC CCGACGCCGG GATGCACATA CCCCTGATCT
2581 GCGCCGCCAT GCGAAGCGTC AGCAGACTCT GCATCATcCC CATGCAGGAC CTTCTGGGGT
2641 ACGGAAACGA GGCAAGGATG AACGCTCCTT CCACCTACGG AAACAACTGG AAATGGCGTC
2701 TTCTGAAGGA TGAATTCGGA GAGAAGGAAG TGAAGACGCT GTATGAgATC ACGAAGCGGT
2761 ACGGAAGGAT CGGAAAATGA GAAAAGAGGA NNGNNNNTNN NNNAANNGNN NNNTACCNNN
2821 NNNNAGNNCA NTNANNNNNT NNNNNNNTNN TTANNNCNNN NCANNGNAAT NATCNNNNNN
2881 NNNNNNNNNNT NTNNNNNNNN NNNNNNNNNN NNNNNNNNNN NCNNNGNTGT NATNNNNNNN
2941 NtNNNNNNCN NNaNCNgNNN tNNGNTNtNN TNNNNNNNNN aNNNtNNNNc NNNagtaNNN
3001 NNNNcNcNtN NNaaNNNNNN NNNaNNNNNN tNNNNNNNNN NNNNNNNNNaN NaNaNNNcNa
3061 aNNNNtNNcN tcgNNNNNNt gNNNNNNNaa tNNgNNNtNN NtNNNNNNNc NNNtNaaNNN
3121 NNtNNttcNN NNNNNNNNNN NNNNNNgNNN NNNNNgNtNa NNNNaaNNNt NtNNaaNNaN
3181 gNNNNaNNNN aNNNNNgNNa NNNNNNNNNN NNNNtNNNNN NNNNaNNNNN NNNNNaNNNN
3241 NNNNNNgNNN NNNNNaNNNN NNNNNNNNNN NNNNNNNNNN NNNNNNNNNN NNNNNNNNNN
3301 NNNNNNNNNN NNNNNNNNNN NNNNNNNNNN NNNNNNNNNN NNNNNNNNNN gNNNNaNNNN
3361 NNNNNNNNNN NNNNNtNNNN tNtNNNNtNN NNNNNNNcNN NNNNNttNtt NNNNNgcNNN
3421 NNNNNNaNNN NNNNNgNNNN NNNNNNNNNN NNNNNNNNNN NNNNNNNNNa NNNNNNNNNN
3481 NNgNNNNNNN NNNNNNagNN NcNNNNNNNN NNNNcNNNcN NNtNNNNNNa NtaNNNNNNN
3541 NNNNNNNNNN NNNNNNNNNN NNNNNNNNNN NNNNNgNNNc NNNNNNNNNt NNNaNNNNNc
3601 NNNNNNNcN NNNNcNNcNN NNNNNcNNNN NNNaNNaNN NcNNNNNNNN NNNNNNNNNN
3661 NNNNNNNNNN tNtNtNNNNN NNNNNNNNNN NNNNNNNNgN NNNNNNNNgN NNNNNNNNaN
3721 gNNNNNNNNN NNNNNNNNNN NNNNNNNNNN NNNNNNNNNN tNNNNNNNNN NNNNNNNNNN
3781 NNNNNNNaNa NNNNNNNNNN NNNNNNNNNN NNNNNNNNNN NNNaNNNNNN NNNNNNNNNN
3841 NNgNNNNNNN NNNNNNNNNN NNNcNNNNNN NNNNNNNNNN NNNNNNNNNN NNNNNNNNNN
3901 NNNNNNNNNN NNNNNNaNNN NNNNNNNNNN NNNNNNNNNN NNNNNNNNNN NNNNtNNNNN
3961 NNNNNNNNNN NNNNNNNNNN NNNNNNgNNN NNNNNNNNNN
```

Vectors

The systems may comprise one or more vectors for delivering the components (e.g., polynucleotides) into cells. For example, the polynucleotides in the systems may be on a vector. A vector refers to a nucleic acid molecule capable of transporting another nucleic acid to which it has been linked. A vector may be a replicon, such as a plasmid, phage, or cosmid, into which another DNA segment may be inserted so as to bring about the replication of the inserted segment. Generally, a vector is capable of replication when associated with the proper control elements. Examples of vectors include nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of poly-nucleotides known in the art. A vector may be a plasmid, e.g., a circular double stranded DNA loop into which additional DNA segments can be inserted, such as by standard molecular cloning techniques.

Certain vectors may be capable of directing the expression of genes to which they are operatively-linked. Such vectors are referred to herein as "expression vectors." Common expression vectors of utility in recombinant DNA techniques are often in the form of plasmids. A vector may be a recombinant expression vector that comprises a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. As used herein, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector may be a viral vector, wherein virally-derived DNA or RNA sequences are present in the vector for packaging into a virus. Viral vectors also include polynucle-otides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some embodiments, the polynucleotide herein may be a part of a vector or a pair of vectors that is/are introduced into cells for inducing diversification (e.g., site-specific mutagenesis) of the variable region and/or support replication of the molecules. Non-limiting examples of vectors include plasmids and virus based vectors, including vectors for phage display that may be used to express a diversified variable region sequence. Other non-limiting embodiments are vectors containing variable sequences that have been subjected to the methods of the instant invention and then removed from an operably linked template region, including by preventing the expression of template regions, so as to produce without further diversification quantities of the variable region-encoded protein for uses including as a diagnostic, prognostic, or therapeutic product.

Methods of Generating Libraries of Diversified Molecules

Provided herein include methods of generating libraries of diversified molecules. In general, the methods comprise introducing one or more components of the system herein in cells, wherein diversified molecules are generated. In some embodiments, a polynucleotide comprising a variable region and a template region is introduced in cells. An RNA molecule may be transcribed from the template region. The RNA molecule may then be reverse transcribed into a population of cDNA molecules. The reverse transcription may be error prone, i.e., the cDNA molecules may comprise one or more mutations compared to the template region in the polynucleotide. Due to the homology between the template region and the variable region, the cDNA molecules may insert to and/or replace a target sequence of the variable region (e.g., the entire variable region). Thus, the mutations in the cDNA molecules may be introduced into the variable region. In some examples, the variable region is within a gene. The gene may be expressed to generate a population of nucleic acids or proteins that carry the mutations. The libraries of diversified molecules may comprise such nucleic acids or proteins with the mutations. The diversified molecules may be proteins or polypeptides. The diversified molecules may be antibodies or fragments thereof. The diversified may be antigens or fragments thereof. The diversified molecules may be nucleic acids or polynucleotides, e.g., DNA, RNA, a hybrid thereof.

The systems and the methods herein may allow for generating libraries of diversified molecules with high efficiency. The efficiency refers to number of diversified molecules generated relative in the total number of molecules generated by a given self-diversifying system. In some embodiments, the efficiency of diversified molecules generation is at least at least 5%, at least 10%, at least 20%, at least 30%, at least 40%, at least 50%, at least 60%, at least 70%, at least 80%, at least 90%, or at least 95%.

A library ("population") of diversified molecules may comprise a plurality of unique sequence variants. For example, a library of diversified molecules may comprise at least $1 \times 10^8$, at least $2 \times 10^8$, at least $4 \times 10^8$, at least $6 \times 10^8$, at least $8 \times 10^8$, at least $1 \times 10^9$, at least $2 \times 10^9$, at least $4 \times 10^9$, at least $6 \times 10^9$, at least $8 \times 10^{10}$, at least $1 \times 10^{11}$, at least $2 \times 10^{11}$, at least $4 \times 10^{11}$, at least $6 \times 10^{11}$, at least $8 \times 10^{11}$, at least $1 \times 10^{12}$, at least $2 \times 10^{12}$, at least $4 \times 10^{12}$, at least $6 \times 10^{12}$, at least $8 \times 10^{12}$, at least $1 \times 10^{13}$, at least $2 \times 10^{13}$, at least $4 \times 10^{13}$, at least $6 \times 10^{13}$, at least $8 \times 10^{13}$, or at least $1 \times 10^{14}$ different molecules.

Diversified Molecules

Embodiments disclosed herein further encompass diversified molecules generated using the self-diversifying systems disclosed herein. In certain example embodiments, the diversified molecule is a polynucleotide-binding protein or a polypeptide-binding protein. Such proteins may be engineered to bind target polynucleotides in a sequence specific manner.

The variable region may be within an open reading frame of the gene. In some examples, the sequence may encode DIV1 or DIV18.

Examples of DIV1 and DIV18 are proteins in Table 2 below (SEQ ID NO: 3 and SEQ ID NO: 4).

TABLE 2

| DIV1 | MKKQSNQTVRMATPGQIKDVISAVVESIPVNNLTYEMAQYF<br>IGRKKWLGTEMKKIFSVDNSHADLIADWQAFYCGLGIDCDL<br>SGVIIPDDPGGFGRVIIMAQGITPQSGYDLCAKFFPCWKYT<br>DKNLDEVVVSERTAKDVYAIRVRDRVEADEELRNRSYNDLK<br>RQGIIGITLEEREIFELKFFKETAGKHLDIKNWTFCLGSCY<br>DGGNVPSASWRSGEFEVDWCNPGDVFDDLCSRQAVS |
|------|------|
| DIV18 | MRTFEITEKEVAAAFREAESGEAKKILAALFCKEEMVKPTL<br>DDYKTIRTYEDACKALGEPIFEDPNNLPNHIIALMKLETIS<br>RALWGRNFQPKPDGEGSKVYWYPWFALWTKKEVEDMNPEQR<br>GALVSANADLGAFAGFGCLAALYRSSSADAGIGFRLCQETE<br>EKAKYFGQQFIELWAEYLKFNFTVGNRL |

Examples of DIV1 and DIV18 also include the orthologs and homologs of the proteins in Table 1. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22 (4): 359-66. doi: 10.1002/pro.2225.). See also Shmakov et al. (2015) for application in the field of CRISPR-Cas loci. Homologous proteins may but need not be structurally related, or are only partially structurally related.

Binding Partners and Target Molecules

The diversified molecules may comprise binding partners of a target molecule. Target molecules may be any molecules which is of interest to a skilled person practicing the invention. Examples of target molecules include polypeptides, cell surface molecules, carbohydrates, lipids, hormones, growth or differentiation factors, cellular receptors, a ligand of a receptor, bacterial proteins or surface components, cell wall molecules, viral particles, immunity or immune tolerance factors, MHC molecules (such as Class I or II), tumor antigens found in or on tumor cells, and others as desired by a skilled practitioner and/or described herein.

The binding partners (e.g., encoded at least in part by the variable regions) may be any polypeptide which, upon expression, binds to the target molecule, such as under physiological conditions or laboratory (in vivo, in vitro, or in culture) conditions. In some cases, the binding partners may be nucleic acids. In certain examples, the binding partner may be aptamers or derivatives thereof.

Libraries of binding partners of various types may be generated using the systems and methods herein. Examples of binding partners include antibodies (e.g., antibodies (Ab) and monoclonal antibodies (MAb)), antigens, hormones, receptor proteins, ligands to receptors, amylin, THF-γ2, adrenomedullin, insulin, VEGF, PDGF, echistatin, human growth hormone, MMP, fibronectin, integrins, calmodulin, selectins, HBV proteins, HBV antigens, HBV core antigens, tryptases, proteases, mast cell protease, Src, Lyn, cyclin D, cyclin D kinase (Cdk), p16$^{INK4}$, SH2/SH3 domains, SH3 antagonists, ras effector domain, farnesyl transferase, p21$^{WAF}$, Mdm2, vinculin, components of complement, C3b, C4 binding protein (C4BP), receptors, urokinase receptor, tumor necrosis factor (TNF), TNFα receptor, CTLA4 MAb, interleukins, IL-1, IL-2, IL-3, IL-4, IL-5, IL-6, IL-7, IL-8, IL-9, IL-10, IL-1, IL-12, IL-13, IL-17, interferons, LIF, OSM, CNTF, GCSF, interleukin receptors, IL-1 receptor, c-MpI, erythropoietin (EPO), the EPO receptor, T cell receptor, CD4 receptor, B cell receptor, CD30-L, CD40L, CD27L, leptin, CTLA-4, PF-4, SDF-1, M-CSF, FGF, EGF. In some examples, the binding partner may be a bacteriocin (including a vibriocin, pyocin, or colicin), a bacteriophage protein (including a tail component that determines host specificity), capsid or surface membrane component, a ligand for a cell surface factor or an identified drug or diagnostic target molecule. In some examples, a binding partner may be part of a fusion protein such that it is produced as a chimeric protein comprising another polypeptide. Examples of the other polypeptide member of the fusion protein may include bacteriophage tail fibers, toxins, neurotoxins, antibodies, growth factors, chemokines, cytokines, neural growth factors.

In some cases, libraries of diversified molecules may also include barcodes (e.g., for connectomics analysis). The libraries of diversified molecules may include enzymes, antibodies, nanobodies, non-coding RNAs, barcode sequences, regulatory sequences (e.g., enhancers, promoters).

Delivery of Diversifying Systems to Cells

The one or more components of the systems herein may be introduced to cells for expression. Examples of methods of introducing the components into cell include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). Physical methods of introducing polynucleotides may also be used. Examples of such methods include injection of a solution containing the polynucleotides, bombardment by particles covered by the polynucleotides, soaking a cell, tissue sample or organism in a solution of the polynucleotides, or electroporation of cell membranes in the presence of the polynucleotides. Examples of delivery methods and vehicles include viruses, nanoparticles, exosomes, nanoclews, liposomes, lipids (e.g., LNPs), supercharged proteins, cell permeabilizing peptides, and implantable devices. The nucleic acids, proteins and other molecules, as well as cells described herein may be delivered to cells, tissues, organs, or subjects using methods described in paragraphs to of Feng Zhang et al., (WO2016106236A1), which is incorporated by reference herein in its entirety.

Host Cells

In some cases, the cells where the diversified molecules are generated are bacterial cells. The cells may be bacteria, archaea, yeasts, fungi, protists, plant cells and animal cells. For example, the cells may be microorganisms, e.g., bacteria, archaea, fungi, protozoans, *mycoplasma*, and parasitic organisms. In a particular example, the cells are *E. coli*.

In some examples, the cells may be bacteria. The terms "bacteria" and "bacterium" refer to all prokaryotic organisms, including those within all of the phyla in the kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms which are gram negative or gram positive. In certain examples, the cells may be fungi. As used herein, the term "fungi" is used in reference to eukaryotic organisms such as the molds and yeasts, including dimorphic fungi.

In some cases, the cells are *E. coli*. The cells may be of specific strain of *E. coli*. In some cases, the cells are not NEB5α or stb13 bacteria.

Genetically Modified Cells

The cells used herein may be genetically modified. The genetic modification may allow for highly efficient generation of diversified molecules. The genetic modification may include reduction or depletion of expression of one or more genes in the cells (e.g., *E. coli* cells). In some examples, the expression of mutator S is reduced or depleted in the cells (e.g., *E. coli* cells). In some cases, the expression of Exodeoxyribonuclease 10 is reduced or depleted in the cells (e.g., *E. coli* cells). In some cases, the expression of both mutator S and Exodeoxyribonuclease 10 is reduced or depleted in the cells. In certain cases, the cells used herein may be wild type cells.

Methods of Screening Binding Partners for a Target Protein

The present disclosure also provides methods for screening binding partners for a target molecule. The binding partners may be screened from one or more libraries of diversified molecules generated using the methods and systems herein. In some cases, the method of screening binding partners of a target molecule, comprising obtaining of a library of diversified molecules using the system herein, performing one or more assays to determine interaction between the diversified molecules and the target molecule; and selecting a subset of the diversified molecules based on results of the one or more assays.

One or more assays may be performed for testing the interaction between candidate binding partners and the target molecule. Examples of the assays include phage display, toxin inhibition assay, toxin survival assay, bacterial surface display, bacterial two-hybrid display assay, bacterial three-hybrid display, yeast two-hybrid assay, yeast three-hybrid assay, an enzyme-linked immunosorbent assay (ELISA), immunoprecipitation assay, or a combination thereof.

In certain examples, the assay may be phage display. Phage display may be the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

With the assay(s), affinity between the candidate binding partners and the target molecule may be determined. Binding partners with desired affinity (e.g., those with highest affinity) with the target molecule may be selected.

Methods of Identifying Diversity Generation Systems

The present disclosure also provides methods for identifying diversity-generating systems herein. In general, the methods may comprise identifying loci with higher diversity in contigs larger than 1 kb in a database, compared to average diversity in the sequences in the database.

For example, the database may be a metagenome database. As used herein, the term "metagenome" refers to genomic material obtained directly from a microbe or microbial population, instead of from culture. A metagenome database includes sequence information of metagenome.

The term "contig" is used in connection with DNA sequence analysis, and refers to reassembled contiguous stretches of DNA derived from two or more DNA fragments having contiguous nucleotide sequences. Thus, a contig may be a set of overlapping DNA fragments that provides a (partial) contiguous sequence of a genomic region of interest. A contig may also be a set of DNA fragments that, when aligned to a reference sequence, may form a contiguous nucleotide sequence. For example, the term "contig" encompasses a series of (ligated) DNA fragment(s) which are ordered in such a way as to have sequence overlap of each (ligated) DNA fragment(s) with at least one of its neighbors. The linked or coupled (ligated) DNA fragment(s), may be ordered either manually or, preferably, using appropriate computer programs such as FPC, PHRAP, CAP3 etc., and may also be grouped into separate contigs.

The contigs in the methods herein may be at least 0.5 kilobase (kb), at least 1 kb, at least 1.5 kb, at least 2 kb, at least 2.5 kb, at least 3 kb, at least 3.5 kb, or at least 4 kb in length. In some examples, the contigs may be at least 3 kb in size.

The contigs comprising the identified loci may then be selected. In some cases, the selected contigs encode a polypeptide of at least 50, at least 60, at least 70, at least 80, at least 90, at least 100, at least 120, at least 140, at least 160, at least 180, or at least 200 amino acids in length.

The methods may further comprise confirming whether the system is able to generate diversified molecules in cells. The presence of diversified molecules in the cells may be determined by sequencing. Generally, the sequencing can be performed using automated Sanger sequencing (AB13730xl genome analyzer), pyrosequencing on a solid support (454 sequencing, Roche), sequencing-by-synthesis with reversible terminations (ILLUMINA® Genome Analyzer), sequencing-by-ligation (ABI SOLID®) or sequencing-by-synthesis with virtual terminators (HELISCOPE®); Moleculo sequencing (see Voskoboynik et al. eLife 2013 2: e00569 and U.S. patent application Ser. No. 13/608,778, filed Sep. 10, 2012); DNA nanoball sequencing; Single molecule real time (SMRT) sequencing; Nanopore DNA sequencing; Sequencing by hybridization; Sequencing with mass spectrometry; and Microfluidic Sanger sequencing. Examples of information that can be obtained from the disclosed methods and the analysis of the results thereof, include without limitation uni- or multiplex, 3 dimensional genome mapping, genome assembly, one dimensional genome mapping, the use of single nucleotide polymorphisms to phase genome maps, for example to determine the patterns of chromosome inactivation, such as for analysis of genomic imprinting, the use of specific junctions to determine karyotypes, including but not limited to chromosome number alterations (such as unisomies, uniparental disomies, and trisomies), translocations, inversions, duplications, deletions and other chromosomal rearrangements, the use of specific junctions correlated with disease to aid in diagnosis. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. In certain cases, the primers used may contain a molecular barcode (an "index") so that different pools can be pooled together before sequencing, and the sequence reads can be traced to a particular sample using the barcode sequence.

The present application also provides aspects and embodiments as set forth in the following numbered Statements:

Statement 1. A self-diversifying system, comprising a polynucleotide encoding one or more open reading frames, at least one open reading frame comprising a diversifying element, the diversifying element resulting in generation of diversified molecules from the polynucleotide, wherein the system is configured to generate a population of diversified molecules with an efficiency of at least 80% as measured by a number of diversified molecules in a population relative to the total number of molecules generated in the population.

Statement 2. The system of Statement 1, wherein the self-diversifying element comprises a template region and/or a variable region.

Statement 3. The system of Statement 1 or 2, wherein the self-diversifying system is a diversity generating retroelement (DGR) system.

Statement 4. The system of any one of the proceeding Statements, wherein the self-diversifying system is a non-DGR system.

Statement 5. The system of any one of the proceeding Statements, further comprising a reverse transcriptase or functional domain thereof.

Statement 6. The system of any one of the proceeding Statements, wherein the polynucleotide comprises a sequence selected from SEQ ID NOs. 98-1699.

Statement 7. The system of any one of the proceeding Statements, wherein the sequence encodes c-type lectin fold or a fragment thereof.

Statement 8. The system of any one of the proceeding Statements, wherein the sequence encodes a protein or polypeptide capable of binding to a protein or a nucleic acid.

Statement 9. The system of any one of the proceeding Statements, wherein the variable region and the template region have a sequence homology of less than 80%.

Statement 10. The system any one of the proceeding Statements, wherein the polynucleotide further comprises a regulatory sequence.

Statement 11. The system of Statement 10, wherein the regulatory sequence comprises one or more ribosomal binding sites.

Statement 12. The system of Statement 10 or 11, wherein the regulatory sequence comprises an inducible promoter.

Statement 13. The system of any one of the proceeding Statements, wherein the diversified molecules are proteins.

Statement 14. The system of any one of the proceeding Statements, wherein the diversified molecules are polynucleotides.

Statement 15. The system of any one of the proceeding Statements, wherein the sequence encodes DIV1 or a fragment thereof.

Statement 16. The system of any one of the proceeding Statements, wherein the sequence encodes DIV18 or a fragment thereof.

Statement 17. The system of any one of the proceeding Statements, wherein the sequence is from Table 1 or the sequence encodes a protein from Table 2.

Statement 18. The system of any one of the proceeding Statements, wherein the diversified molecules comprise one or more binding partners of a target molecule.

Statement 19. The system of Statement 18, wherein the target molecule is a protein.

Statement 20. The system of any one of Statements 18-19, wherein the target molecule is an antigen.

Statement 21. The system of any one of Statements 18-20, wherein the target molecule is a polynucleotide.

Statement 22. The system of any one of the proceeding Statements, wherein the system generates the library of diversified molecules when introduced to cells.

Statement 23. The system of any one of the proceeding Statements, wherein the variable region is within an open reading frame.

Statement 24. The system of any one of the proceeding Statements, wherein the system comprises a vector comprising the polynucleotide.

Statement 25. The system of any one of the proceeding Statements, wherein the system comprises a vector comprising the polynucleotide and a nucleic acid sequence encoding the reverse transcriptase.

Statement 26. The system of any one of the proceeding Statements, wherein the reverse transcriptase is error prone.

Statement 27. A method of generating a library of diversified molecules, comprising introducing the system of any one of Statements 1 to 26 in cells, wherein the system generates the library of diversified molecules in the cells.

Statement 28. The method of Statement 27, wherein the method generates the library of diversified molecules with an efficiency of 80%.

Statement 29. The method of Statement 27 or 28, wherein the cells are *E. coli* cells.

Statement 30. The method of Statement 27, 28, or 29, wherein expression of Mutator S and/or Exodeoxyribonuclease 10 are reduced or depleted in the cells.

Statement 31. A method of identifying a diversity-generating system, comprising: identifying loci with higher diversity in contigs larger than 1 kb in a database; selecting contigs comprising the identified loci in a), wherein each selected contig comprises a sequence encoding a polypeptide of least 100 amino acids; and expressing polynucleotides comprising at least a portion of the polypeptide-encoding sequence in the selected contigs from b) in cells, thereby confirming self-diversifying function of the polynucleotides.

Statement 32. The method of Statement 31, wherein the database is a metagenome database.

Statement 33. The method of Statement 31 or 32, wherein the contigs in a) are larger than 3 kb.

Statement 34. A method of screening binding partners of a target molecule, comprising: obtaining a library of diversified molecules using the system of any one of Statements 1 to 26, performing one or more assays to determine interaction between the diversified molecules and the target molecule; and selecting a subset of the diversified molecules based on results of the one or more assays.

Statement 35. The method of Statement 34, wherein the one or more assay comprise phage display, toxin inhibition assay, toxin survival assay, bacterial surface display, bacterial two-hybrid display assay, an enzyme-linked immunosorbent assay (ELISA), immunoprecipitation assay, or a combination thereof.

Statement 36. The method of Statement 34 or 35, wherein the target molecule is an antigen.

EXAMPLES

Example 1

Bacteria actively diversify endogenous proteins to adapt changing environment. This examples demonstrate an exemplary approach to use the diversification mechanism to generate protein binders at large scale.

Figure 2:
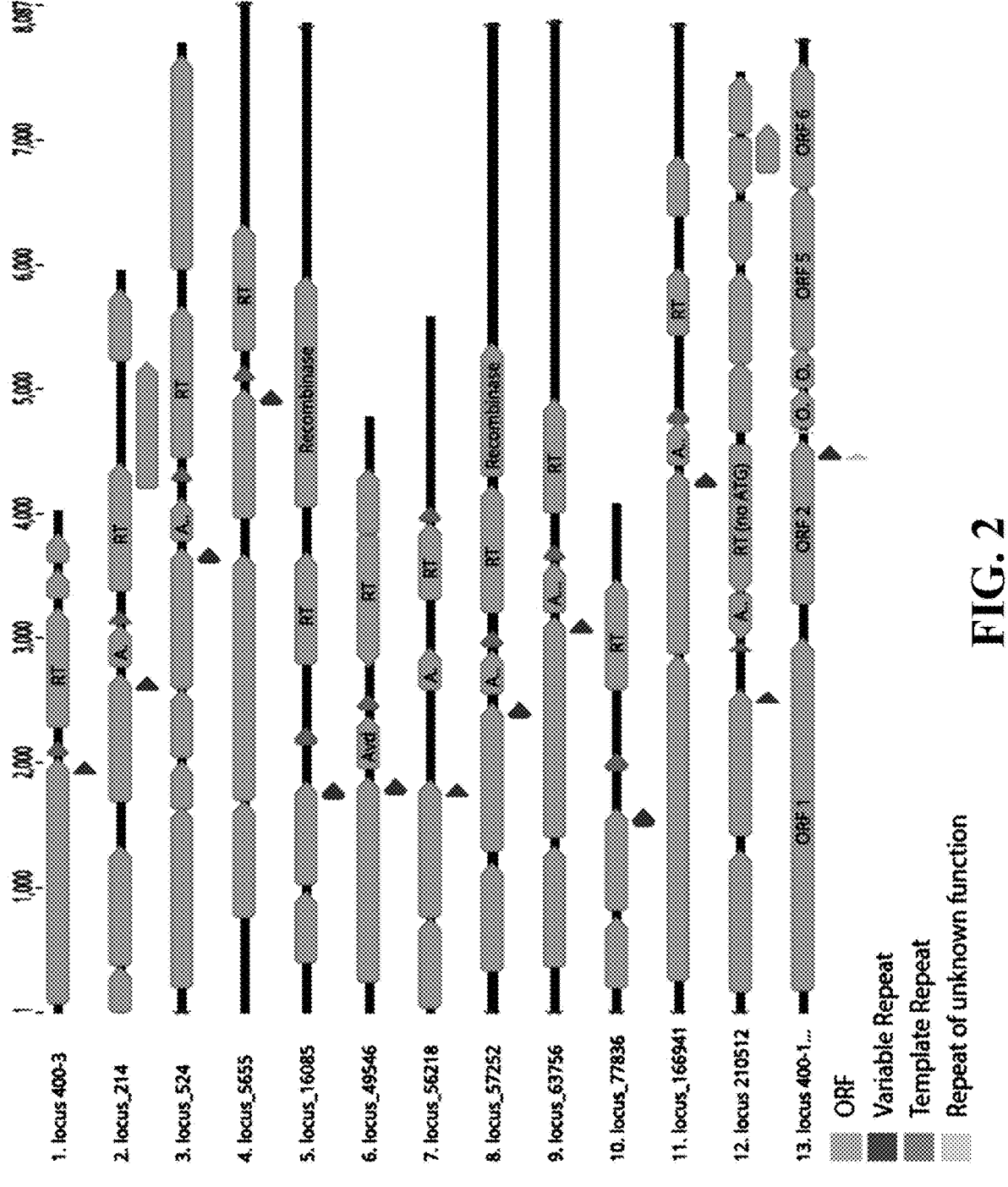
FIG. 2 shows selected candidate diversity-generating systems.
Figure 3:
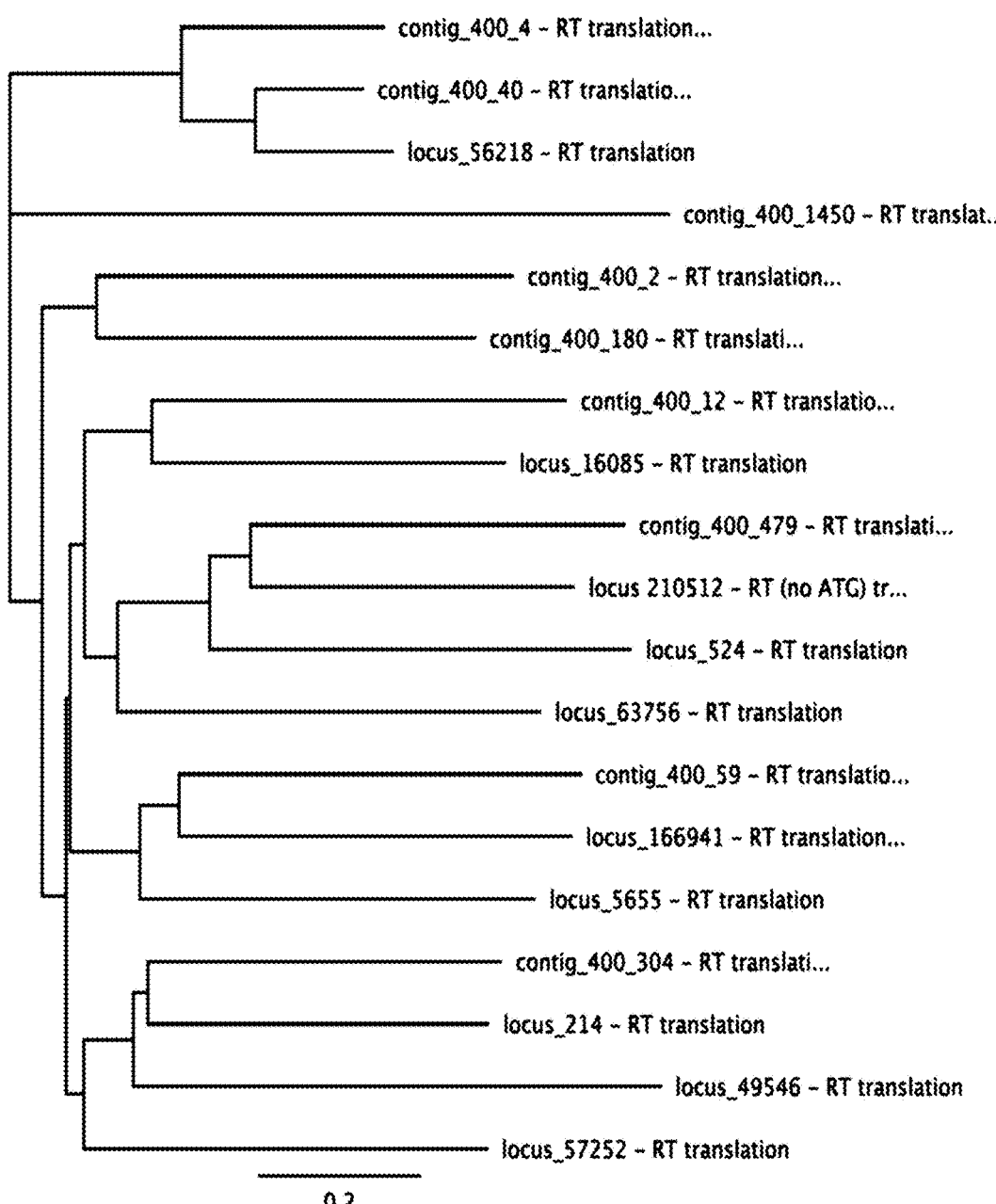
FIG. 3 shows diversity of reverse transcriptases in the candidate diversity-generating systems.

In general, edges of low-high-low diversity in DNA sequences in metagenome database of *E. coli* were found. All contigs larger than 3 kb in public JGI metagenome database for edges of low-high-low diversity regions. A algorithm and a computer with (800 GB of RAM) were used for the scan. Overlapping protein-coding sequences of at least 100 amino acid residues were filtered, and approximately 200 potential hits were found. Many of the hits had reverse transcriptase coding sequences and a template regions similar sequences to known classes of diversity-generating retroelements (DGRs) (FIGS. 1A-1D). A subset of the identified hits were selected for further analysis (FIG. 2). The reverse transcriptase in these hits showed diversity (FIG. 3)

Figure 4A:
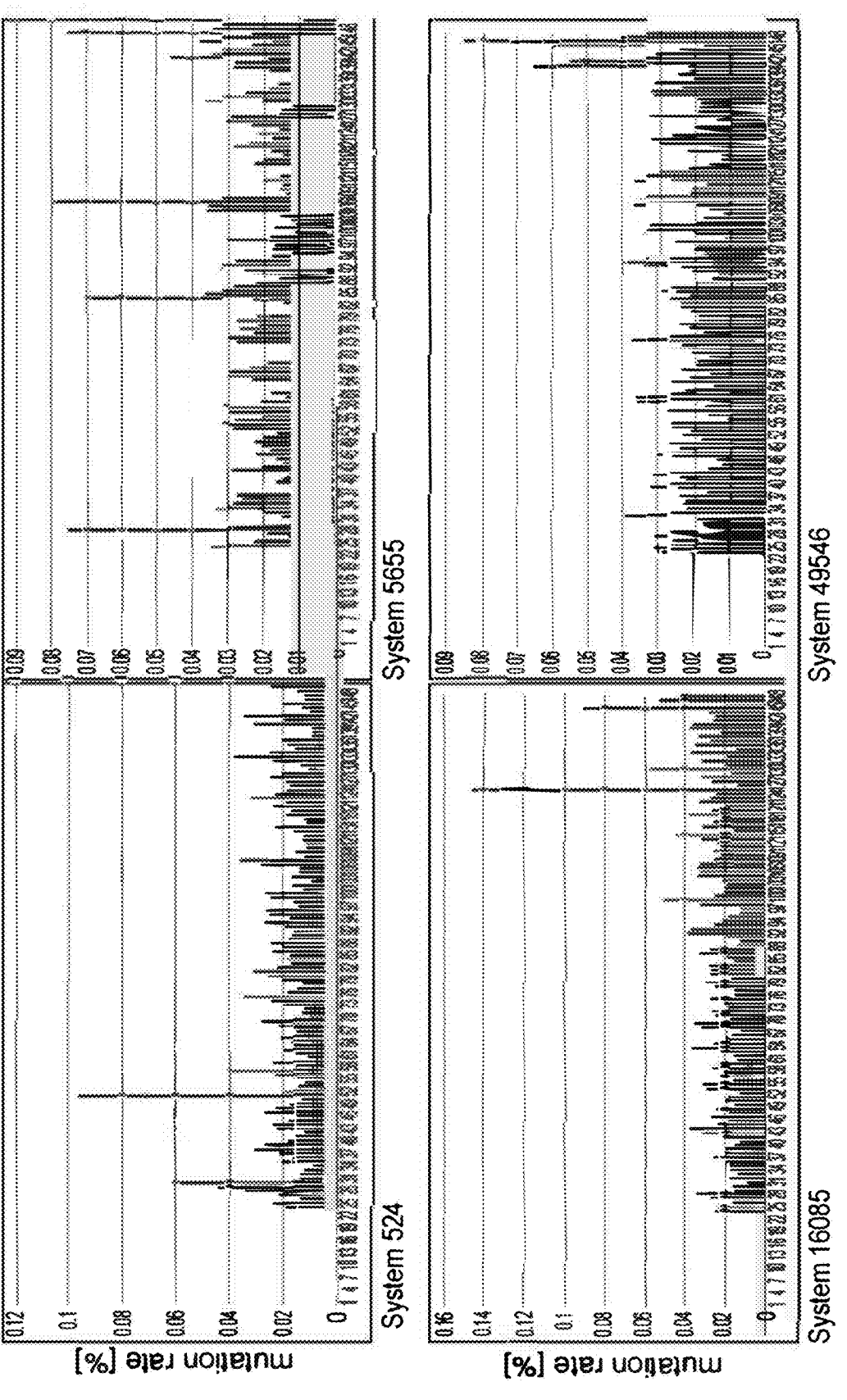
FIGS. 4A and 4B show results from testing the selected candidate diversity-generating systems of FIG. 2.
Figure 4B:
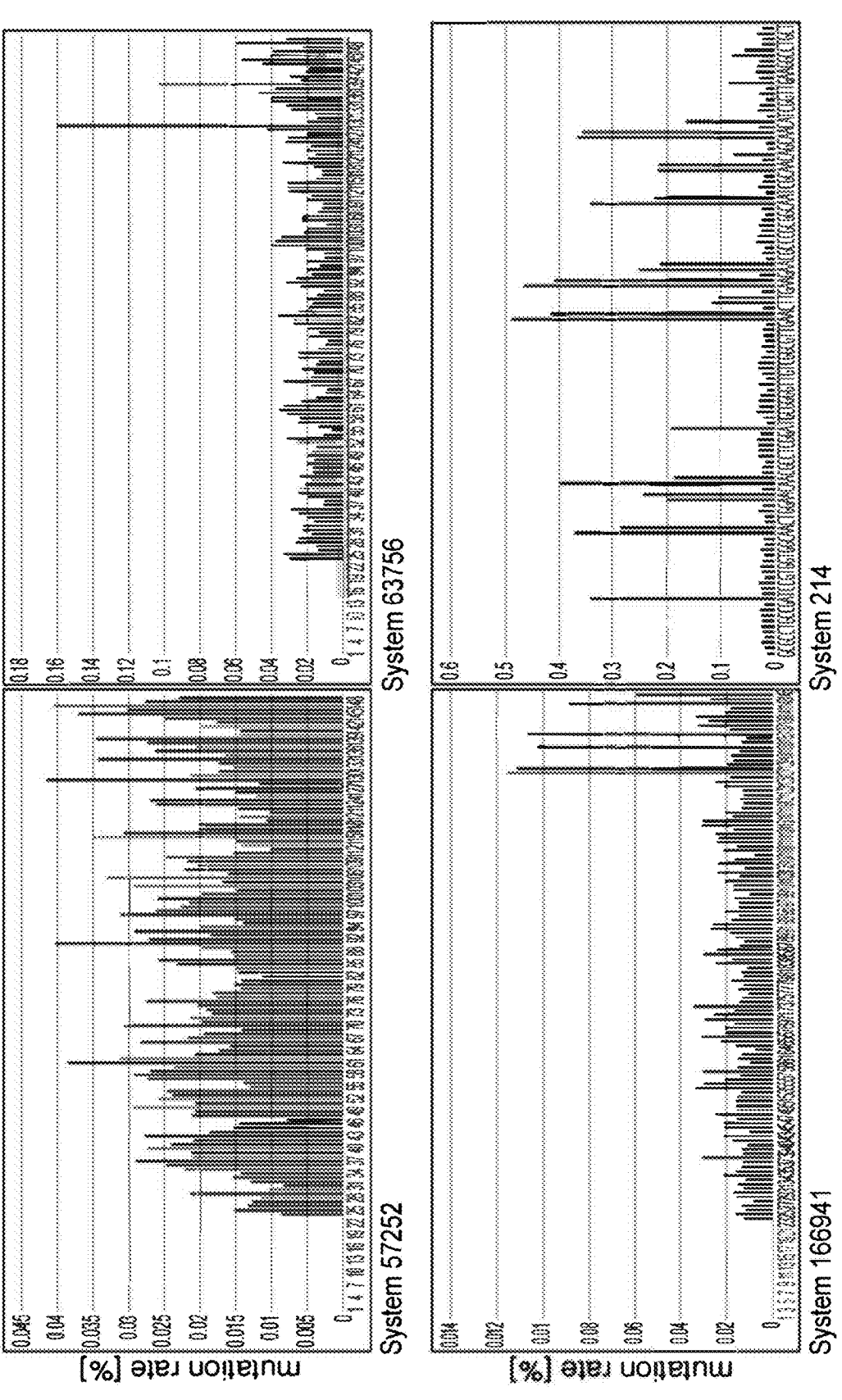
Figure 5B:
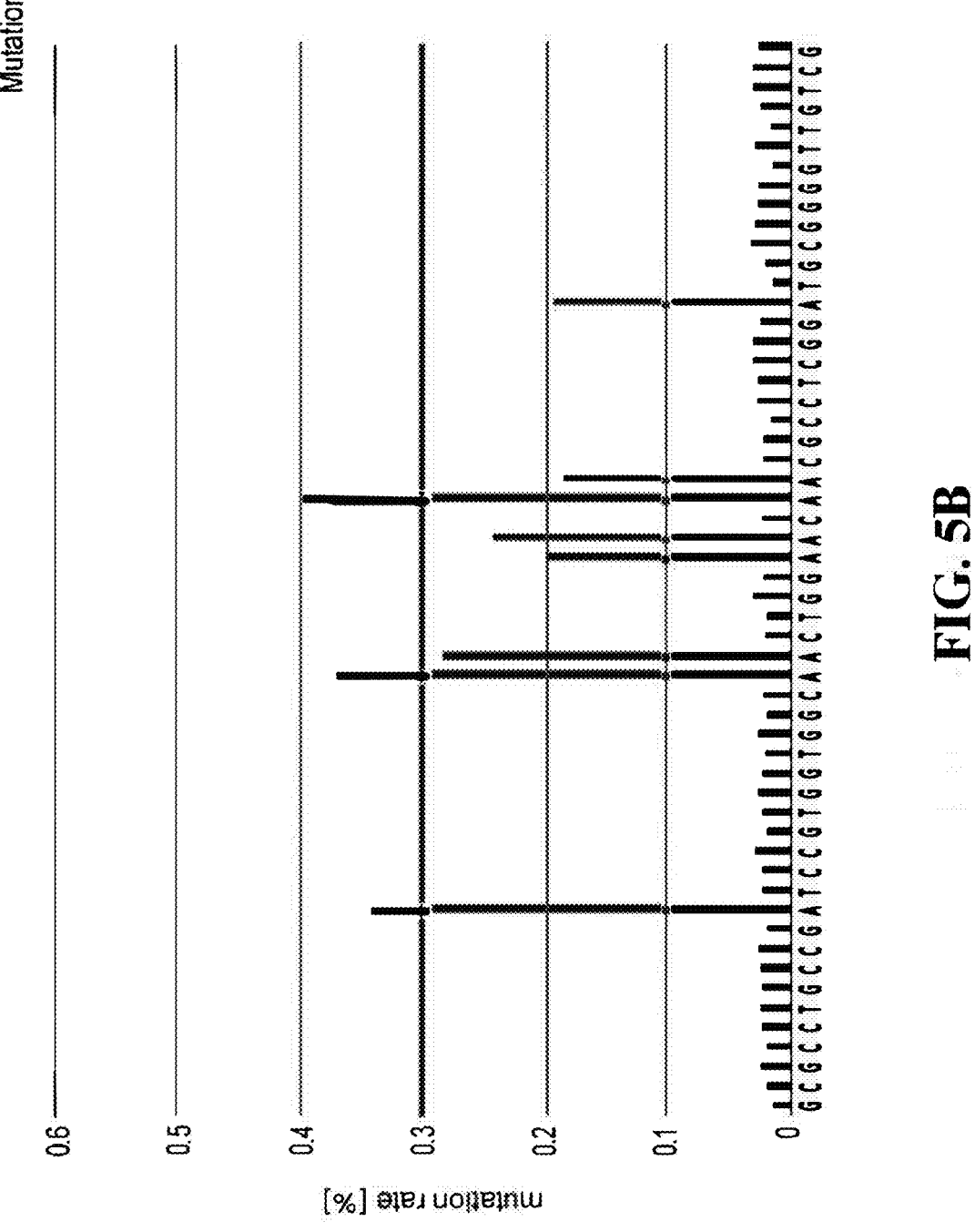
Figure 6C:
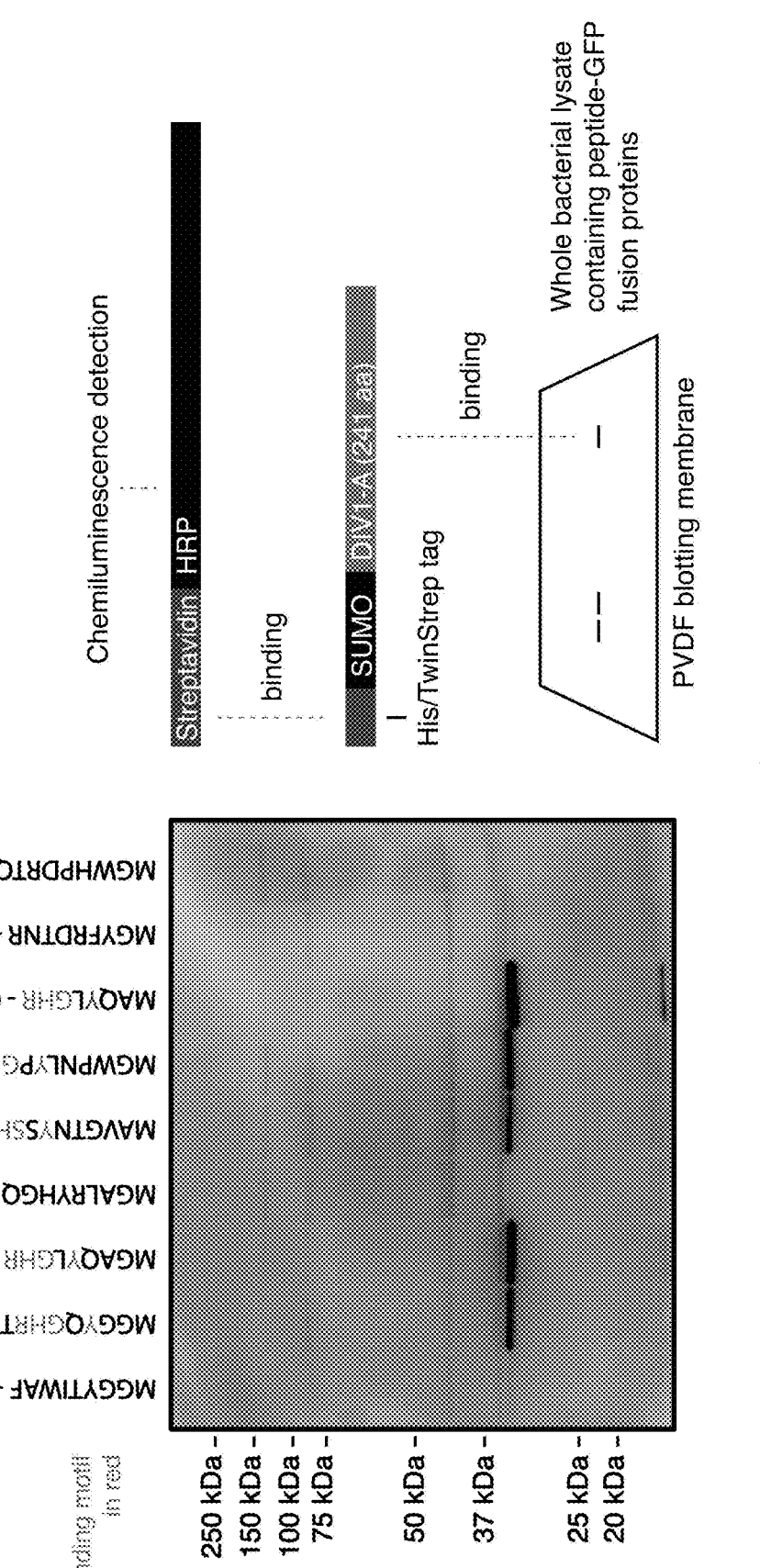

Polynucleotides systems comprising selected hits (FIG. 2) were synthesized on DNA plasmids. On the synthesized DNA plasmids, *E. coli* ribosome binding sites were added in front of every open reading frame to aid expression, equalized orientation of the open reading frames. The plasmids were transformed into *E. coli* strain with ExoX and MutS knocked out. The expression of the systems was induced by chemicals. Paired-end deep sequencing of the potential self-diversification at the natural sites of diversity was performed to detect self-diversification. The test results were shown in FIGS. 4A and 4B.

Among the selected systems, one system showed efficient self-diversification. The diversity was restricted to Adenine (A)-templated positions as predicted by the metagenome sequences. The overall diversification rate at A-templated positions was approximately 1%. Co-diversification rate of the independent positions was approximately 50%. The complexity of this system may be about $1.8 \times 10^{13}$ variants (same range as human antibodies/T-cell receptors). The test results were shown in FIGS. 5A-5D.

The analysis revealed that the system comprises the C-type lectin fold gene and had homology to human FGE enzyme (known to bind and covalently modify specific target peptides).

The system is allowed to diversify itself. Variants with intended function (e.g., binding/enzymatic targeting activity) were pulled out and further validated. The validation may be performed using phage display, a toxin inhibition/survival, bacterial surface display, bacterial-two-hybrid screening, or other means.

The generated diversified molecules may be used as high-complexity barcoding in human cells for connectomics, diversification of non-natural target genes, evolution of e.g. enzymes, antibodies, nanobodies, non-coding RNAs, barcodes, enhancers, and/or promoters.

Example 2

DIV1, a 27.3 kDa protein was identified to be diversified by a DGR in metagenome data from the Crystal Geyser in Utah and found to bind specific linear peptide motifs on a western blot membrane and displayed on M13 phage (FIGS.

6A-6C). DIV1 may be used to replace antibodies in diagnostic, therapeutic, and basic research applications.

Another DGR-diversified protein (DIV18) was also identified and found to bind specific peptide motifs as indicated by phage display data (FIGS. 7A and 7B). This protein is smaller than DIV1 and also may be used for programmable antibody-like peptide binding. Sequences of DIV1 and DIV18 are shown in Table 2.

Example 3

Figures 8A, 8B:
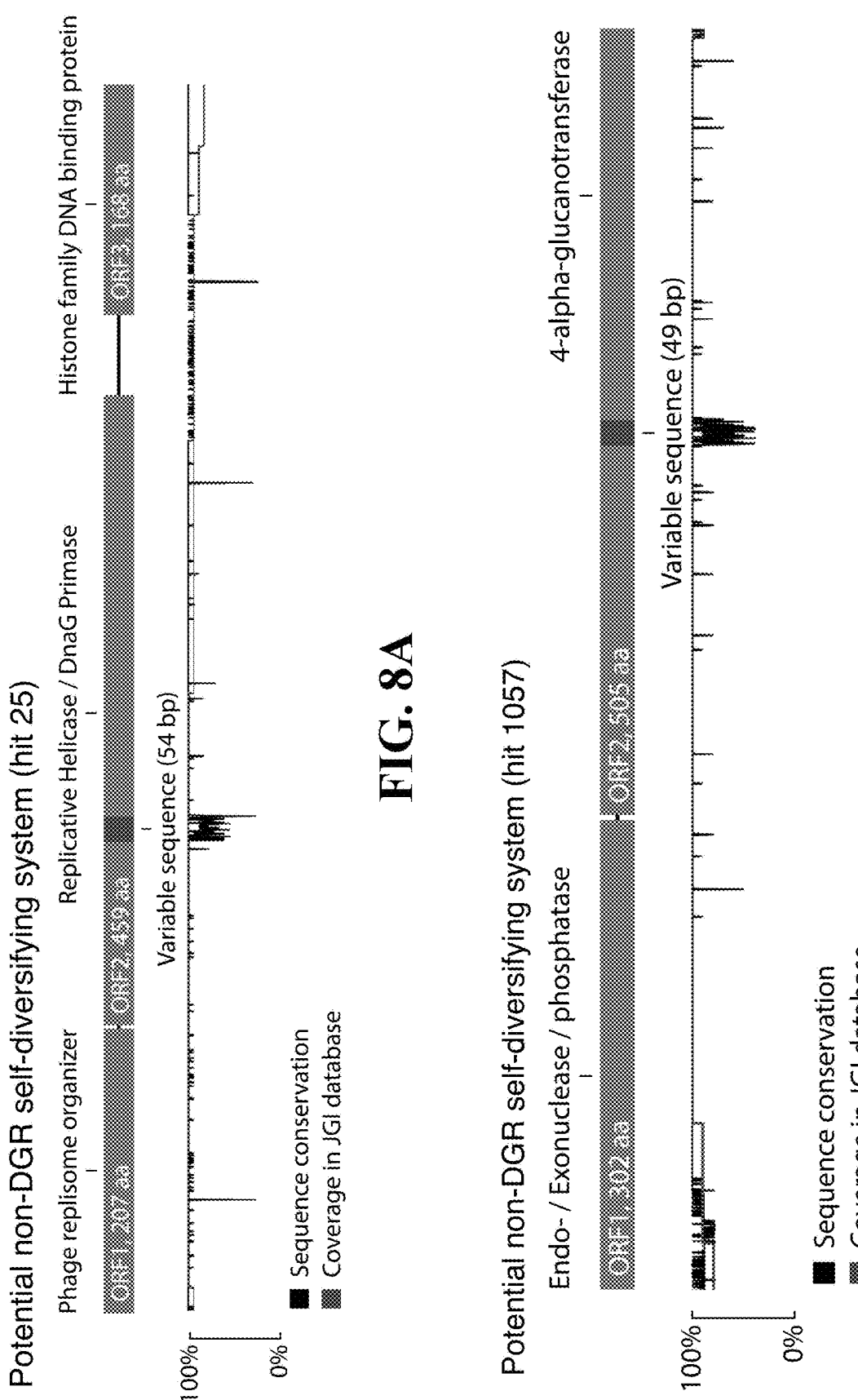
FIGS. 8A and 8B shows two exemplary non-DGR diversifying systems.

Two diversity generating systems (Non-DGR 25 and Non-DGR 1057) that are not diversity generating retroelements were also identified. The two non-DGR systems were found to self-diversify based on JGI metagenome data and contain nucleic-acid interacting proteins (FIGS. 8A and 8B). Sequences of the two systems are shown in Table 1.

Figure 9A:
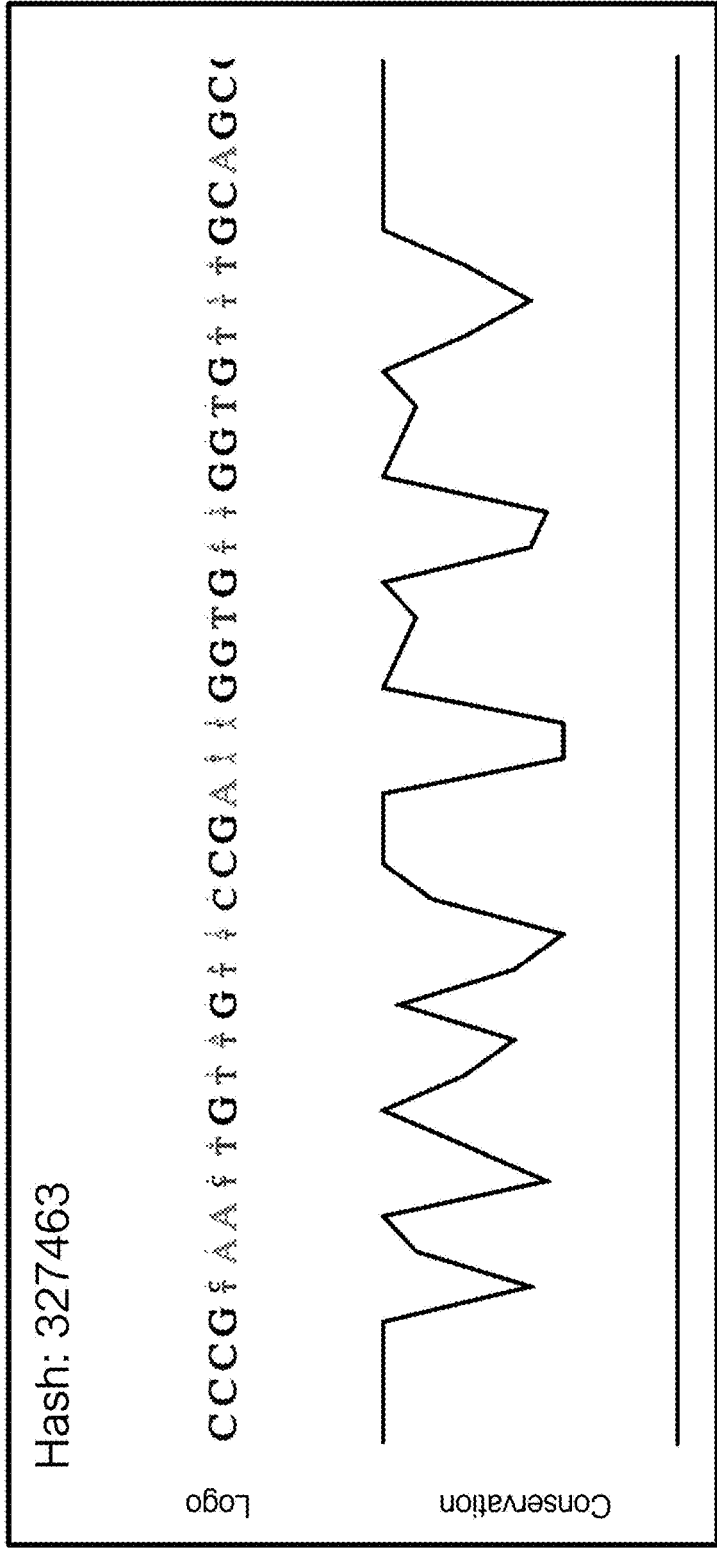
FIG. 9 shows exemplary hit (SEQ ID NOs: 1-3).

An example hit is shown in FIG. 9 (SEQ ID NOs 1-2).

Example 4

Figure 11:
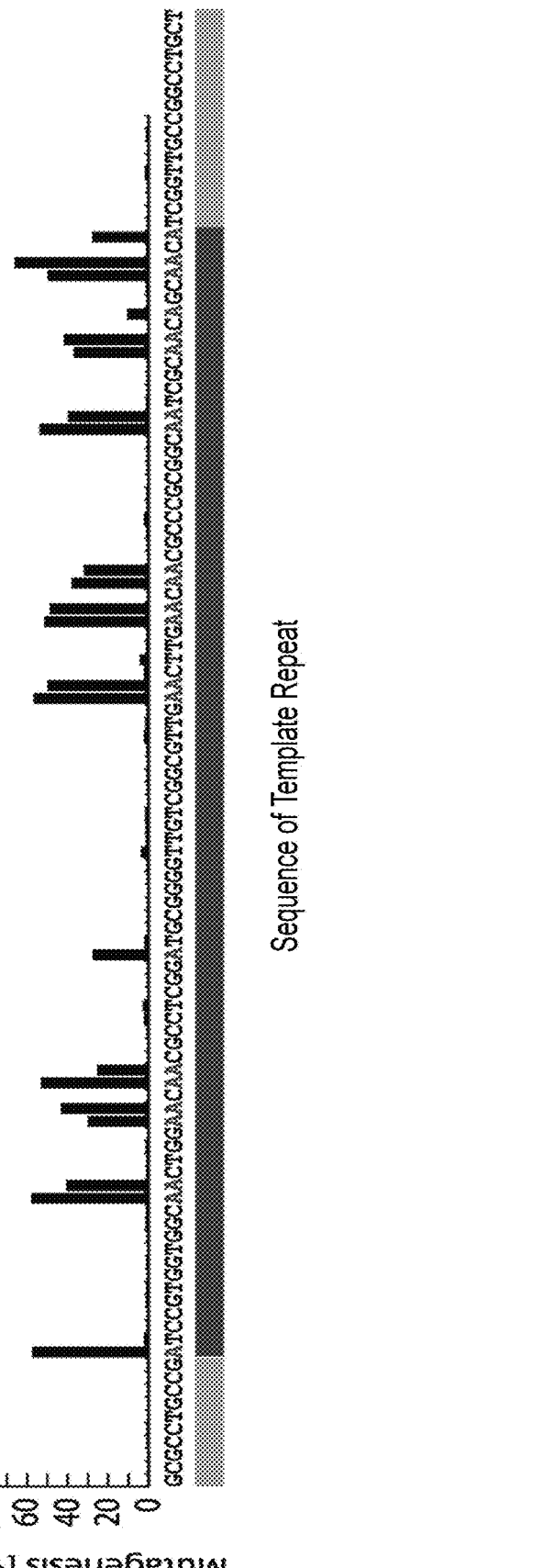
FIG. 11 shows that Hit 214 self-diversified in *E. coli* (SEQ ID NO: 85).

An exemplary self-diversifying system (Hit 214) is shown in FIG. 10. Hit 214 self-diversified in *E. coli* (FIG. 11).

Figure 12:
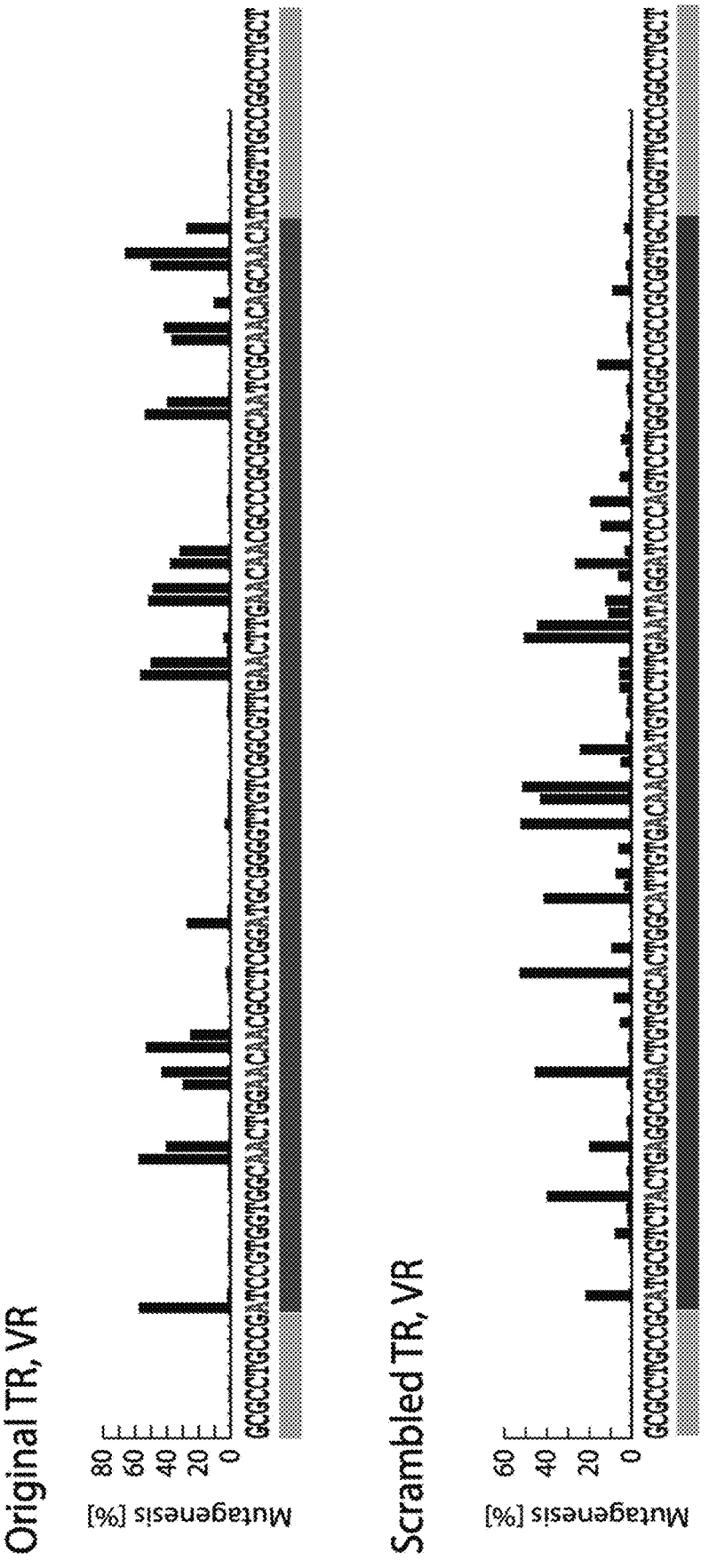
FIG. 12 show that Hit 214 underwent dA-dependent diversification (SEQ ID NOs: 86 and 87).
Figure 13:
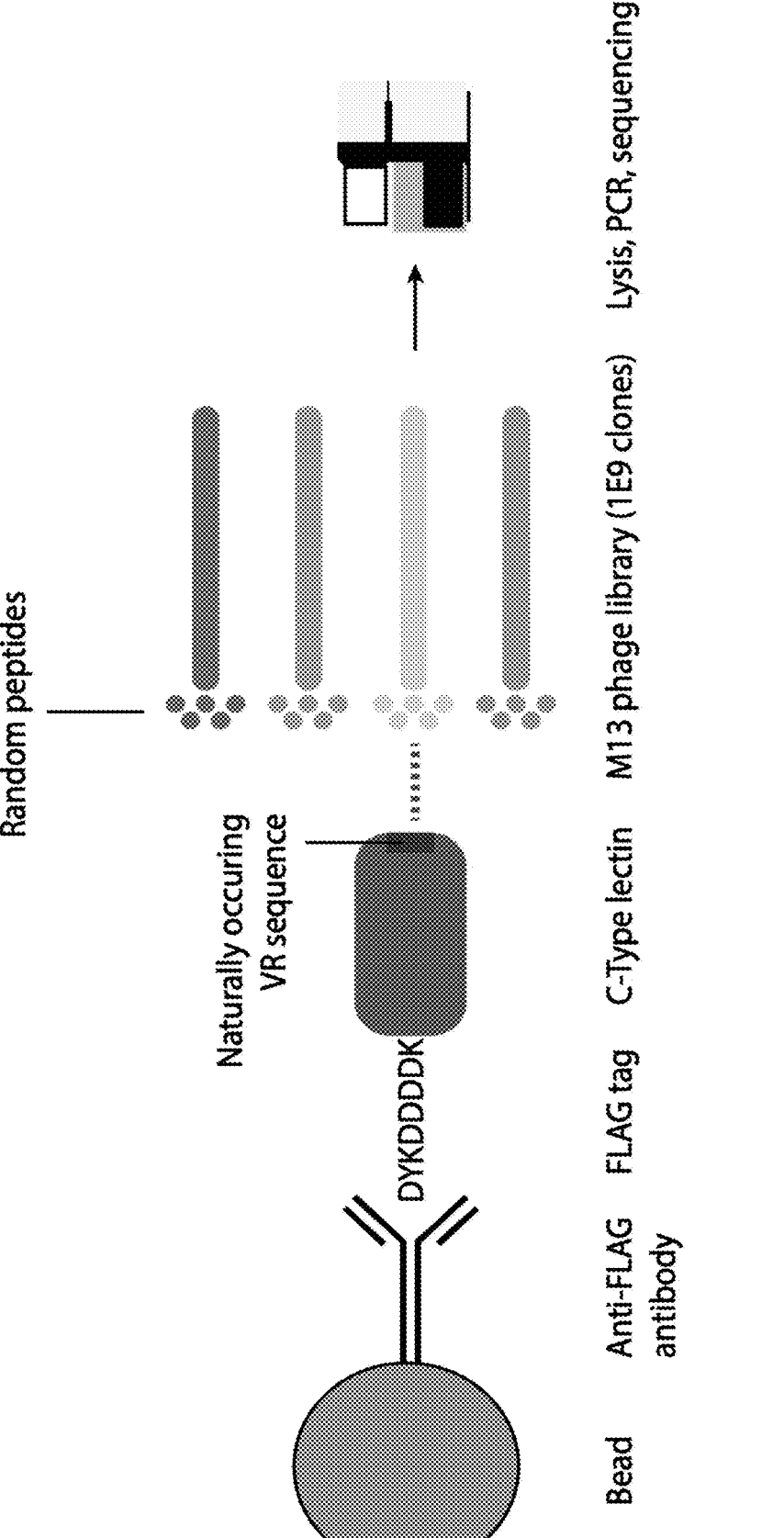
FIG. 13 shows an example 1-step phage display for screening binding molecules derived from diversity generating systems disclosed herein (SEQ ID NO: 88).
Figure 14:
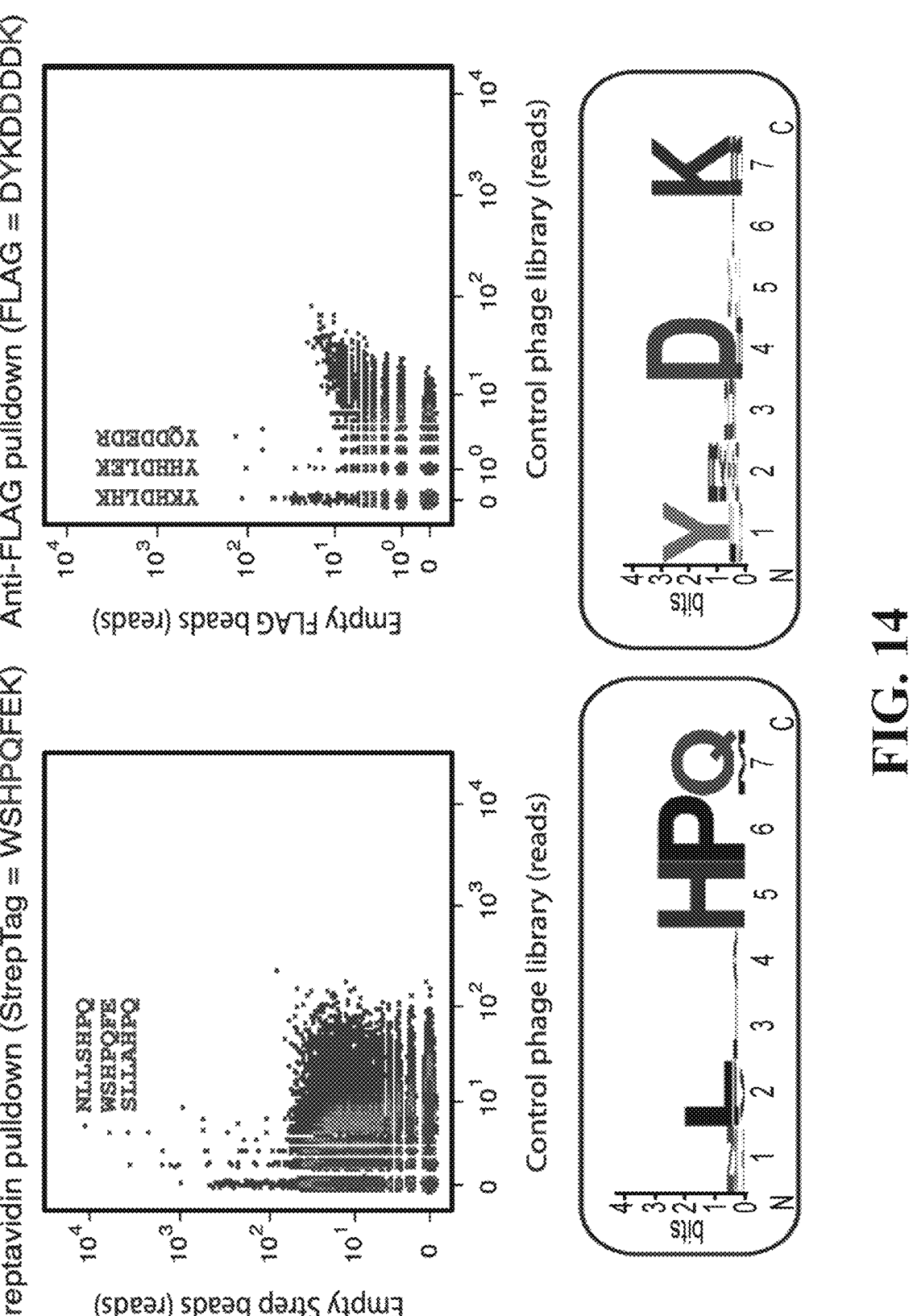
FIG. 14 shows example results of 2 positive controls from a 1-step phage display screen (SEQ ID NOs: 89 and 88) (SEQ ID NOs: 90-95).
Figure 15:
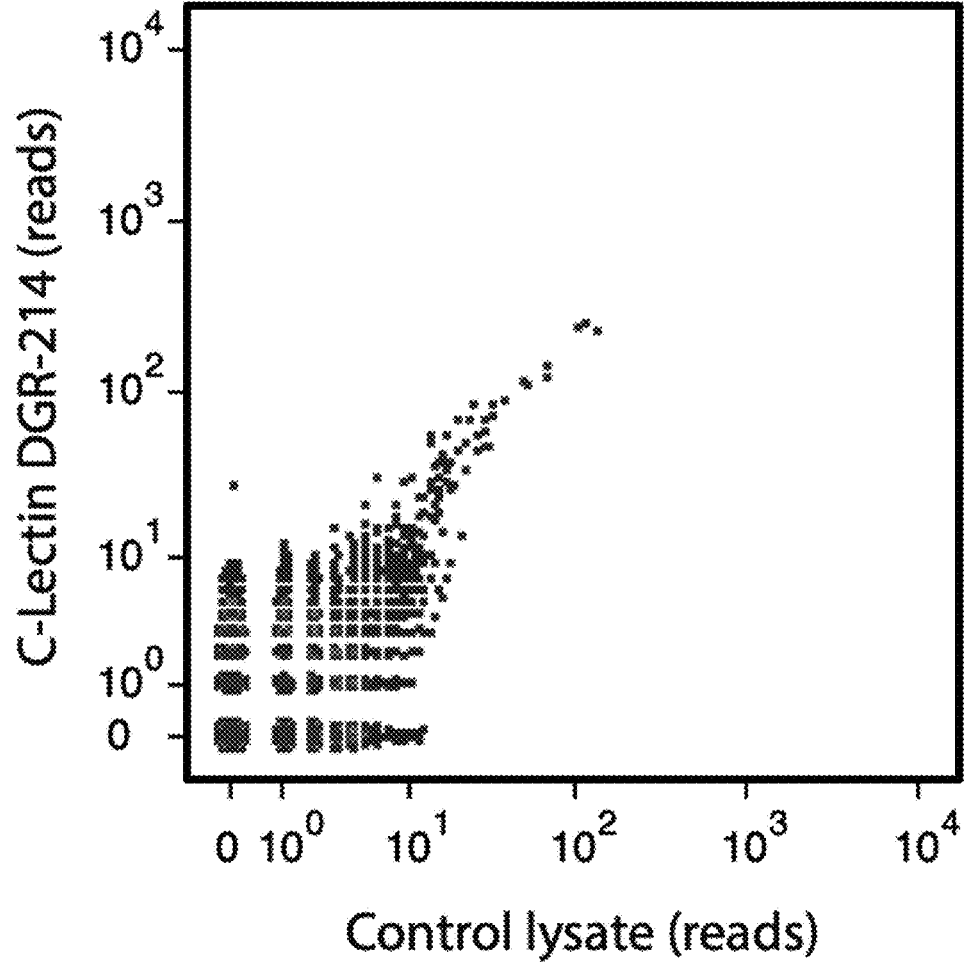
FIG. 15 shows binding assays were performed to identify peptide ligands that bound to Hit 214.

Hit214 underwent dA-dependent diversification, which was reprogrammable (FIG. 12). The diversified protein in Hit 214 is c-type lectin fold. It is homologous to human formylglycin-generating enzyme (FGE). Its variable region overlaps with predicted target-peptide binding site. A 1-step phage display assay was used to determine the binding of a self-diversified protein with a target molecule (FIG. 13). Two positive controls were used in the binding assay (FIG. 14). Binding assays were performed to identify peptide ligands that bound to Hit 214 (FIG. 15).

Hit 214 may be reprogramed (FIG. 16). Two positions in the hairpin loop were found to be important for mutagenic homing (FIG. 16). Hit 214 was reprogramed with three constructs of DIV1 (FIGS. 17A-17E). Fusion construct D self-diversified at A-positions after 24 hours of induction (0.15% homing) (FIGS. 17A-17E).

An exemplary search strategy is shown in FIG. 18.

Figure 19:
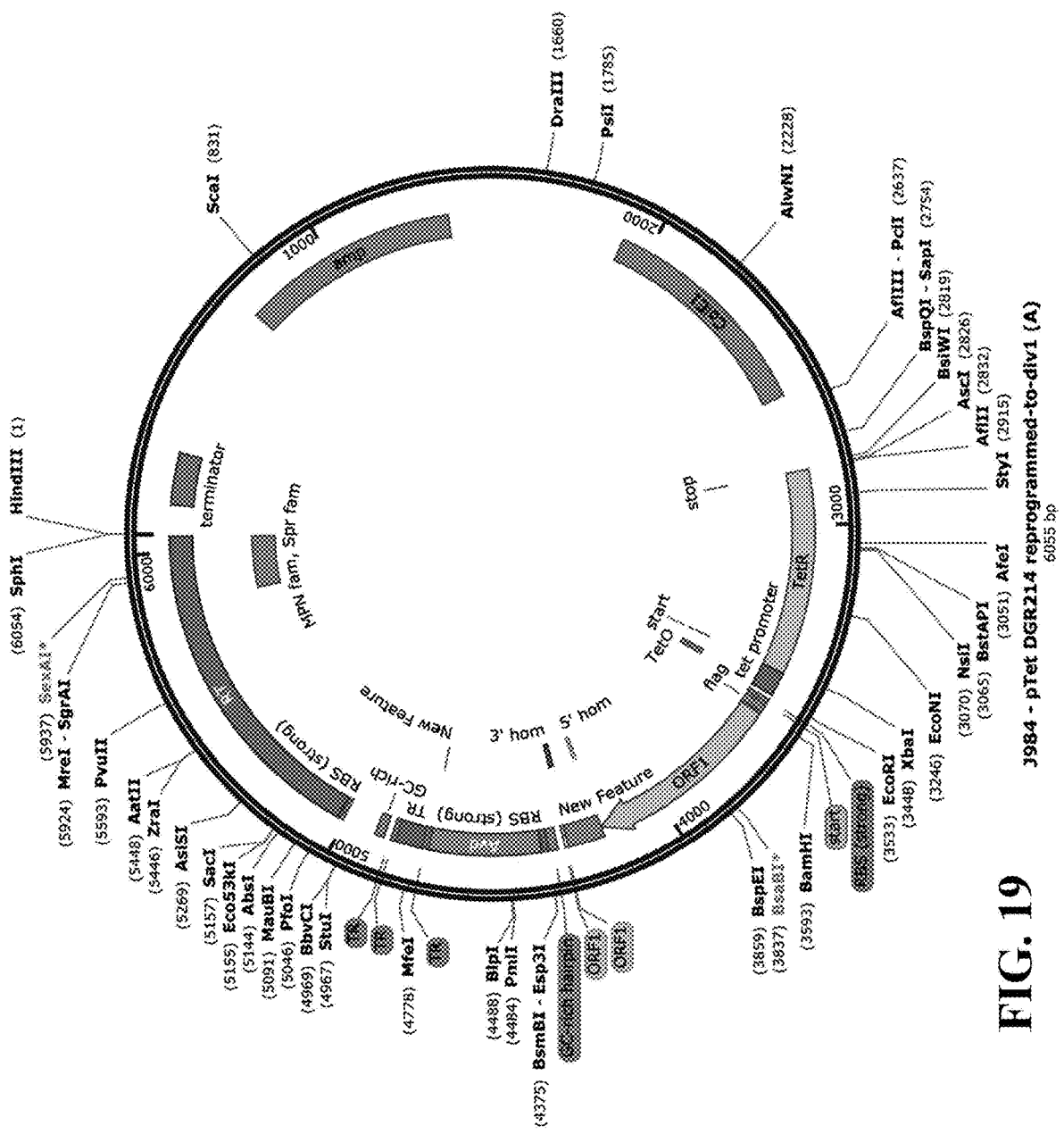
FIGS. 19-22 show maps of the constructs-DIV1 A, DIV1 B, DIV1 D, and DIV1 G.
Figure 20:
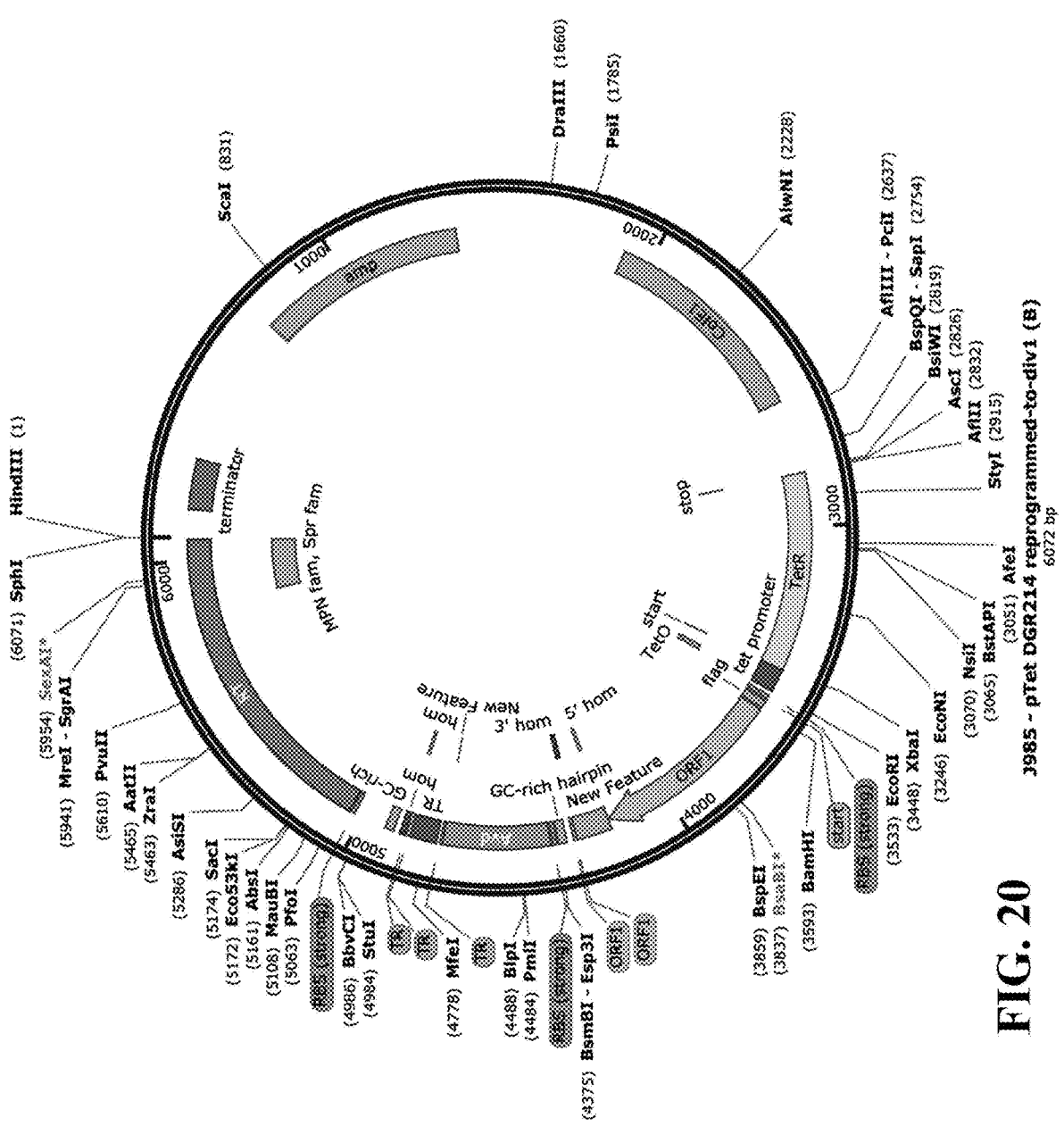
Figure 21:
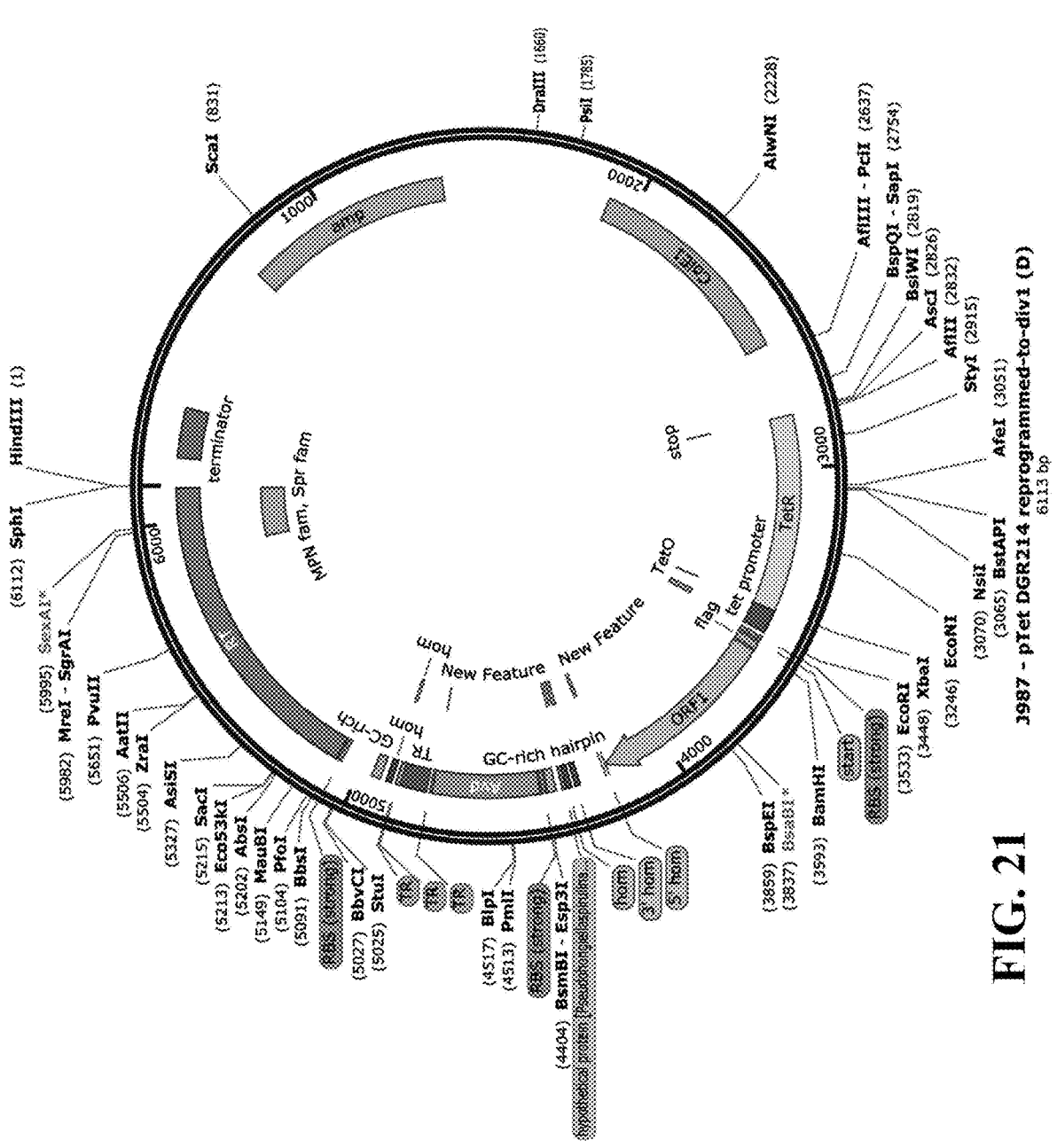
Figure 22:
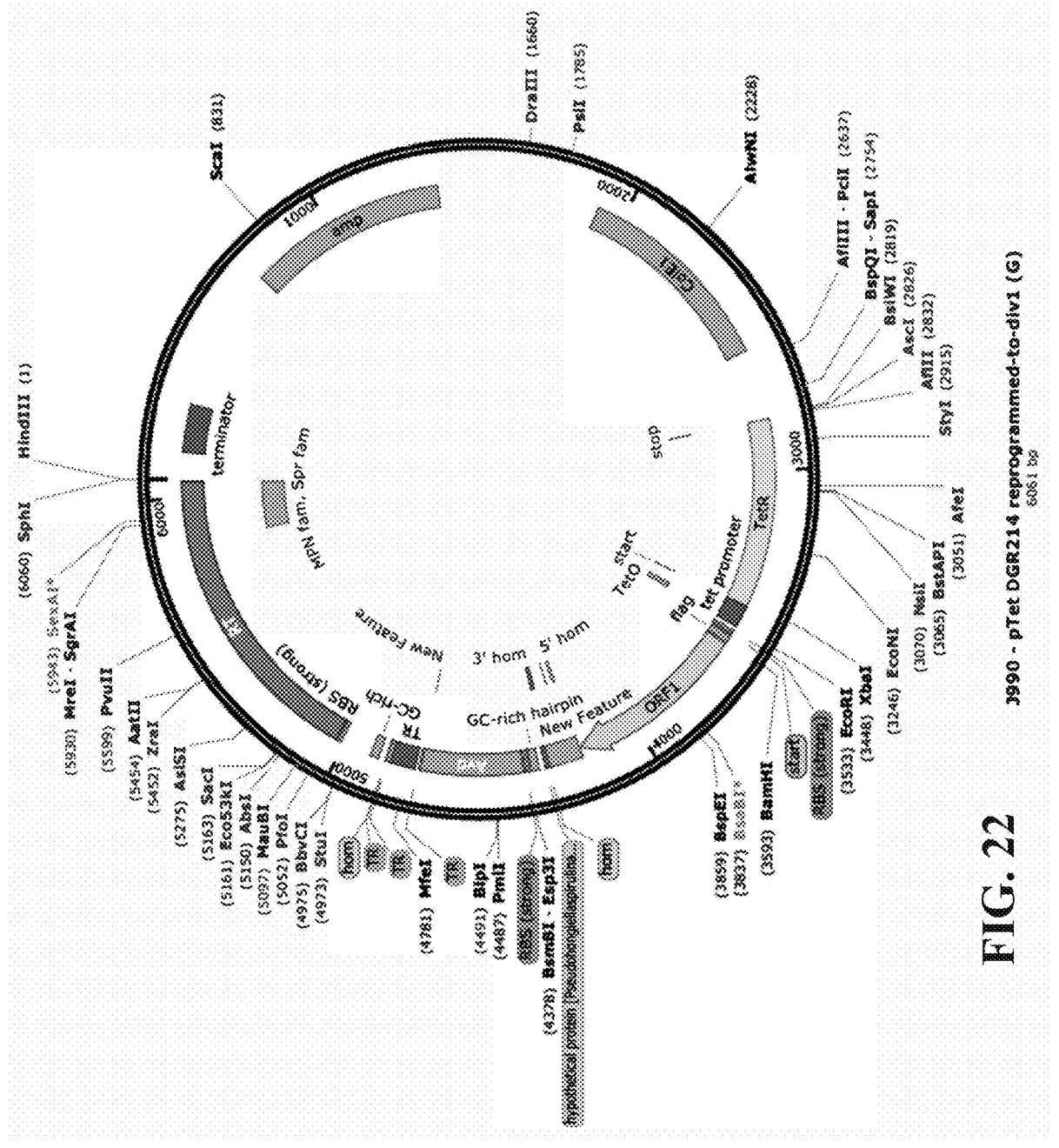

The sequences (on pTet plasmid) of reprogramed Hit 214 with DIV1 constructs A, B, D, and G are shown below. The maps of the constructs are shown in FIG. 19 (DIV1 A), FIG. 20 (DIV1 B), FIG. 21 (DIV1 D), and FIG. 22 (DIV1 G).

TABLE 3

```
7984-pTet DGR214          1 AAGCTTGGCT GTTTTGGCGG ATGAGAGAAG ATTTTCAGCC TGATACAGAT TAAATCAGAA
reprogrammed-to-div1 (A)  61 CGCAGAAGCG GTCTGATAAA ACAGAATTTG CCTGGCGGCA GTAGCGCGGT GGTCCCACCT
(SEQ ID NO: 5)           121 GACCCCATGC CGAACTCAGA AGTGAAACGC CGTAGCGCCG ATGGTAGTGT GGGGTCTCCC
                         181 CATGCGAGAG TAGGGAACTG CCAGGCATCA AATAAAACGA AAGGCTCAGT CGAAAGACTG
                         241 GGCCTTTCGT TTTATCTGTT GTTTGTCGGT GAACGCTCTC CTGAGTAGGA CAAATCCGCC
                         301 GGGAGCGGAT TTGAACGTTG CGAAGCAACG GCCCGGAGGG TGGCGGGCAG GACGCCCGCC
                         361 ATAAACTGCC AGGCATCAAA TTAAGCAGAA GGCCATCCTG ACGGATGGCC TTTTTGCGTT
                         421 TCTACAAACT CTTTTGTTTA TTTTTCTAAA TACATTCAAA TATGTATCCG CTCATGAGAC
                         481 AATAACCCTG ATAAATGCTT CAATAATATT GAAAAAGGAA GAGTATGAGT ATTCAACATT
                         541 TCCGTGTCGC CCTTATTCCC TTTTTTGCGG CATTTTGCCT TCCTGTTTTT GCTCACCCAG
                         601 AAACGCTGGT GAAAGTAAAA GATGCTGAAG ATCAGTTGGG TGCACGAGTG GGTTACATCG
                         661 AACTGGATCT CAACAGCGGT AAGATCCTTG AGAGTTTTCG CCCCGAAGAA CGTTTTCCAA
                         721 TGATGAGCAC TTTTAAAGTT CTGCTATGTG GCGCGGTATT ATCCCGTGTT GACGCCGGGC
                         781 AAGAGCAACT CGGTCGCCGC ATACACTATT CTCAGAATGA CTTGGTTGAG TACTCACCAG
                         841 TCACAGAAAA GCATCTTACG GATGGCATGA CAGTAAGAGA ATTATGCAGT GCTGCCATAA
                         901 CCATGAGTGA TAACACTGCG GCCAACTTAC TTCTGACAAC GATCGGAGGA CCGAAGGAGC
                         961 TAACCGCTTT TTTGCACAAC ATGGGGGATC ATGTAACTCG CCTTGATCGT TGGGAACCGG
                        1021 AGCTGAATGA AGCCATACCA AACGACGAGC GTGACACCAC GATGCCTGCA GCAATGGCAA
                        1081 CAACGTTGCG CAAACTATTA ACTGGCGAAC TACTTACTCT AGCTTCCCGG CAACAATTAA
                        1141 TAGACTGGAT GGAGGCGGAT AAAGTTGCAG GACCACTTCT GCGCTCGGCC CTTCCGGCTG
                        1201 GCTGGTTTAT TGCTGATAAA TCTGGAGCCG GTGAGCGTGG GTCTCGCGGT ATCATTGCAG
                        1261 CACTGGGGCC AGATGGTAAG CCCTCCCGTA TCGTAGTTAT CTACACGACG GGGAGTCAGG
                        1321 CAACTATGGA TGAACGAAAT AGACAGATCG CTGAGATAGG TGCCTCACTG ATTAAGCATT
                        1381 GGTAACTGTC AGACCAAGTT TACTCATATA TACTTTAGAT TGATTTACGC GCCCTGTAGC
                        1441 GGCGCATTAA GCGCGGCGGG TGTGGTGGTT ACGCGCAGCG TGACCGCTAC ACTTGCCAGC
                        1501 GCCCTAGCGC CCGCTCCTTT CGCTTTCTTC CCTTCCTTTC TCGCCACGTT CGCCGGCTTT
                        1561 CCCCGTCAAG CTCTAAATCG GGGGCTCCCT TTAGGGTTCC GATTTAGTGC TTTACGGCAC
                        1621 CTCGACCCCA AAAAACTTGA TTTGGGTGAT GGTTCACGTA GTGGGCCATC GCCCTGATAG
                        1681 ACGGTTTTTC GCCCTTTGAC GTTGGAGTCC ACGTTCTTTA ATAGTGGACT CTTGTTCCAA
                        1741 ACTTGAACAA CACTCAACCC TATCTCGGGC TATTCTTTTG ATTTATAAGG GATTTTGCCG
                        1801 ATTTCGGCCT ATTGGTTAAA AAATGAGCTG ATTTAACAAA AATTTAACGC GAATTTTAAC
                        1861 AAAATATTAA CGTTTACAAT TTAAAAGGAT CTAGGTGAAG ATCCTTTTTG ATAATCTCAT
                        1921 GACCAAAATC CCTTAACGTG AGTTTTCGTT CCACTGAGCG TCAGACCCCG TAGAAAAGAT
                        1981 CAAAGGATCT TCTTGAGATC CTTTTTTTCT GCGCGTAATC TGCTGCTTGC AAACAAAAAA
                        2041 ACCACCGCTA CCAGCGGTGG TTTGTTTGCC GGATCAAGAG CTACCAACTC TTTTTCCGAA
                        2101 GGTAACTGGC TTCAGCAGAG CGCAGATACC AAATACTGTC CTTCTAGTGT AGCCGTAGTT
                        2161 AGGCCACCAC TTCAAGAACT CTGTAGCACC GCCTACATAC CTCGCTCTGC TAATCCTGTT
                        2221 ACCAGTGGCT GCTGCCAGTG GCGATAAGTC GTGTCTTACC GGGTTGGACT CAAGACGATA
                        2281 GTTACCGGAT AAGGCGCAGC GGTCGGGCTG AACGGGGGGT TCGTGCACAC AGCCCAGCTT
                        2341 GGAGCGAACG ACCTACACCG AACTGAGATA CCTACAGCGT GAGCTATGAG AAAGCGCCAC
                        2401 GCTTCCCGAA GGGAGAAAGG CGGACAGGTA TCCGGTAAGC GGCAGGGTCG GAACAGGAGA
                        2461 GCGCACGAGG GAGCTTCCAG GGGGAAACGC CTGGTATCTT TATAGTCCTG TCGGGTTTCG
                        2521 CCACCTCTGA CTTGAGCGTC GATTTTTGTG ATGCTCGTCA GGGGGGCGGA GCCTATGGAA
                        2581 AAACGCCAGC AACGCGGCCT TTTTACGGTT CCTGGCCTTT TGCTGGCCTT TTGCTCACAT
                        2641 GTTCTTTCCT GCGTTATCCC CTGATTCTGT GGATAACCGT ATTACCGCCT TTGAGTGAGC
                        2701 TGATACCGCT CGCCGCAGCC GAACGACCGA GCGCAGCGAG TCAGTGAGCG AGGAAGCGGA
                        2761 AGAGCGCCTG ATGCGGTATT TTCTCCTTAC GCATCTGTGC GGTATTTCAC ACCGCATACG
                        2821 TACGGGCGCG CCTTAAGACC CACTTTCACA TTTAAGTTGT TTTTCTAATC CGCATATGAT
                        2881 CAATTCAAGG CCGAATAAGA AGGCTGGCTC TGCACCTTGG TGATCAAATA ATTCGATAGC
                        2941 TTGTCGTAAT AATGGCGGCA TACTATCAGT AGTAGGTGTT TCCCTTTCTT CTTTAGCGAC
                        3001 TTGATGCTCT TGATCTTCCA ATACGCAACC TAAAGTAAAA TGCCCCACAG CGCTGAGTGC
```

TABLE 3-continued

```
3061 ATATAATGCA TTCTCTAGTG AAAAACCTTG TTGGCATAAA AAGGCTAATT GATTTTCGAG
3121 AGTTTCATAC TGTTTTTCTG TAGGCCGTGT ACCTAAATGT ACTTTTGCTC CATCGCGATG
3181 ACTTAGTAAA GCACATCTAA AACTTTTAGC GTTATTACGT AAAAAATCTT GCCAGCTTTC
3241 CCCTTCTAAA GGGCAAAAGT GAGTATGGTG CCTATCTAAC ATCTCAATGG CTAAGGCGTC
3301 GAGCAAAGCC CGCTTATTTT TTACATGCCA ATACAATGTA GGCTGCTCTA CACCTAGCTT
3361 CTGGGCGAGT TTACGGGTTG TTAAACCTTC GATTCCGACC TCATTAAGCA GCTCTAATGC
3421 GCTGTTAATC ACTTTACTTT TATCTAATCT AGACATCATT AATTCCTAAT TTTTGTTGAC
3481 ACTCTATCGT TGATAGAGTT ATTTTACCAC TCCCTATCAG TGATAGAGAA AAGAATTCAA
3541 AAGATCTAAA GAGGAGAAAG GATCTATGGA CTACAAAGAC GATGACGACA AGggatccAT
3601 GAAGAAACAG AGCAATCAGA CCGTTCGTAT GGCAACACCG GGTCAGATTA AAGATGTTAT
3661 TAGCGCAGTT GTTGAAAGCA TTCCGGTGAA TAATCTGACA TATGAAATGG CCCAGTATTT
3721 CATCGGTCGT AAAAAATGGC TGGGCACCGA AATGAAAAAA ATCTTTAGCG TGGATAACAG
3781 CCATGCAGAT CTGATTGCAG ATTGGCAGGC ATTTTATTGT GGTCTGGGTA TTGATTGCGA
3841 TCTGAGCGGT GTTATTATTC CGGATGATCC TGGTGGTTTT GGTCGTGTGA TTATTATGGC
3901 ACAGGGTATT ACACCGCAGA GCGGTTATGA TCTGTGTGCA AAATTCTTTC CGTGCTGGAA
3961 ATATACCGAT AAAAACCTGG ATGAAGTTGT GGTTAGCGAA CGTACCGCAA AAGATGTTTA
4021 TGCAATTCGT GTTCGTGATC GTGTTGAAGC AGATGAAGAA CTGCGTAATC GTAGCTATAA
4081 TGATCTGAAA CGTCAGGGCA TTATTGGCAT TACCCTGGAA GAACGTGAAA TCTTTGAACT
4141 GAAATTTTTC AAAGAAACCG CAGGCAAACA CCTGGATATC AAAAATTGGA CCTTTTGTCT
4201 GGGTTCGTGC TATGACGGCG GCAATGTGCC GAGCGCCTCG TGGCGCAGCG GCGAGTTCGA
4261 GGTCGACTGG TGCAATCCCG GCGATGTCTT CGACGATCTG TGTTCCCGTC AGGCAGTTAG
4321 CTAATGCCTG TTCATCTGTG TTCTGCGGCC CTGCGCGATA GCGCGGGCCG TCTCTAAAAG
4381 AGGAGAAAGG ATCTATGCAA CAGCTTCAAG TCGCGCAGCG GGTCGAGGCG ATGATCGAGT
4441 ATGGCTATAT AGCTGTACGG CATTTCCCGA AATCGGAGCG TCACGTGCTC AGCGCCGAGC
4501 TGCGCGGCTC TATGTGGCGG CTGCTGCGGC TCGTGATCGT CTGCGGCAAG CGGTATCACA
4561 AAAAGACGAC ACTCGCAGAG CTGGATACCG AACTGGAGCT GCTGCGCCGC GAAGTGCGGC
4621 TCGCAAAAGA CCTGAAGTTC CTGCCGTTCC GACAATACGA AATCTGGTCG CGTCATCTCG
4681 ACGAGATCGG TCGCATGATC GGCGGCTGGA TTAAACACGC AAAACAGGGT TAAGCGCATT
4741 TGGGTTCGTG CTATGACGAC GGCAATGTGC CGAACGCCAA TTGGAACAGC GGCAAGTTCA
4801 AGGTCAACTG GTACAATCCC gACAATGTCA ACGACAATCT GTGTTCCCGT CAGCTTGAAG
4861 ATCGTCAGAA ACAGCGCGGT CACGGTGGCG CTGTCAGCAC GACATCAAAA GGGCGCTTGA
4921 TCCTCGGCCC ATGCCGAAAC ATTAACAGGC ATCGATCGTG TAGTAGGCCT CAGCCGAGGC
4981 TCGATCGTCG CCGCTTTGGC TCGATAAAGA GGAGAAAGGA TCTATGAAGA CATACAACAA
5041 CCTGTTCCCG GAGATATACA GCTTCGACAA CCTGCATGAC GCCTACGTCC GCGCGCGCCG
5101 CGGCAAACGC CACCAGGCCG ACGTGCTGCG CTTCGAGCAA AACCTCGAGG GCGAGCTCAT
5161 ACAACTACAG AACGAACTGA TCTGGCGCGA GTACGAAACT GGCCCGTATC GGCGTTTCCA
5221 TGTGCACGAG CCGAAAAAGC GTTTGGTCGC CGCGCTGCCC TTTCGCGATC GCGTCGTACA
5281 GCACAGCCTA ATCGCCGCGA TCGAGCCCAT TTGGGAGTCG CGATTCATCG ATCAGAGCTA
5341 CGCCTGCCGT CCCGGCCGGG GCGTGCACCG CGGTGCAGAC AAAGCCCAAC AATGGCTGCG
5401 CGAGGTGCGG GCCACACACG GCCGCGTCTA CGCGCTCAAG GCCGACGTCG CAGGTTATTT
5461 CGCATCGATC GATCACGACG TTCTGCGCAC GCAGCTAGAA CGCCGAATCG CTTGCCGTCC
5521 AACGCTATAC CTGCTGCTCG GCATCATCGA AACCTGGCAT CCCGGCCTTC CCATCGGCAA
5581 CCTCACGTCG CAGCTGTGCG CCAATATCTA TTTGCACGAT TTCGACGTAT TCGCAAAACA
5641 GCACGTCGGC GCACGCCGCT ATATGAGGTA TATGGATGAC TGGCTCATCG TCGACCACGA
5701 CAAAGCGCGC CTGCACGCAC AGCGCCGCGT GCTCGAGGAC TGGCTGCACG ACAATCTGCG
5761 CCTGCAGCTC AATAACAAGA CCCAGATATT TCCCGTCAGC CCACGCCACG GCCGCGGACT
5821 CGACTTCCTC GGATATCGAA TATGCCCCAC ACATCGAAAG ATTCGCAAAA ACAGCGTCAA
5881 ACGgATGCAG AAAAAACTAC GTGCGCTCGA ACGCCGCTAC GCCGCCGGCG ATATCGACCT
5941 GGTCGACATC GAGCCCGTGA TCCAGAGCTG GGTCGCCCAC GCCTCCCACG CCAGCAGCTA
6001 TCAGATCCGC CGCGCGGTGC TGGAGCGCGC GGTTTTCAAA CGCCAATAAG CATGC
```

J985-pTet DGR214
reprogrammed-to-div1 (B)
(SEQ ID NO: 6)

```
   1 AAGCTTGGCT GTTTTGGCGG ATGAGAGAAG ATTTTCAGCC TGATACAGAT TAAATCAGAA
  61 CGCAGAAGCG GTCTGATAAA ACAGAATTTG CCTGGCGGCA GTAGCGCGGT GGTCCCACCT
 121 GACCCCATGC CGAACTCAGA AGTGAAACGC CGTAGCGCCG ATGGTAGTGC GGGGTCTCCC
 181 CATGCGAGAG TAGGGAACTG CCAGGCATCA AATAAAACGA AAGGCTCAGT CGAAAGACTG
 241 GGCCTTTCGT TTTATCTGTT GTTTGTCGGT GAACGCTCTC CTGAGTAGGA CAAATCCGCC
 301 GGGAGCGGAT TTGAACGTTG CGAAGCAACG GCCCGGAGGG TGGCGGGCAG GACGCCCGCC
 361 ATAAACTGCC AGGCATCAAA TTAAGCAGAA GGCCATCCTG ACGGATGGCC TTTTTGCGTT
 421 TCTACAAACT CTTTTGTTTA TTTTTCTAAA TACATTCAAA TATGTATCCG CTCATGAGAC
 481 AATAACCCTG ATAAATGCTT CAATAATATT GAAAAAGGAA GAGTATGAGT ATTCAACATT
 541 TCCGTGTCGC CCTTATTCCC TTTTTTGCGG CATTTTGCCT TCCTGTTTTT GCTCACCCAG
 601 AAACGCTGGT GAAAGTAAAA GATGCTGAAG ATCAGTTGGG TGCACGAGTG GGTTACATCG
 661 AACTGGATCT CAACAGCGGT AAGATCCTTG AGAGTTTTCG CCCCGAAGAA CGTTTTCCAA
 721 TGATGAGCAC TTTTAAAGTT CTGCTATGTG GCGCGGTATT ATCCCGTGTT GACGCCGGGC
 781 AAGAGCAACT CGGTCGCCGC ATACACTATT CTCAGAATGA CTTGGTTGAG TACTCACCAG
 841 TCACAGAAAA GCATCTTACG GATGGCATGA CAGTAAGAGA ATTATGCAGT GCTGCCATAA
 901 CCATGAGTGA TAACACTGCG GCCAACTTAC TTCTGACAAC GATCGGAGGA CCGAAGGAGC
 961 TAACCGCTTT TTTGCACAAC ATGGGGGATC ATGTAACTCG CCTTGATCGT TGGGAACCGG
1021 AGCTGAATGA AGCCATACCA AACGACGAGC GTGACACCAC GATGCCTGCA GCAATGGCAA
1081 CAACGTTGCG CAAACTATTA ACTGGCGAAC TACTTACTCT AGCTTCCCGG CAACAATTAA
1141 TAGACTGGAT GGAGGCGGAT AAAGTTGCAG GACCACTTCT GCGCTCGGCC CTTCCGGCTG
1201 GCTGGTTTAT TGCTGATAAA TCTGGAGCCG GTGAGCGTGG GTCTCGCGGT ATCATTGCAG
1261 CACTGGGGCC AGATGGTAAG CCCTCCCGTA TCGTAGTTAT CTACACGACG GGGAGTCAGG
1321 CAACTATGGA TGAACGAAAT AGACAGATCG CTGAGATAGG TGCCTCACTG ATTAAGCATT
1381 GGTAACTGTC AGACCAAGTT TACTCATATA TACTTTAGAT TGATTTACGC GCCCTGTAGC
1441 GGCGCATTAA GCGCGGCGGG TGTGGTGGTT ACGCGCAGCG TGACCGCTAC ACTTGCCAGC
1501 GCCCTAGCGC CCGCTCCTTT CGCTTTCTTC CCTTCCTTTC TCGCCACGTT CGCCGGCTTT
1561 CCCCGTCAAG CTCTAAATCG GGGGCTCCCT TTAGGGTTCC GATTTAGTGC TTTACGGCAC
1621 CTCGACCCCA AAAAACTTGA TTTGGGTGAT GGTTCACGTA GTGGGCCATC GCCCTGATAG
1681 ACGGTTTTTC GCCCTTTGAC GTTGGAGTCC ACGTTCTTTA ATAGTGGACT CTTGTTCCAA
```

TABLE 3-continued

```
1741 ACTTGAACAA CACTCAACCC TATCTCGGGC TATTCTTTTG ATTTATAAGG GATTTTGCCG
1801 ATTTCGGCCT ATTGGTTAAA AAATGAGCTG ATTTAACAAA AATTTAACGC GAATTTTAAC
1861 AAAATATTAA CGTTTACAAT TTAAAAGGAT CTAGGTGAAG ATCCTTTTTG ATAATCTCAT
1921 GACCAAAATC CCTTAACGTG AGTTTTCGTT CCACTGAGCG TCAGACCCCG TAGAAAAGAT
1981 CAAAGGATCT TCTTGAGATC CTTTTTTTCT GCGCGTAATC TGCTGCTTGC AAACAAAAAA
2041 ACCACCGCTA CCAGCGGTGG TTTGTTTGCC GGATCAAGAG CTACCAACTC TTTTTCCGAA
2101 GGTAACTGGC TTCAGCAGAG CGCAGATACC AAATACTGTC CTTCTAGTGT AGCCGTAGTT
2161 AGGCCACCAC TTCAAGAACT CTGTAGCACC GCCTACATAC CTCGCTCTGC TAATCCTGTT
2221 ACCAGTGGCT GCTGCCAGTG GCGATAAGTC GTGTCTTACC GGGTTGGACT CAAGACGATA
2281 GTTACCGGAT AAGGCGCAGC GGTCGGGCTG AACGGGGGGT TCGTGCACAC AGCCCAGCTT
2341 GGAGCGAACG ACCTACACCG AACTGAGATA CCTACAGCGT GAGCTATGAG AAAGCGCCAC
2401 GCTTCCCGAA GGGAGAAAGG CGGACAGGTA TCCGGTAAGC GGCAGGGTCG GAACAGGAGA
2461 GCGCACGAGG GAGCTTCCAG GGGGAAACGC CTGGTATCTT TATAGTCCTG TCGGGTTTCG
2521 CCACCTCTGA CTTGAGCGTC GATTTTTGTG ATGCTCGTCA GGGGGGCGGA GCCTATGGAA
2581 AAACGCCAGC AACGCGGCCT TTTTACGGTT CCTGGCCTTT TGCTGGCCTT TTGCTCACAT
2641 GTTCTTTCCT GCGTTATCCC CTGATTCTGT GGATAACCGT ATTACCGCCT TTGAGTGAGC
2701 TGATACCGCT CGCCGCAGCC GAACGACCGA GCGCAGCGAG TCAGTGAGCG AGGAAGCGGA
2761 AGAGCGCCTG ATGCGGTATT TTCTCCTTAC GCATCTGTGC GGTATTTCAC ACCGCATACG
2821 TACGGGCGCG CCTTAAGACC CACTTTCACA TTTAAGTTGT TTTTCTAATC CGCATATGAT
2881 CAATTCAAGG CCGAATAAGA AGGCTGGCTC TGCACCTTGG TGATCAAATA ATTCGATAGC
2941 TTGTCGTAAT AATGGCGGCA TACTATCAGT AGTAGGTGTT TCCCTTTCTT CTTTAGCGAC
3001 TTGATGCTCT TGATCTTCCA ATACGCAACC TAAAGTAAAA TGCCCCACAG CGCTGAGTGC
3061 ATATAATGCA TTCTCTAGTG AAAAACCTTG TTGGCATAAA AAGGCTAATT GATTTTCGAG
3121 AGTTTCATAC TGTTTTTCTG TAGGCCGTGT ACCTAAATGT ACTTTTGCTC CATCGCGATG
3181 ACTTAGTAAA GCACATCTAA AACTTTTAGC GTTATTACGT AAAAAATCTT GCCAGCTTTC
3241 CCCTTCTAAA GGGCAAAAGT GAGTATGGTG CCTATCTAAC ATCTCAATGG CTAAGGCGTC
3301 GAGCAAAGCC CGCTTATTTT TTACATGCCA ATACAATGTA GGCTGCTCTA CACCTAGCTT
3361 CTGGGCGAGT TTACGGGTTG TTAAACCTTC GATTCCGACC TCATTAAGCA GCTCTAATGC
3421 GCTGTTAATC ACTTTACTTT TATCTAATCT AGACATCATT AATTCCTAAT TTTTGTTGAC
3481 ACTCTATCGT TGATAGAGTT ATTTTACCAC TCCCTATCAG TGATAGAGAA AAGAATTCAA
3541 AAGATCTAAA GAGGAGAAAG GATCTATGGA CTACAAAGAC GATGACGACA AGggatccAT
3601 GAAGAAACAG AGCAATCAGA CCGTTCGTAT GGCAACACCG GGTCAGATTA AGATGTTAT
3661 TAGCGCAGTT GTTGAAAGCA TTCCGGTGAA TAATCTGACA TATGAAATGG CCCAGTATTT
3721 CATCGGTCGT AAAAAATGGC TGGGCACCGA AATGAAAAAA ATCTTTAGCG TGGATAACAG
3781 CCATGCAGAT CTGATTGCAG ATTGGCAGGC ATTTTATTGT GGTCTGGGTA TTGATTGCGA
3841 TCTGAGCGGT GTTATTATTC CGGATGATCC TGGTGGTTTT GGTCGTGTGA TTATTATGGC
3901 ACAGGGTATT ACACCGCAGA GCGGTTATGA TCTGTGTGCA AAATTCTTTC CGTGCTGGAA
3961 ATATACCGAT AAAAACCTGG ATGAAGTTGT GGTTAGCGAA CGTACCGCAA AAGATGTTTA
4021 TGCAATTCGT GTTCGTGATC GTGTTGAAGC AGATGAAGAA CTGCGTAATC GTAGCTATAA
4081 TGATCTGAAA CGTCAGGGCA TTATTGGCAT TACCCTGGAA GAACGTGAAA TCTTTGAACT
4141 GAAATTTTTC AAAGAAACCG CAGGCAAACA CCTGGATATC AAAAATTGGA CCTTTTGTCT
4201 GGGTTCGTGC TATGACGGCG GCAATGTGCC GAGCGCCTCG TGGCGCAGCG GCGAGTTCGA
4261 GGTCGACTGG TGCAATCCCG GCGATGTCTT CGACGATCTG TGTTCCCGTC AGGCAGTTAG
4321 CTAATGCCTG TTCATCTGTG TTCTGCGGCC CTGCGCGATA GCGCGGGCCG TCTCTAAAAG
4381 AGGAGAAAGG ATCTATGCAA CAGCTTCAAG TCGCGCAGCG GGTCGAGGCG ATGATCGAGT
4441 ATGGCTATAT AGCTGTACGG CATTTCCCGA AATCGGAGCG TCACGTGCTC AGCGCCGAGC
4501 TGCGCGGCTC TATGTGGCGG CTGCTGCGGC TCGTGATCGT CTGCGGCAAG CGGTATCACA
4561 AAAAGACGAC ACTCGCAGAG CTGGATACCG AACTGGAGCT GCTGCGCCGC GAAGTGCGGC
4621 TCGCAAAAGA CCTGAAGTTC CTGCCGTTCC GACAATACGA AATCTGGTCG CGTCATCTCG
4681 ACGAGATCGG TCGCATGATC GGCGGCTGGA TTAAACACGA AAAACAGGGT TAAGCGCATT
4741 TGGGTTCGTG CTATGACGAC GGCAATGTGC CGAACGCCAA TTGGAACAGC GGCAAGTTCA
4801 AGGTCAACTG GTACAATCCC gACAATGTCA ACGACAATCT GTGTTCCCGT CAGTCGGTTG
4861 CCGGCCTGCT CTTGAAGATC GTCAGAAACA GCGCGGTCAC GGTGGCGCTG TCAGCACGAC
4921 ATCAAAAGGG CGCTTGATCC TCGGCCCATG CCGAAACATT AACAGGCATC GATCGTGTAG
4981 TAGGCCTCAG CCGAGGCTCG ATCGTCGCCG CTTTGGCTCG ATAAAGAGGA GAAAGGATCT
5041 ATGAAGACAT ACAACAACCT GTTCCCGGAG ATATACAGCT TCGACAACCT GCATGACGCC
5101 TACGTCCGCG CGCGCCGCGG CAAACGCCAC CAGGCCGACG TGCTGCGCTT CGAGCAAAAC
5161 CTCGAGGGCG AGCTCATACA ACTACAGAAC GAACTGATCT GGCGCGAGTA CGAAACTGGC
5221 CCGTATCGGC GTTTCCATGT GCACGAGCCG AAAAAGCGTT TGGTCGCCGC GCTGCCCTTT
5281 CGCGATCGCG TCGTACAGCA CAGCCTAATC GCCGCGATCG AGCCCATTTG GGAGTCGCGA
5341 TTCATCGATC AGAGCTACGC CTGCCGTCCC GGCCGGGGCG TGCACCGCGG TGCAGACAAA
5401 GCCCAACAAT GGCTGCGCGA GGTGCGGGCC ACACACGGCC GCGTCTACGC GCTCAAGGCC
5461 GACGTCGCAG GTTATTTCGC ATCGATCGAT CACGACGTTC TGCGCACGCA GCTAGAACGC
5521 CGAATCGCTT GCCGTCCAAC GCTATACCTG CTGCTCGGCA TCATCGAAAC CTGGCATCCC
5581 GGCCTTCCCA TCGGCAACCT CACGTCGCAG CTGTGCGCCA ATATCTATTT GCACGATTTC
5641 GACGTATTCG CAAAACAGCA CGTCGGCGCA CGCCGCTATA TGAGGTATAT GGATGACTGG
5701 CTCATCGTCG ACCACGACAA AGCGCGCCTG CACGCACAGC GCCGCGTGCT CGAGGACTGG
5761 CTGCACGACA ATCTGCGCCT GCAGCTCAAT AACAAGACCC AGATATTTCC CGTCAGCCCA
5821 CGCCACGGCC GCGGACTCGA CTTCCTCGGA TATCGAATAT GGCCCACACA TCGAAAGATT
5881 CGCAAAAACA GCGTCAAACG gATGCAGAAA AAACTACGTG CGCTCGAACG CCGCTACGCC
5941 GCCGGCGATA TCGACCTGGT CGACATCGAG CCCGTGATCC AGAGCTGGGT CGCCCACGCC
6001 TCCCACGCCA GCAGCTATCA GATCCGCCGC GCGGTGCTGG AGCGCGCGGT TTTCAAACGC
6061 CAATAAGCAT GC
```

J987-pTet DGR214
reprogrammed-to-div1 (D)
(SEQ ID NO: 7)

```
  1 AAGCTTGGCT GTTTTGGCGG ATGAGAGAAG ATTTTCAGCC TGATACAGAT TAAATCAGAA
 61 CGCAGAAGCG GTCTGATAAA ACAGAATTTG CCTGGCGGCA GTAGCGCGGT GGTCCCACCT
121 GACCCCATGC CGAACTCAGA AGTGAAACGC CGTAGCGCCG ATGGTAGTGT GGGGTCTCCC
181 CATGCGAGAG TAGGGAACTG CCAGGCATCA AATAAAACGA AAGGCTCAGT CGAAAGACTG
241 GGCCTTTCGT TTTATCTGTT GTTTGTCGGT GAACGCTCTC CTGAGTAGGA CAAATCCGCC
301 GGGAGCGGAT TTGAACGTTG CGAAGCAACG GCCCGGAGGG TGGCGGGCAG GACGCCCGCC
```

TABLE 3-continued

```
 361 ATAAACTGCC AGGCATCAAA TTAAGCAGAA GGCCATCCTG ACGGATGGCC TTTTTGCGTT
 421 TCTACAAACT CTTTTGTTTA TTTTTCTAAA TACATTCAAA TATGTATCCG CTCATGAGAC
 481 AATAACCCTG ATAAATGCTT CAATAATATT GAAAAAGGAA GAGTATGAGT ATTCAACATT
 541 TCCGTGTCGC CCTTATTCCC TTTTTTGCGG CATTTTGCCT TCCTGTTTTT GCTCACCCAG
 601 AAACGCTGGT GAAAGTAAAA GATGCTGAAG ATCAGTTGGG TGCACGAGTG GGTTACATCG
 661 AACTGGATCT CAACAGCGGT AAGATCCTTG AGAGTTTTCG CCCCGAAGAA CGTTTTCCAA
 721 TGATGAGCAC TTTTAAAGTT CTGCTATGTG GCGCGGTATT ATCCCGTGTT GACGCCGGGC
 781 AAGAGCAACT CGGTCGCCGC ATACACTATT CTCAGAATGA CTTGGTTGAG TACTCACCAG
 841 TCACAGAAAA GCATCTTACG GATGGCATGA CAGTAAGAGA ATTATGCAGT GCTGCCATAA
 901 CCATGAGTGA TAACACTGCG GCCAACTTAC TTCTGACAAC GATCGGAGGA CCGAAGGAGC
 961 TAACCGCTTT TTTGCACAAC ATGGGGGATC ATGTAACTCG CCTTGATCGT TGGGAACCGG
1021 AGCTGAATGA AGCCATACCA AACGACGAGC GTGACACCAC GATGCCTGCA GCAATGGCAA
1081 CAACGTTGCG CAAACTATTA ACTGGCGAAC TACTTACTCT AGCTTCCCGG CAACAATTAA
1141 TAGACTGGAT GGAGGCGGAT AAAGTTGCAG GACCACTTCT GCGCTCGGCC CTTCCGGCTG
1201 GCTGGTTTAT TGCTGATAAA TCTGGAGCCG GTGAGCGTGG GTCTCGCGGT ATCATTGCAG
1261 CACTGGGGGC AGATGGTAAG CCCTCCCGTA TCGTAGTTAT CTACACGACG GGGAGTCAGG
1321 CAACTATGGA TGAACGAAAT AGACAGATCG CTGAGATAGG TGCCTCACTG ATTAAGCATT
1381 GGTAACTGTC AGACCAAGTT TACTCATATA TACTTTAGAT TGATTTACGC GCCCTGTAGC
1441 GGCGCATTAA GCGCGGCGGG TGTGGTGGTT ACGCGCAGCG TGACCGCTAC ACTTGCCAGC
1501 GCCCTAGCGC CCGCTCCTTT CGCTTTCTTC CCTTCCTTTC TCGCCACGTT CGCCGGCTTT
1561 CCCCGTCAAG CTCTAAATCG GGGGCTCCCT TTAGGGTTCC GATTTAGTGC TTTACGGCAC
1621 CTCGACCCCA AAAAACTTGA TTTGGGTGAT GGTTCACGTA GTGGGCCATC GCCCTGATAG
1681 ACGGTTTTTC GCCCTTTGAC GTTGGAGTCC ACGTTCTTTA ATAGTGGACT CTTGTTCCAA
1741 ACTTGAACAA CACTCAACCC TATCTCGGGC TATTCTTTTG ATTTATAAGG GATTTTGCCG
1801 ATTTCGGCCT ATTGGTTAAA AAATGAGCTG ATTTAACAAA AATTTAACGC GAATTTTAAC
1861 AAAATATTAA CGTTTACAAT TTAAAAGGAT CTAGGTGAAG ATCCTTTTTG ATAATCTCAT
1921 GACCAAAATC CCTTAACGTG AGTTTTCGTT CCACTGAGCG TCAGACCCCG TAGAAAAGAT
1981 CAAAGGATCT TCTTGAGATC CTTTTTTTCT GCGCGTAATC TGCTGCTTGC AAACAAAAAA
2041 ACCACCGCTA CCAGCGGTGG TTTGTTTGCC GGATCAAGAG CTACCAACTC TTTTTCCGAA
2101 GGTAACTGGC TTCAGCAGAG CGCAGATACC AAATACTGTC CTTCTAGTGT AGCCGTAGTT
2161 AGGCCACCAC TTCAAGAACT CTGTAGCACC GCCTACATAC CTCGCTCTGC TAATCCTGTT
2221 ACCAGTGGCT GCTGCCAGTG GCGATAAGTC GTGTCTTACC GGGTTGGACT CAAGACGATA
2281 GTTACCGGAT AAGGCGCAGC GGTCGGGCTG AACGGGGGGT TCGTGCACAC AGCCCAGCTT
2341 GGAGCGAACG ACCTACACCG AACTGAGATA CCTACAGCGT GAGCTATGAG AAAGCGCCAC
2401 GCTTCCCGAA GGGAGAAAGG CGGACAGGTA TCCGGTAAGC GGCAGGGTCG GAACAGGAGA
2461 GCGCACGAGG GAGCTTCCAG GGGGAAACGC CTGGTATCTT TATAGTCCTG TCGGGTTTCG
2521 CCACCTCTGA CTTGAGCGTC GATTTTTGTG ATGCTCGTCA GGGGGGCGGA GCCTATGGAA
2581 AAACGCCAGC AACGCGGCCT TTTTACGGTT CCTGGCCTTT TGCTGGCCTT TTGCTCACAT
2641 GTTCTTTCCT GCGTTATCCC CTGATTCTGT GGATAACCGT ATTACCGCCT TTGAGTGAGC
2701 TGATACCGCT CGCCGCAGCC GAACGACCGA GCGCAGCGAG TCAGTGAGCG AGGAAGCGGA
2761 AGAGCGCCTG ATGCGGTATT TTCTCCTTAC GCATCTGTGC GGTATTTCAC ACCGCATACG
2821 TACGGGCGCG CCTTAAGACC CACTTTCACA TTTAAGTTGT TTTTCTAATC CGCATATGAT
2881 CAATTCAAGG CCGAATAAGA AGGCTGGCTC TGCACCTTGG TGATCAAATA ATTCGATAGC
2941 TTGTCGTAAT AATGGCGGCA TACTATCAGT AGTAGGTGTT TCCCTTTCTT CTTTAGCGAC
3001 TTGATGCTCT TGATCTTCCA ATACGCAACC TAAAGTAAAA TGCCCCACAG CGCTGAGTGC
3061 ATATAATGCA TTCTCTAGTG AAAAACCTTG TTGGCATAAA AAGGCTAATT GATTTTCGAG
3121 AGTTTCATAC TGTTTTTCTG TAGGCCGTGT ACCTAAATGT ACTTTTGCTC CATCGCGATG
3181 ACTTAGTAAA GCACATCTAA AACTTTTAGC GTTATTACGT AAAAAATCTT GCCAGCTTTC
3241 CCCTTCTAAA GGGCAAAAGT GAGTATGGTG CCTATCTAAC ATCTCAATGG CTAAGGCGTC
3301 GAGCAAAGCC CGCTTATTTT TTACATGCCA ATACAATGTA GGCTGCTCTA CACCTAGCTT
3361 CTGGGCGAGT TTACGGGTTG TTAAACCTTC GATTCCGACC TCATTAAGCA GCTCTAATGC
3421 GCTGTTAATC ACTTTACTTT TATCTAATCT AGACATCATT AATTCCTAAT TTTTGTTGAC
3481 ACTCTATCGT TGATAGAGTT ATTTTACCAC TCCCTATCAG TGATAGAGAA AAGAATTCAA
3541 AAGATCTAAA GAGGAGAAAG GATCTATGGA CTACAAAGAC GATGACGACA AGggatccAT
3601 GAAGAAACAG AGCAATCAGA CCGTTCGTAT GGCAACACCG GGTCAGATTA AAGATGTTAT
3661 TAGCGCAGTT GTTGAAAGCA TTCCGGTGAA TAATCTGACA TATGAAATGG CCCAGTATTT
3721 CATCGGTCGT AAAAAATGGC TGGGCACCGA AATGAAAAAA ATCTTTAGCG TGGATAACAG
3781 CCATGCAGAT CTGATTGCAG ATTGGCAGGC ATTTTATTGT GGTCTGGGTA TTGATTGCGA
3841 TCTGAGCGGT GTTATTATTC CGGATGATCC TGGGTGGTTTT GGTCGTGTGA TTATTATGGC
3901 ACAGGGTATT ACACCGCAGA GCGGTTATGA TCTGTGTGCA AAATTCTTTC CGTGCTGGAA
3961 ATATACCGAT AAAAACCTGG ATGAAGTTGT GGTTAGCGAA CGTACCGCAA AAGATGTTTA
4021 TGCAATTCGT GTTCGTGATC GTGTTGAAGC AGATGAAGAA CTGCGTAATC GTAGCTATAA
4081 TGATCTGAAA CGTCAGGGCA TTATTGGCAT TACCCTGGAA GAACGTGAAA TCTTTGAACT
4141 GAAATTTTTC AAAGAAACCG CAGGCAAACA CCTGGATATC AAAAATTGGA CCTTTTGTCT
4201 GGGTTCGTGC TATGACGACG GCAATGTGCC GAACGCCAAT TGGAACAGCG GCAAGTTCAA
4261 GGTCAACTGG TACAATCCCg ACAATGTCAA CGACAATCTG TGTTCCCGTC AGGCGGTTTC
4321 CTAGTCGGTT GCCGGCCTGC TTTTGTTGCC TGATGCCTGT TCATCTGTTG TCTGCGGCCC
4381 TGCGCGATAG CGCGGGCCGT CTCTAAAAGA GGAGAAAGGA TCTATGCAAC AGCTTCAAGT
4441 CGCGCAGCGG GTCGAGGCGA TGATCGAGTA TGGCTATATA GCTGTACGGC ATTTCCCGAA
4501 ATCGGAGCGT CACGTGCTCA GCGCCGAGCT GCGCGGCTCT ATGTGGCGGC TGCTGCGGCT
4561 CGTGATCGTC TGCGGCAAGC GGTATCACAA AAAGACGACA CTCGCAGAGC TGGATACCGA
4621 ACTGGAGCTG CTGCGCCGCG AAGTGCGGCT CGCAAAAGAC CTGAAGTTCC TGCCGTTCCG
4681 ACAATCGAA ATCTGGTCGC GTCATCTCGA CGAGATCGGT CGCATGATCG GCGGCTGGAT
4741 TAAACACGCA AAACAGGGTT AAGCGCATTT GGGTTCGTGC TATGACGACG GCAATGTGCC
4801 GAACGCCAAT TGGAACAGCG GCAAGTTCAA GGTCAACTGG TACAATCCCg ACAATGTCAA
4861 CGACAATCTG TGTTCCCGTC AGGCGGTTTC CTAGTCGGTT GCCGGCCTGC TCTTGAAGAT
4921 CGTCAGAAAC AGCGCGGTCA CGGTGGCGCT GTCAGCACGA CATCAAAAGG GCGCTTGATC
4981 CTCGGCCCAT GCCGAAACAT TAACAGGCAT CGATCGTGTA GTAGGCCTCA GCCGAGGCTC
5041 GATCGTCGCC GCTTTGGCTC GATAAAGAGG AGAAAGGATC TATGAAGACA TACAACAACC
5101 TGTTCCCGGA GATATACAGC TTCGACAACC TGCATGACGC CTACGTCCGC GCGCGCCGCG
```

TABLE 3-continued

```
5161 GCAAACGCCA CCAGGCCGAC GTGCTGCGCT TCGAGCAAAA CCTCGAGGGC GAGCTCATAC
5221 AACTACAGAA CGAACTGATC TGGCGCGAGT ACGAAACTGG CCCGTATCGG CGTTTCCATG
5281 TGCACGAGCG GAAAAAGCGT TTGGTCGCCG CGCTGCCCTT TCGCGATCGC GTCGTACAGC
5341 ACAGCCTAAT CGCCGCGATC GAGCCCATTT GGGAGTCGCG ATTCATCGAT CAGAGCTACG
5401 CCTGCCGTCC CGGCCGGGGC GTGCACCGCG GTGCAGACAA AGCCCAACAA TGGCTGCGCG
5461 AGGTGCGGGC CACACACGGC CGCGTCTACG CGCTCAAGGC CGACGTCGCA GGTTATTTCG
5521 CATCGATCGA TCACGACGTT CTGCGCACGC AGCTAGAACG CCGAATCGCT TGCCGTCCAA
5581 CGCTATACCT GCTGCTCGGC ATCATCGAAA CCTGGCATCC CGGCCTTCCC ATCGGCAACC
5641 TCACGTCGCA GCTGTGCGCC AATATCTATT TGCACGATTT CGACGTATTC GCAAAACAGC
5701 ACGTCGGCGC ACGCCGCTAT ATGAGGTATA TGGATGACTG GCTCATCGTC GACCACGACA
5761 AAGCGCGCCT GCACGCACAG CGCCGCGTGC TCGAGGACTG GCTGCACGAC AATCTGCGCC
5821 TGCAGCTCAA TAACAAGACC CAGATATTTC CCGTCAGCCC ACGCCACGGC CGCGGACTCG
5881 ACTTCCTCGG ATATCGAATA TGGCCCACAC ATCGAAAGAT TCGCAAAAAC AGCGTCAAAC
5941 GgATGCAGAA AAAACTACGT GCGCTCGAAC GCCGCTACGC CGCCGGCGAT ATCGACCTGG
6001 TCGACATCGA GCCCGTGATC CAGAGCTGGG TCGCCCACGC CTCCCACGCC AGCAGCTATC
6061 AGATCCGCCG CGCGGTGCTG GAGCGCGCGG TTTTCAAACG CCAATAAGCA TGC
```

J990-pTet DGR214
reprogrammed-to-div1 (G)
(SEQ ID NO: 8)

```
   1 AAGCTTGGCT GTTTTGGCGG ATGAGAGAAG ATTTTCAGCC TGATACAGAT TAAATCAGAA
  61 CGCAGAAGCG GTCTGATAAA ACAGAATTTG CCTGGCGGCA GTAGCGCGGT GGTCCCACCT
 121 GACCCCATGC CGAACTCAGA AGTGAAACGC CGTAGCGCCG ATGGTAGTGT GGGGTCTCCC
 181 CATGCGAGAG TAGGGAACTG CCAGGCATCA AATAAAACGA AAGGCTCAGT CGAAAGACTG
 241 GGCCTTTCGT TTTATCTGTT GTTTGTCGGT GAACGCTCTC CTGAGTAGGA CAAATCCGCC
 301 GGGAGCGGAT TTGAACGTTG CGAAGCAACG GCCCGGAGGG TGGCGGGCAG GACGCCCGCC
 361 ATAAACTGCC AGGCATCAAA TTAAGCAGAA GGCCATCCTG ACGGATGGCC TTTTTGCGTT
 421 TCTACAAACT CTTTTGTTTA TTTTTCTAAA TACATTCAAA TATGTATCCG CTCATGAGAC
 481 AATAACCCTG ATAAATGCTT CAATAATATT GAAAAAGGAA GAGTATGAGT ATTCAACATT
 541 TCCGTGTCGC CCTTATTCCC TTTTTTGCGG CATTTTGCCT TCCTGTTTTT GCTCACCCAG
 601 AAACGCTGGT GAAAGTAAAA GATGCTGAAG ATCAGTTGGG TGCACGAGTG GGTTACATCG
 661 AACTGGATCT CAACAGCGGT AAGATCCTTG AGAGTTTTCG CCCCGAAGAA CGTTTTCCAA
 721 TGATGAGCAC TTTTAAAGTT CTGCTATGTG GCGCGGTATT ATCCCGTGTT GACGCCGGGC
 781 AAGAGCAACT CGGTCGCCGC ATACACTATT CTCAGAATGA CTTGGTTGAG TACTCACCAG
 841 TCACAGAAAA GCATCTTACG GATGGCATGA CAGTAAGAGA ATTATGCAGT GCTGCCATAA
 901 CCATGAGTGA TAACACTGCG GCCAACTTAC TTCTGACAAC GATCGGAGGA CCGAAGGAGC
 961 TAACCGCTTT TTTGCACAAC ATGGGGGATC ATGTAACTCG CCTTGATCGT TGGGAACCGG
1021 AGCTGAATGA AGCCATACCA AACGACGAGC GTGACACCAC GATGCCTGCA GCAATGGCAA
1081 CAACGTTGCG CAAACTATTA ACTGGCGAAC TACTTACTCT AGCTTCCCGG CAACAATTAA
1141 TAGACTGGAT GGAGGCGGAT AAAGTTGCAG GACCACTTCT GCGCTCGGCC CTTCCGGCTG
1201 GCTGGTTTAT TGCTGATAAA TCTGGAGCCG GTGAGCGTGG GTCTCGCGGT ATCATTGCAG
1261 CACTGGGGCC AGATGGTAAG CCCTCCCGTA TCGTAGTTAT CTACACGACG GGGAGTCAGG
1321 CAACTATGGA TGAACGAAAT AGACAGATCG CTGAGATAGG TGCCTCACTG ATTAAGCATT
1381 GGTAACTGTC AGACCAAGTT TACTCATATA TACTTTAGAT TGATTTACGC GCCCTGTAGC
1441 GGCGCATTAA GCGCGGCGGG TGTGGTGGTT ACGCGCAGCG TGACCGCTAC ACTTGCCAGC
1501 GCCCTAGCGC CCGCTCCTTT CGCTTTCTTC CCTTCCTTTC TCGCCACGTT CGCCGGCTTT
1561 CCCCGTCAAG CTCTAAATCG GGGGCTCCCT TTAGGGTTCC GATTTAGTGC TTTACGGCAC
1621 CTCGACCCCA AAAAACTTGA TTTGGGTGAT GGTTCACGTA GTGGGCCATC GCCCTGATAG
1681 ACGGTTTTTC GCCCTTTGAC GTTGGAGTCC ACGTTCTTTA ATAGTGGACT CTTGTTCCAA
1741 ACTTGAACAA CACTCAACCC TATCTCGGGC TATTCTTTTG ATTTATAAGG GATTTTGCCG
1801 ATTTCGGCCT ATTGGTTAAA AAATGAGCTG ATTTAACAAA AATTTAACGC GAATTTTAAC
1861 AAAATATTAA CGTTTACAAT TTAAAAGGAT CTAGGTGAAG ATCCTTTTTG ATAATCTCAT
1921 GACCAAAATC CCTTAACGTG AGTTTTCGTT CCACTGAGCG TCAGACCCCG TAGAAAAGAT
1981 CAAAGGATCT TCTTGAGATC CTTTTTTTCT GCGCGTAATC TGCTGCTTGC AAACAAAAAA
2041 ACCACCGCTA CCAGCGGTGG TTTGTTTGCC GGATCAAGAG CTACCAACTC TTTTTCCGAA
2101 GGTAACTGGC TTCAGCAGAG CGCAGATACC AAATACTGTC CTTCTAGTGT AGCCGTAGTT
2161 AGGCCACCAC TTCAAGAACT CTGTAGCACC GCCTACATAC CTCGCTCTGC TAATCCTGTT
2221 ACCAGTGGCT GCTGCCAGTG GCGATAAGTC GTGTCTTACC GGGTTGGACT CAAGACGATA
2281 GTTACCGGAT AAGGCGCAGC GGTCGGGCTG AACGGGGGGT TCGTGCACAC AGCCCAGCTT
2341 GGAGCGAACG ACCTACACCG AACTGAGATA CCTACAGCGT GAGCTATGAG AAAGCGCCAC
2401 GCTTCCCGAA GGGAGAAAGG CGGACAGGTA TCCGGTAAGC GGCAGGGTCG GAACAGGAGA
2461 GCGCACGAGG GAGCTTCCAG GGGGAAACGC CTGGTATCTT TATAGTCCTG TCGGGTTTCG
2521 CCACCTCTGA CTTGAGCGTC GATTTTTGTG ATGCTCGTCA GGGGGGCGGA GCCTATGGAA
2581 AAACGCCAGC AACGCGGCCT TTTTACGGTT CCTGGCCTTT TGCTGGCCTT TTGCTCACAT
2641 GTTCTTTCCT GCGTTATCCC CTGATTCTGT GGATAACCGT ATTACCGCCT TTGAGTGAGC
2701 TGATACCGCT CGCCGCAGCC GAACGACCGA GCGCAGCGAG TCAGTGAGCG AGGAAGCGGA
2761 AGAGCGCCTG ATGCGGTATT TTCTCCTTAC GCATCTGTGC GGTATTTCAC ACCGCATACG
2821 TACGGGCGCG CCTTAAGACC CACTTTCACA TTTAAGTTGT TTTTCTAATC CGCATATGAT
2881 CAATTCAAGG CCGAATAAGA AGGCTGGCTC TGCACCTTGG TGATCAAATA ATTCGATAGC
2941 TTGTCGTAAT AATGGCGGCA TACTATCAGT AGTAGGTGTT TCCCTTTCTT CTTTAGCGAC
3001 TTGATGCTCT TGATCTTCCA ATACGCAACC TAAAGTAAAA TGCCCCACAG CGCTGAGTGC
3061 ATATAATGCA TTCTCTAGTG AAAAACCTTG TTGGCATAAA AAGGCTAATT GATTTTCGAG
3121 AGTTTCATAC TGTTTTTCTG TAGGCCGTGT ACCTAAATGT ACTTTTGCTC CATCGCGATG
3181 ACTTAGTAAA GCACATCTAA AACTTTTAGC GTTATTACGT AAAAAATCTT GCCAGCTTTC
3241 CCCTTCTAAA GGGCAAAAGT GAGTATGGTG CCTATCTAAC ATCTCAATGG CTAAGGCGTC
3301 GAGCAAAGCC CGCTTATTTT TTACATGCCA ATACAATGTA GGCTGCTCTA CACCTAGCTT
3361 CTGGGCGAGT TTACGGGTTG TTAAACCTTC GATTCCGACC TCATTAAGCA GCTCTAATGC
3421 GCTGTTAATC ACTTTACTTT TATCTAATCT AGACATCATT AATTCCTAAT TTTTGTTGAC
3481 ACTCTATCGT TGATAGAGTT ATTTTACCAC TCCCTATCAG TGATAGAGAA AAGAATTCAA
3541 AAGATCTAAA GAGGAGAAAG GATCTATGGA CTACAAAGAC GATGACGACA AGggatccAT
3601 GAAGAAACAG AGCAATCAGA CCGTTCGTAT GGCAACACCG GGTCAGATTA AGATGTTTAT
3661 TAGCGCAGTT GTTGAAAGCA TTCCGGTGAA TAATCTGACA TATGAAATGG CCCAGTATTT
3721 CATCGGTCGT AAAAAATGGC TGGGCACCGA AATGAAAAAA ATCTTTAGCG TGGATAACAG
```

TABLE 3-continued

```
3781  CCATGCAGAT CTGATTGCAG ATTGGCAGGC ATTTTATTGT GGTCTGGGTA TTGATTGCGA
3841  TCTGAGCGGT GTTATTATTC CGGATGATCC TGGTGGTTTT GGTCGTGTGA TTATTATGGC
3901  ACAGGGTATT ACACCGCAGA GCGGTTATGA TCTGTGTGCA AAATTCTTTC CGTGCTGGAA
3961  ATATACCGAT AAAAACCTGG ATGAAGTTGT GGTTAGCGAA CGTACCGCAA AAGATGTTTA
4021  TGCAATTCGT GTTCGTGATC GTGTTGAAGC AGATGAAGAA CTGCGTAATC GTAGCTATAA
4081  TGATCTGAAA CGTCAGGGCA TTATTGGCAT TACCCTGGAA GAACGTGAAA TCTTTGAACT
4141  GAAATTTTTC AAAGAAACCG CAGGCAAACA CCTGGATATC AAAAATTGGA CCTTTTGTCT
4201  GGGTTCGTGC TATGACGGCG GCAATGTGCC GAGCGCCTCG TGGCGCAGCG GCGAGTTCGA
4261  GGTCGACTGG TGCAATCCCG GCGATGTCTT CGACGATCTG TGTTCCCGTC AGGCTTTTGT
4321  TGCCTGATGC CTGTTCATCT GTGTTCTGCG GCCCTGCGCG ATAGCGCGGG CCGTCTCTAA
4381  AAGAGGAGAA AGGATCTATG CAACAGCTTC AAGTCGCGCA GCGGGTCGAG GCGATGATCG
4441  AGTATGGCTA TATAGCTGTA CGGCATTTCC CGAAATCGGA GCGTCACGTG CTCAGCGCCG
4501  AGCTGCGCGG CTCTATGTGG CGGCTGCTGC GGCTCGTGAT CGTCTGCGGC AAGCGGTATC
4561  ACAAAAAGAC GACACTCGCA GAGCTGGATA CCGAACTGGA GCTGCTGCGC CGCGAAGTGC
4621  GGCTCGCAAA AGACCTGAAG TTCCTGCCGT TCCGACAATA CGAAATCTGG TCGCGTCATC
4681  TCGACGAGAT CGGTCGCATG ATCGGCGGCT GGATTAAACA CGCAAAACAG GGTTAAGCGC
4741  ATTTGGGTTC GTGCTATGAC GACGGCAATG TGCCGAACGC CAATTGGAAC AGCGGCAAGT
4801  TCAAGGTCAA CTGGTACAAT CCCgACAATG TCAACGACAA TCTGTGTTCC CGTCAGGCTC
4861  TTGAAGATCG TCAGAAACAG CGCGGTCACG GTGGCGCTGT CAGCACGACA TCAAAAGGGC
4921  GCTTGATCCT CGGCCCATGC CGAAACATTA ACAGGCATCG ATCGTGTAGT AGGCCTCAGC
4981  CGAGGCTCGA TCGTCGCCGC TTTGGCTCGA TAAAGAGGAG AAAGGATCTA TGAAGACATA
5041  CAACAACCTG TTCCCGGAGA TATACAGCTT CGACAACCTG CATGACGCCT ACGTCCGCGC
5101  GCGCCGCGGC AAACGCCACC AGGCCGACGT GCTGCGCTTC GAGCAAAACC TCGAGGGCGA
5161  GCTCATACAA CTACAGAACG AACTGATCTG GCGCGAGTAC GAAACTGGCC CGTATCGGCG
5221  TTTCCATGTG CACGAGCCGA AAAAGCGTTT GGTCGCCGCG CTGCCCTTTC GCGATCGCGT
5281  CGTACAGCAC AGCCTAATCG CCGCGATCGA GCCCATTTGG GAGTCGCGAT TCATCGATCA
5341  GAGCTACGCC TGCCGTCCCG GCCGGGGCGT GCACCGCGGT GCAGACAAAG CCCAACAATG
5401  GCTGCGCGAG GTGCGGGCCA CACACGGCCG CGTCTACGCG CTCAAGGCCG ACGTCGCAGG
5461  TTATTTCGCA TCGATCGATC ACGACGTTCT GCGCACGCAG CTAGAACGCC GAATCGCTTG
5521  CCGTCCAACG CTATACCTGC TGCTCGGCAT CATCGAAACC TGGCATCCCG GCCTTCCCAT
5581  CGGCAACCTC ACGTCGCAGC TGTGCGCCAA TATCTATTTG CACGATTTCG ACGTATTCGC
5641  AAAACAGCAC GTCGGCGCAC GCCGCTATAT GAGGTATATG GATGACTGGC TCATCGTCGA
5701  CCACGACAAA GCGCGCCTGC ACGCACAGCG CCGCGTGCTC GAGGACTGGC TGCACGACAA
5761  TCTGCGCCTG CAGCTCAATA ACAAGACCCA GATATTTCCC GTCAGCCCAC GCCACGGCCG
5821  CGGACTCGAC TTCCTCGGAT ATCGAATATG GCCCACACAT CGAAAGATTC GCAAAAACAG
5881  CGTCAAACGg ATGCAGAAAA AACTACGTGC GCTCGAACGC CGCTACGCCG CCGGCGATAT
5941  CGACCTGGTC GACATCGAGC CCGTGATCCA GAGCTGGGTC GCCCACGCCT CCCACGCCAG
6001  CAGCTATCAG ATCCGCCGCG CGGTGCTGGA GCGCGCGGTT TTCAAACGCC AATAAGCATG
6061  C
```

35

Example 5

A method/algorithm for identifying self-diversifying systems:

Parameters:

D=distance of two constant flanking 32-mers, typically 192 or 160 bases

T=minimum number of diverse instances for a hash to be retained, typically 6

R=number of scanning rounds, typically 3

Method/Algorithm:

1. A large amount of memory (e.g. 512 GB) was allocated to an array of 16 bit-integers (named A).

2. The source sequence database was parsed base-by-base in both sense and reverse-complement orientation.

At every source position, a hash H1 was calculated of the input 32-mer sequence at that position concatenated by the input 32-mer sequence that was D bases downstream of the first 32-mer.

Hash H1 was reduced to the available number of index bits of A by a modulo or other function.

A second hash H2 was calculated from an 8-mer sequence positioned D/2 downstream of the first 32-mer, or at a defined position between the two 32-mers that were used to calculate H1.

Hash H2 was reduced to 4 bits by a modulo or other function.

The element at address H1 in array A was altered by an OR operation with the value 2/\H2.

3. All elements of array A, in which at least T bits were positive, were copied to a separate table A2.

4. Steps 1-3 here were repeated for a total of R rounds, wherein only source sequences were considered whose hash H1 had been retained in the previous round. In every round, a different hash function was used to calculate the new H1 for aggregating in array A.

5. After the last round was completed, the source sequence database was parsed base-by-base again in both sense and reverse-complement orientation, aggregating sequence logos for each retained hash value separately.

6. Sequence logos were stored, optionally filtered for redundant sequences, optionally filtered for a minimum length of highly conserved sequence, and optionally filtered for an arbitrary diversity score calculated from each logo.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/docdetail?docId=US12606815B2). An electronic copy of the sequence listing will also be available from the USPTO upon request and payment of the fee set forth in 37 CFR 1.19(b)(3).

What is claimed is:

1. A self-diversifying system comprising an in vitro engineered vector, wherein the vector comprises a promoter, a polynucleotide sequence, and a nucleic acid template region, wherein the polynucleotide sequence is operably linked to the promoter, is the nucleotide sequence selected from SEQ ID Nos. 98-123, and comprises one or more open reading frames, wherein at least one of the open reading frames comprises a self-diversifying element, wherein the nucleic acid template region is operably linked to a nucleic acid variable region of the polynucleotide sequence, and wherein the self-diversifying element is a diversity generating retroelement (DGR) or a non-DGR.

2. The system of claim 1, wherein the self-diversifying element is a (DGR).

3. The system of claim 1, wherein the self-diversifying element is a non-DGR.

4. The system of claim 1, further comprising a reverse transcriptase or functional domain thereof.

5. The system of claim 1, wherein the polynucleotide sequence encodes c-type lectin fold or a fragment thereof.

6. The system of claim 1, wherein the polynucleotide sequence encodes a protein or polypeptide capable of binding to a protein or a nucleic acid.

7. The system of claim 1, wherein the nucleic acid variable region and the nucleic acid template region have a sequence homology less than 80%.

8. The system of claim 1, wherein the system is capable of generating a population of proteins.

9. The system of claim 1, wherein the system is capable of generating a population of polynucleotides.

10. The system of claim 1, wherein the system is capable of generating one or more binding partners of a target molecule.

11. The system of claim 10, wherein the target molecule is a protein.

12. The system of claim 10, wherein the target molecule is an antigen.

13. The system of claim 10, wherein the target molecule is a polynucleotide.

14. The system of claim 1, wherein the system generates a library of diversified molecules when the vector is introduced to cells.

15. The system of claim 14, wherein the diversified molecules are polynucleotide-binding proteins or polypeptide-binding proteins.

16. The system of claim 15, wherein the polynucleotide-binding proteins or polypeptide-binding proteins are selected from SEQ ID NOs: 3 and 4.

17. The system of claim 16, wherein SEQ ID NOs: 3 and 4 are encoded by SEQ ID NO: 1 and 2 respectively.

18. The system of claim 1, wherein the nucleic acid variable region is within an open reading frame of the one or more open reading frames.

19. The system of claim 1, wherein the self-diversifying element comprises one or more initiation of mutagenic homing (IMH) sequences.

* * * * *